United States Patent
Lavoie et al.

(10) Patent No.: US 9,573,938 B2
(45) Date of Patent: Feb. 21, 2017

(54) THERAPEUTIC HYDROXYPYRIDINONES, HYDROXYPYRIMIDINONES AND HYDROXYPYRIDAZINONES

(71) Applicant: RUTGERS, THE STATE UNIVERSITY OF NEW JERSEY, New Brunswick, NJ (US)

(72) Inventors: Edmond J. Lavoie, New Brunswick, NJ (US); Joseph David Bauman, New Brunswick, NJ (US); Ajit Parhi, New Brunswick, NJ (US); Hye Yeon Sagong, New Brunswick, NJ (US); Disha Patel, New Brunswick, NJ (US); Eddy Arnold, New Brunswick, NJ (US); Kalyan Das, New Brunswick, NJ (US); Suyambu Kesava Vijayan, New Brunswick, NJ (US)

(73) Assignee: Rutgers, The State University of New Jersey, New Brunswick, NJ (US)

(*) Notice: Subject to any disclaimer, the term of this patent is extended or adjusted under 35 U.S.C. 154(b) by 0 days.

(21) Appl. No.: 14/426,948

(22) PCT Filed: Sep. 11, 2013

(86) PCT No.: PCT/US2013/059287
§ 371 (c)(1),
(2) Date: Mar. 9, 2015

(87) PCT Pub. No.: WO2014/043252
PCT Pub. Date: Mar. 20, 2014

(65) Prior Publication Data
US 2015/0232454 A1    Aug. 20, 2015

Related U.S. Application Data

(60) Provisional application No. 61/699,676, filed on Sep. 11, 2012, provisional application No. 61/861,788, filed on Aug. 2, 2013.

(51) Int. Cl.
| | | |
|---|---|---|
| C07D 237/16 | (2006.01) |
| C07D 401/10 | (2006.01) |
| A61K 31/44 | (2006.01) |
| C07D 403/10 | (2006.01) |
| C07D 213/69 | (2006.01) |
| C07D 239/54 | (2006.01) |
| C07D 401/14 | (2006.01) |

(52) U.S. Cl.
CPC ......... *C07D 403/10* (2013.01); *C07D 213/69* (2013.01); *C07D 237/16* (2013.01); *C07D 239/54* (2013.01); *C07D 401/10* (2013.01); *C07D 401/14* (2013.01)

(58) Field of Classification Search
None
See application file for complete search history.

(56) References Cited

FOREIGN PATENT DOCUMENTS

| WO | 00/61563 | 10/2000 |
|---|---|---|
| WO | 02/24650 | 3/2002 |
| WO | 2005/074513 | 8/2005 |
| WO | 2009/154870 | 12/2009 |
| WO | 2012/106534 | 8/2012 |

OTHER PUBLICATIONS

Ried et al, Justus Liebigs Annalen der Chemie (1969), 725, 230-3 with Chemical Abstracts Service, Database Accession No. 1969:491235 (Abstract).*
Wu et al., Toxicology, 236, pp. 1-6, 2007.*
Baughman et al., "Identification of Influenza Endonuclease Inhibitors Using a Novel Fluorescence Polarization Assay", ACS Chemical Biology 7(3), 526-534, (2012).
Das et al., "Structures of influenza A proteins and insights into antiviral drug targets", Nature Structural and Molecular Biology vol. 17 (5), 530-538 (2010).
Database CAPLUS Chemical Abstracts Service, Meerbach et al., "In vitro activity of polyhydroxycarboxylates against herpesviruses and HIV", Antiviral Chemistry and Chemotherapy 12 (6), 337-345 (2002).
Database CAPLUS Chemical Abstracts Service, Im, Isak et al., "Structure-activity relationships of heteroaromatic asters as human rhinovirus 3C protease inhibitors", Bioorganic & Medicinal Chemistry Letters 19(13), 3632-3636 (2009).
Duplantier et al., "Discovery, SAR, and Pharmacokinetics of a Novel 3-Hydroxyquinolin-2(1H)-one Series of Potent D-Amino Acid Oxidase (DAAO) Inhibitors", Journal of Medicinal Chemistry, vol. 52 (11), 3576-3585 (2009).
Fukuyasu et al., "In Vitro and In Vivo Antiviral Activities of L-Beta-(5-Hydroxy-2-Pyridyl)-Alanine (SF-1346) and L-Beta-(3-Hydroxyureido)-Alanine (SF-1293B) and Their Related Aminoacid Analogs", Meiji Seika Kenkyu Nempo-Scientific Reports of Meiji Seikakaisha, 22, 9-17 (1983).
M et al., "Structure-activity relationships of heteroaromatic esters as human rhinovirus 3C protease inhibitors", Bioorganic & Medicinal Chemistry Letters, vol. 19 (13), 3632-3636 (2009).
Patent Cooperation Treaty, International Searching Authority, Search Report and Written Opinion for PCT/US2013/059287, 19 pages, Apr. 17, 2014.

* cited by examiner

*Primary Examiner* — Zinna Northington Davis
(74) *Attorney, Agent, or Firm* — Viksnins Harris & Padys PLLP

(57) ABSTRACT

The invention provides compounds of formula (I): and salts and prodrugs thereof wherein R4, X1 and X2 have any of the meanings defined in the specification, as well as pharmaceutical compositions comprising the compounds or salts and methods for their use in therapy. The compounds have useful antiviral properties.

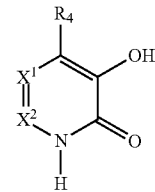

17 Claims, 3 Drawing Sheets

THERAPEUTIC HYDROXYPYRIDINONES, HYDROXYPYRIMIDINONES AND HYDROXYPYRIDAZINONES

RELATED APPLICATIONS

This application is a 35 U.S.C. 371 application of International Application No. PCT/US2013/059287, filed Sep. 11, 2013, which claims priority to United States Provisional Application No. 61/699,676, filed Sep. 11, 2012—and United States Provisional Application No. 61/861,788 that was filed on Aug. 2, 2013.

BACKGROUND OF THE INVENTION

Influenza A infects a wide range of avian and mammalian hosts. The constant ability of the virus to evolve requires reformulation of seasonal influenza vaccines on a yearly basis. The virus has eight genomic RNA segments; reassortment of genomic RNAs from different strains and subtypes of influenza A is responsible for sporadic emergence of pandemic flu (Palese, P.; Shaw, M. L. Orthomyxoviridae: The Viruses and Their Replication. In Fields Virology, 5th ed., 2001; and Knipe, D. M., Howley, P. M., Eds.; Lippincott Williams & Wilkins: Philadelphia, Pa., 2007; Vol. 2, pp 1647-1689). Alternatively, all eight genomic RNAs may be derived from an avian virus, and such a progenitor virus then undergoes multiple mutations in the process of adapting to a mammalian host (Taubenberger et al., Nature. 2005; 437(7060): 889-93).

Antivirals are used for both prophylactic and therapeutic treatments of influenza infection. The available treatment options for influenza are limited. Current antivirals are directed against the M2 ion-channel protein (adamantanes) and neuraminidase (zanamivir and oseltamivir). The adamantane drugs, amantadine and rimantadine, are ineffective due to emergence of resistance (predominantly through a M2 mutation, S31N) and these drugs, in general, are not in clinical use. The neuraminidase (NA)-inhibiting oral drug, oseltamivir (Tamiflu) is widely used for treating flu. Oseltamivir-resistant seasonal influenza A strains have been circulating for several years (Moscona, N Engl J Med. 2005; 353(25):2633-6). The mutant viruses predominantly contain the NA H274Y mutation. When accompanied by compensatory mutations, the mutant viruses exhibit fitness comparable to wild-type influenza A and remain resistant to oseltamivir (Bloom et al., Science. 2010; 328(5983):1272-5). These mutations can emerge in almost all influenza A subtypes/strains, including the pandemic 2009 H1N1 virus (Memoli et al., J Infect Dis. 2011; 203(3):348-57), resulting in a major concern for an effective treatment of flu. Therefore, new drugs are essential for treating drug-resistant and future pandemic flu strains.

Influenza A contains eight negative-stranded RNA genomic segments. The three largest genomic RNA segments encode the viral RNA-dependent RNA polymerase (RdRP) proteins consisting of the polymerase acidic protein (PA) and polymerase basic protein 1 (PB1) and 2 (PB2) subunits. The PA subunit: (i) has endonuclease activity (ii) is involved in viral RNA (vRNA)/complementary RNA (cRNA) promoter binding, and (iii) interacts with the PB1 subunit (reviewed by Das et al., Nat Struct Mol Biol. 2010; 17(5):530-8). PA has two domains, $PA_N$ (a ~25 kDa N-terminal domain; residues 1-197) and $PA_C$ (~55 kDa C-terminal domain; residues 239-716). Crystal structures of $PA_C$ have been determined in complexes with N-terminal fragments of PB1 (He et al., Nature. 2008; 454(7208):1123-6).

The RdRP of influenza A is responsible for the replication and transcription of the viral RNA genes. The viral mRNA transcription involves a cap-snatching mechanism in which the polymerase binds to cellular mRNA via the 5'-cap and cleaves the mRNA 12-13 nucleotides downstream. The cleaved RNA fragment containing the 5' cap acts as a primer for viral mRNA synthesis (Plotch et al., Cell. 1981; 23(2): 847-58). Cap-snatching is an important event in the life cycle of all members of Orthomyxoviridae family including influenza A, B and C viruses, and the host cell has no analogous activity. Therefore, inhibitors of cap-snatching would act against all influenza subtypes and strains, including tamiflu-resistant influenza A viruses, and will not interfere with host cell activities.

The complete structure of the viral polymerase has not yet been determined at atomic resolution; however, recent structural studies of parts of the influenza A polymerase (reviewed by Das et al., Nat Struct Mol Biol. 2010; 17(5):530-8) have begun to elucidate the architecture of this complex and started to identify multiple promising target sites for designing new influenza drugs. The crystal structures of the N-terminal domain of PA subunit ($PA_N$) from H5N1 (Yuan et al., Nature. 2009; 458(7240):909-13) and H3N2 (Dias et al., Nature. 2009; 458(7240):914-8) viruses established that the $PA_N$ domain contains the endonuclease active site composed of conserved acidic residues E80, D108, and E119 positioned in a deep cleft. Blocking the binding of host mRNAs to the cleft and/or inhibiting the cleavage of the host mRNAs would inhibit the synthesis of the viral mRNAs and thereby, inhibit replication of influenzaA.

The $PA_N$ domain of 2009 pandemic H1N1 virus polymerase (residues 1-204) has now been crystallized in three distinct forms (U.S. patent application Ser. No. 13/554,709). These new crystal forms provide for the determination of 3-dimensional structures of $PA_N$ with endonuclease inhibitors. In addition, a high-throughput methodology (U.S. patent application Ser. No. 13/554,709) has been developed and optimized for screening of compounds for influenza endonuclease inhibition.

Compounds, which inhibit influenza endonuclease, may have inhibitory effects on other drug targets owing to the conserved geometry of the catalytic metals in nucleases and polynucleotidyl transferases. Indeed, early influenza endonuclease inhibitors were developed into an anti-AIDS drug targeting HIV-1 integrase (Summa et al., J Med Chem. 2008; 51(18):5843-55). Other viral drug targets with similar geometry at their catalytic cores include, but are not limited to: NS5b RNA-dependent RNA polymerase of hepatitis C virus (Summa et al., J Med Chem. 2008; 51(18):5843-55), RNase H of HIV-1 reverse transcriptase (Himmel et al., Structure. 2009; 17(12): 1625-35), herpes virus terminase (Nadal et al., Proc Natl Acad Sci USA. 2010; 107(37):16078-83), and SARS coronavirus NTPase/helicase. Two metal chelating compounds have also been found to have antibacterial effects (Drakulić et al., Chem Med Chem. 2009; 4(12):1971-75) and antibacterial prenyl transferases specifically (Zhang et al., ACS Med Chem Lett. 2012; 3(5):402-6). In addition to antiviral and antibacterial effects, two metal chelating agents can have cytotoxic effects on eukaryotic cells. One set of compounds was found to have selective anti-leukemic cytotoxicity by inhibiting a terminal deoxyribonucleotidyl transferase (Locatelli et al., Mol Pharm. 2005; 68(2):538-50). In addition, it has been suggested that administration of D-serine with a D-amino acid oxidase (DAAO) inhibitor could allow for more effective delivery of D-serine to the brain, which could be effective in the treatment of symptoms of schizophrenia. Several compounds related to 3-hydroxypyridin(1H)2-ones and its aza-analogs have recently been reported to have activity as D-amino acid oxidase inhibitors (Hondo, et al., J. Med. Chem. 2012, 56, 3582-3592; Duplantier et al, J. Med. Chem., 2009, 52, 3576-3585).

SUMMARY OF THE INVENTION

Accordingly the invention provides a compound of formula I:

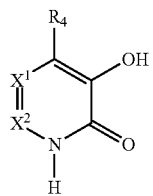

I wherein:
$X^1$ is $CR_5$ and $X^2$ is $CR_6$; or $X^1$ is N and $X^2$ is $CR_6$; or $X^1$ is $CR_5$ and $X^2$ is N;

$R_4$ is H, halo, cyano, nitro, $(C_1-C_6)$alkyl, $(C_2-C_6)$alkenyl, $(C_2-C_6)$alkynyl, $(C_1-C_6)$alkoxy, $(C_3-C_{12})$carbocycle, aryl, heteroaryl, heterocycle, —$NR^aR^b$, —$S(O)_nR^c$, —$S(O)_n NR^aR^b$, —$N(R^y)S(O)_nR^c$, —$COOR^c$, or —$CONR^aR^b$, wherein each $(C_1-C_6)$alkyl, $(C_2-C_6)$alkenyl, $(C_2-C_6)$alkynyl, $(C_1-C_6)$alkoxy, $(C_3-C_{12})$carbocycle of $R_4$ is optionally substituted with one or more groups independently selected from $R_m$; and wherein each aryl, heterocycle, and heteroaryl of $R_4$ is optionally substituted with one or more groups independently selected from $R_n$;

$R_5$ is H, halo, cyano, nitro, $(C_1-C_6)$alkyl, $(C_2-C_6)$alkenyl, $(C_2-C_6)$alkynyl, $(C_1-C_6)$alkoxy, $(C_3-C_{12})$carbocycle, aryl, heteroaryl, heterocycle, —$NR^aR^b$, —$S(O)_nR^c$, —$N(R^y)S(O)_nR^c$, —$S(O)_nNR^aR^b$, —$COOR^c$, or —$CONR^aR^b$, wherein each $(C_1-C_6)$alkyl, $(C_2-C_6)$alkenyl, $(C_2-C_6)$alkynyl, $(C_1-C_6)$alkoxy, $(C_3-C_{12})$carbocycle of $R_5$ is optionally substituted with one or more groups independently selected from $R_m$; and wherein each aryl, heterocycle, and heteroaryl of $R_5$ is optionally substituted with one or more groups independently selected from $R_n$;

$R_6$ is H, halo, cyano, nitro, $(C_1-C_6)$alkyl, $(C_2-C_6)$alkenyl, $(C_2-C_6)$alkynyl, $(C_1-C_6)$alkoxy, $(C_3-C_{12})$carbocycle, aryl, heteroaryl, heterocycle, —$NR^aR^b$, —$S(O)_nR^c$, —$N(R^y)S(O)_nR^c$, —$S(O)_nNR^aR^b$, —$COOR^c$, or —$CONR^aR^b$, wherein each $(C_1-C_6)$alkyl, $(C_2-C_6)$alkenyl, $(C_2-C_6)$alkynyl, $(C_1-C_6)$alkoxy, $(C_3-C_{12})$carbocycle of $R_6$ is optionally substituted with one or more groups independently selected from $R_m$; and wherein each aryl, heterocycle and heteroaryl of $R_6$ is optionally substituted with one or more groups independently selected from $R_n$;

each $R^a$ and $R^b$ is independently selected from hydrogen, $(C_1-C_6)$alkyl, $(C_1-C_6)$alkanoyl, aryl$(C_1-C_6)$alkyl, heteroaryl $(C_1-C_6)$alkyl, $(C_3-C_{12})$carbocycle, aryl, and heteroaryl, wherein each $(C_1-C_6)$alkyl, $(C_1-C_6)$alkanoyl, and $(C_3-C_{12})$carbocycle of $R^a$ and $R^b$ is optionally substituted with one or more groups independently selected from $R_m$; and wherein each aryl and heteroaryl of $R^a$ and $R^b$ is optionally substituted with one or more groups independently selected from $R_n$;

each $R^c$ is independently selected from hydrogen, hydroxy, $(C_1-C_6)$alkyl, $(C_1-C_6)$alkanoyl, aryl$(C_1-C_6)$alkyl, heteroaryl$(C_1-C_6)$alkyl, $(C_3-C_{12})$carbocycle, aryl, and heteroaryl, wherein each $(C_1-C_6)$alkyl, $(C_1-C_6)$alkanoyl, and $(C_3-C_{12})$carbocycle of $R^c$ is optionally substituted with one or more groups independently selected from $R_m$; and wherein each aryl and heteroaryl of $R^c$ is optionally substituted with one or more groups independently selected from $R_n$;

each $R^e$ and $R^f$ is independently selected from hydrogen, $(C_1-C_6)$alkyl, $(C_1-C_6)$alkanoyl, aryl$(C_1-C_6)$alkyl, heteroaryl $(C_1-C_6)$alkyl, $(C_3-C_{12})$carbocycle, aryl, and heteroaryl; and each $R^g$ is independently selected from hydrogen, $(C_1-C_6)$alkyl, $(C_1-C_6)$alkanoyl, aryl$(C_1-C_6)$alkyl, heteroaryl$(C_1-C_6)$alkyl, $(C_3-C_{12})$carbocycle, aryl, and heteroaryl;

each $R_m$ is independently selected from cyano, halo, nitro, hydroxy, oxo, carboxy, aryl, heteroaryl, heterocycle, aryloxy, heteroaryloxy, heterocycleoxy, —$NR^eR^f$, —$S(O)_nR^g$, —$N(R^y)S(O)_nR^g$, —$S(O)_nNR^eR^f$, —$COOR^g$, and —$CONR^eR^f$; wherein each heterocycle of $R_m$ is optionally substituted with one or more groups independently selected from $(C_1-C_6)$alkyl, $(C_2-C_6)$alkenyl, $(C_2-C_6)$alkynyl, $(C_1-C_6)$alkoxy, $(C_3-C_{12})$carbocycle, cyano, halo, nitro, hydroxy, oxo, carboxy, aryloxy, heteroaryloxy, heterocycleoxy, —$NR^eR^f$, —$S(O)_nR^g$, —$N(R^y)S(O)_nR^g$, —$COOR^g$, and —$CONR^eR^f$; and wherein each aryl and heteroaryl of $R_m$ is optionally substituted with one or more groups independently selected from $(C_1-C_6)$alkyl, $(C_2-C_6)$alkenyl, $(C_2-C_6)$alkynyl, $(C_1-C_6)$alkoxy, $(C_3-C_{12})$carbocycle, cyano, halo, nitro, hydroxy, carboxy, $R_{m1}$, aryloxy, heteroaryloxy, heterocycleoxy, —$NR^eR^f$, —$S(O)_nR^g$, —$N(R^y)S(O)_nR^g$, —$S(O)_nNR^eR^f$, $(C_1-C_6)$alkoxy, —$COOR^g$, and —$CONR^eR^f$;

each $R_{m1}$ is independently selected from aryl and heteroaryl, wherein any aryl and heteroaryl of $R_{m1}$ is optionally substituted with one or more groups independently selected from $(C_1-C_6)$alkyl, $(C_2-C_6)$alkenyl, $(C_2-C_6)$alkynyl, $(C_1-C_6)$alkoxy, $(C_3-C_{12})$carbocycle, heterocycle, aryl, heteroaryl, cyano, halo, nitro, hydroxy, carboxy, —$NR^eR^f$, —$S(O)_nR^g$, —$N(R^y)S(O)_nR^g$, —$S(O)_nNR^eR^f$, $(C_1-C_6)$alkoxy, —$COOR^g$, and —$CONR^eR^f$;

each $R_n$ is independently selected from $(C_1-C_6)$alkyl, $(C_2-C_6)$alkenyl, $(C_2-C_6)$alkynyl, $(C_1-C_6)$alkoxy, $(C_3-C_{12})$carbocycle, aryl, heteroaryl, heterocycle, cyano, halo, nitro, hydroxy, carboxy, aryloxy, heteroaryloxy, heterocycleoxy, —$NR^eR^f$, —$S(O)_nR^g$, —$N(R^y)S(O)_nR^g$, —$S(O)_nNR^eR^f$, —$COOR^g$, and —$CONR^eR^f$; wherein each $(C_1-C_6)$alkyl, $(C_2-C_6)$alkenyl, $(C_2-C_6)$alkynyl, $(C_1-C_6)$alkoxy, heterocycle, and $(C_3-C_{12})$carbocycle of $R_n$ is optionally substituted with one or more groups independently selected from cyano, halo, nitro, hydroxy, carboxy, aryloxy, heteroaryloxy, heterocycleoxy, —$NR^eR^f$, —$S(O)_nR^g$, —$N(R^y)S(O)_nR^g$, —$COOR^g$, and —$CONR^eR^f$; wherein each aryl and heteroaryl of $R_n$ is optionally substituted with one or more groups independently selected from cyano, halo, nitro, hydroxy, oxo, carboxy, aryl, heteroaryl, aryloxy, heteroaryloxy, heterocycleoxy, —$NR^eR^f$, —$S(O)_nR^g$, —$N(R^y)S(O)_n R^g$, —$COOR^g$, —$S(O)_nNR^eR^f$, $(C_1-C_6)$alkoxy, and —$CONR^eR^f$;

each $R^y$ is independently selected from hydrogen and $(C_1-C_6)$alkyl; and n is 0, 1, or 2;

or a salt or prodrug thereof.

The invention also provides a pharmaceutical composition comprising a compound of formula I or a pharmaceutically acceptable salt thereof, and a pharmaceutically acceptable excipient.

The invention also provides a method to promote an antiviral effect in an animal (e.g., a human) comprising administering a compound of formula I, or a pharmaceutically salt thereof, to the animal.

The invention also provides a method to inhibit an endonuclease in an animal (e.g., a human) in need of such treatment comprising administering a compound of formula I, or a pharmaceutically salt thereof, to the animal.

The invention also provides a method to inhibit an exonuclease in an animal (e.g., a human) in need of such treatment comprising administering a compound of formula I, or a pharmaceutically salt thereof, to the animal.

The invention also provides a method to treat influenza in an animal (e.g., a human) comprising administering a compound of formula I, or a pharmaceutically salt thereof, to the animal.

The invention also provides a method to treat HIV in an animal (e.g., a human) comprising administering a compound of formula I, to the animal.

The invention also provides a method to inhibit DAAO in an animal comprising administering a compound of formula I to the animal.

The invention also provides a method to treat schizophrenia in an animal comprising administering a compound of formula I and D-serine to the animal.

The invention also provides a compound of formula I, or a pharmaceutically salt thereof for use in medical therapy.

The invention also provides a compound of formula I, or a pharmaceutically salt thereof for the prophylactic or therapeutic treatment of a viral infection.

The invention also provides a compound of formula I, or a pharmaceutically salt thereof for the prophylactic inhibition of an endonuclease.

The invention also provides a compound of formula I, or a pharmaceutically salt thereof for the prophylactic inhibition of an exonuclease.

The invention also provides a compound of formula I, or a pharmaceutically salt thereof for the prophylactic or therapeutic treatment of influenza.

The invention also provides a compound of formula I, or a pharmaceutically salt thereof for the prophylactic or therapeutic treatment of HIV.

The invention also provides a compound of formula I, or a pharmaceutically salt thereof for the prophylactic or therapeutic treatment of a disease or condition associated with DAAO activity.

The invention also provides a compound of formula I, or a pharmaceutically salt thereof for the prophylactic or therapeutic treatment of schizophrenia when administered with D-serine The invention also provides the use of a compound of formula I, or a pharmaceutically salt thereof to prepare a medicament for treating a viral infection in an animal (e.g., a human).

The invention also provides the use of a compound of formula I, or a pharmaceutically salt thereof to prepare a medicament for inhibiting an endonuclease in an animal (e.g., a human).

The invention also provides the use of a compound of formula I, or a pharmaceutically salt thereof to prepare a medicament for inhibiting an exonuclease in an animal (e.g., a human).

The invention also provides the use of a compound of formula I, or a pharmaceutically salt thereof to prepare a medicament for treating influenza in an animal (e.g., a human).

The invention also provides the use of a compound of formula I, or a pharmaceutically salt thereof to prepare a medicament for treating HIV in an animal (e.g., a human).

The invention also provides the use of a compound of formula I, or a pharmaceutically salt thereof to prepare a medicament for treating a disease or condition associated with DAAO activity.

The invention also provides the use of a compound of formula I, or a pharmaceutically salt thereof to prepare a medicament for treating schizophrenia (e.g. when administered with D-serine).

The invention also provides processes and intermediates disclosed herein that are useful for preparing a compound of formula I or a salt thereof.

DETAILED DESCRIPTION

Figure 1:
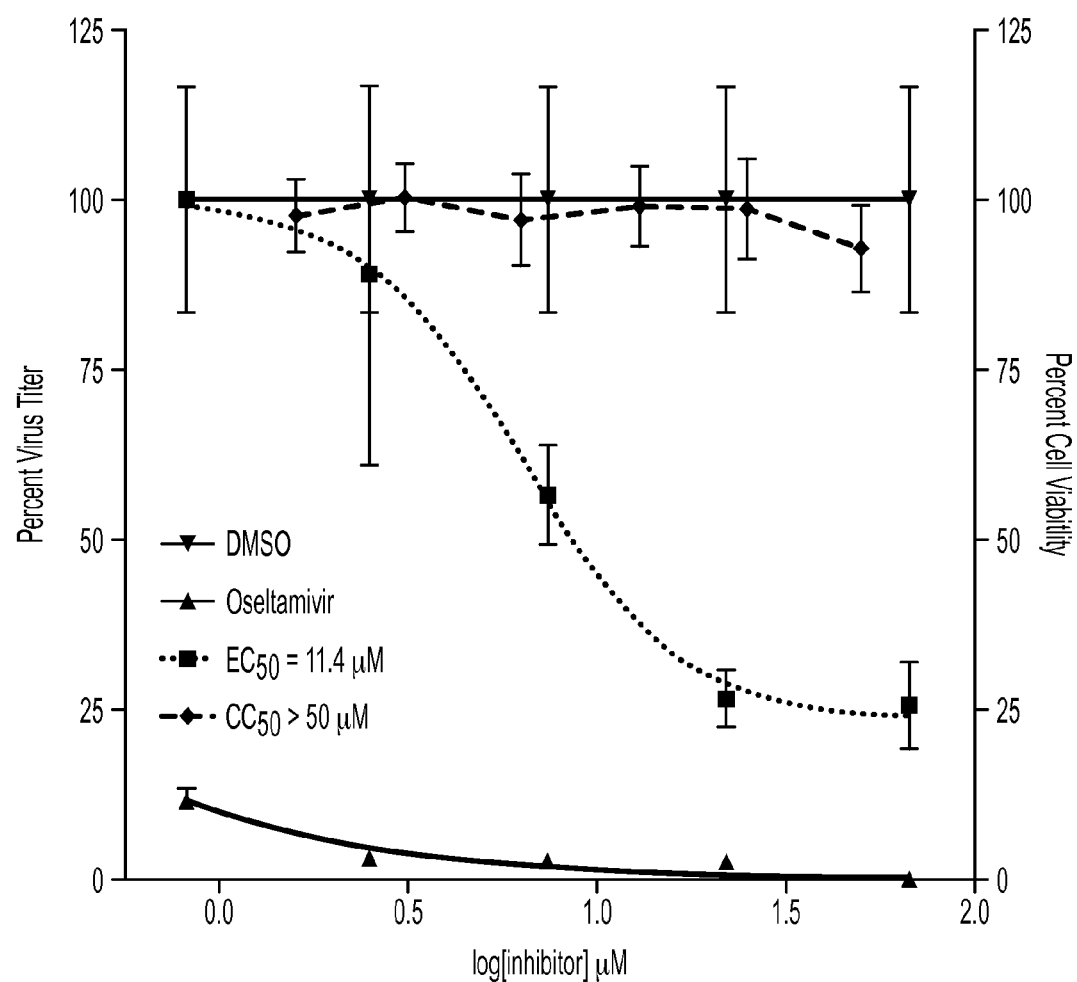
FIG. 1 illustrates data generated from Example 63.
Figure 2:
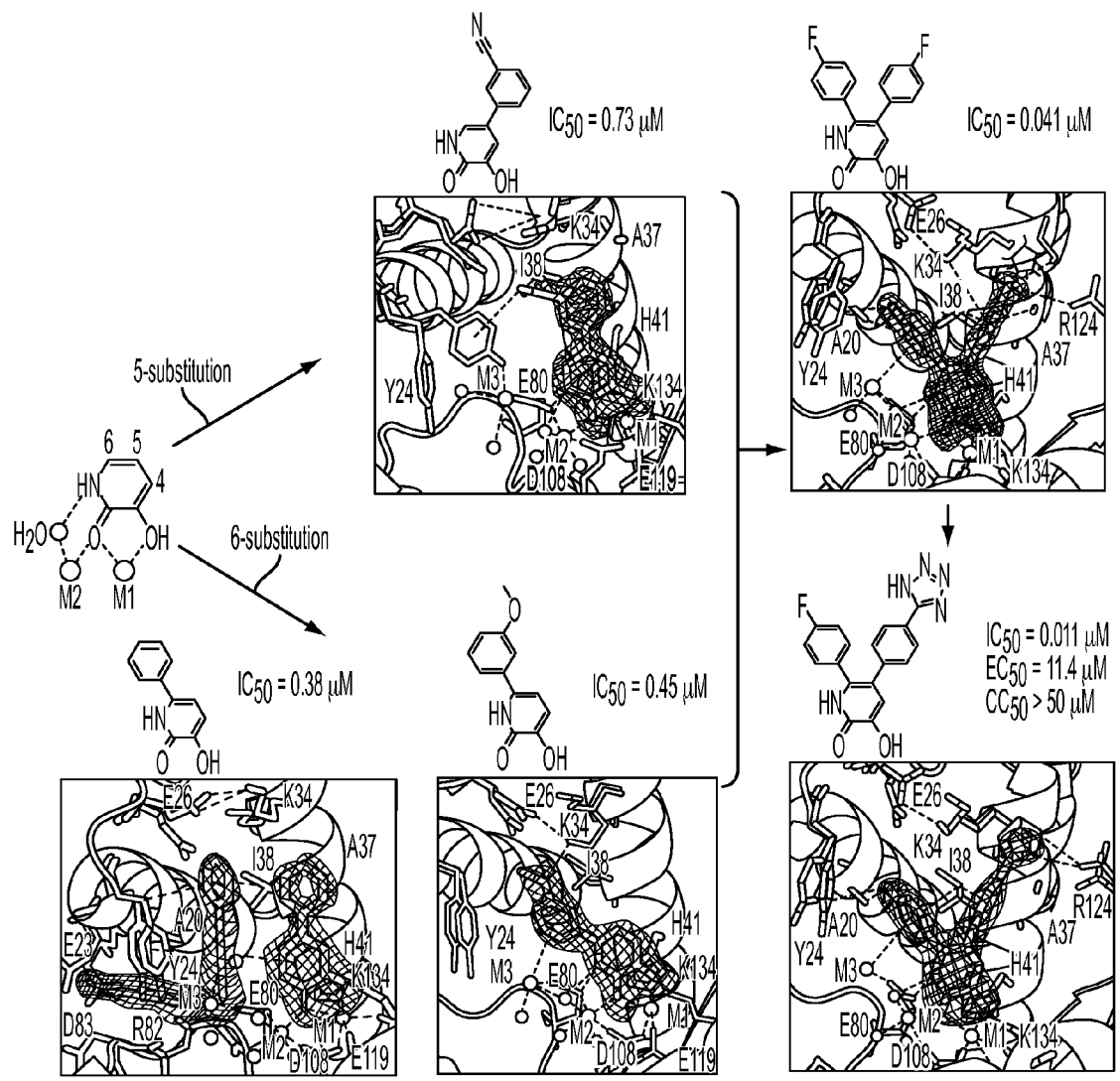
FIG. 2 illustrates 3D SAR for representative pyridinone compounds from Example 61. Metal coordinating and hydrogen bonds are depicted as black dashes, hydrophobic and cation-π interactions are grey. Residues with significant structural changes upon binding of a ligand are shown with the apo structure colored light grey.

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

The term "heterocycle" as used herein refers to a single saturated or partially unsaturated ring or a multiple condensed ring system. The term includes single saturated or partially unsaturated rings (e.g. 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g. 1, 2 or 3) oxo groups and the sulfur and nitrogen atoms may also be present in their oxidized forms. Such rings include but are not limited to azetidinyl, tetrahydrofuranyl or piperidinyl. The term "heterocycle" also includes multiple condensed ring systems (e.g. ring systems comprising 2, 3 or 4 rings) wherein a single heterocycle ring (as defined above) can be condensed with one or more heterocycles (e.g. decahydronapthyridinyl), carbocycles (e.g. decahydroquinolyl) or aryls. The rings of the multiple condensed ring system can be connected to each other via fused, spiro and bridged bonds when allowed by valency requirements. It is to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g. a nitrogen). Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl and 1,4-benzodioxanyl.

The term "$(C_3-C_{12})$carbocycle" refers to a single saturated (i.e., cycloalkyl) or a single partially unsaturated (e.g., cycloalkenyl, cycloalkadienyl, etc.) ring having 3 to 7 carbon atoms (i.e. $(C_3-C_7)$carbocycle). The term "carbocycle" or "carbocyclyl" also includes multiple condensed ring systems (e.g. ring systems comprising 2, 3 or 4 carbocyclic rings). Accordingly, carbocycle includes multicyclic carbocyles such as a bicyclic carbocycles (e.g. bicyclic carbocycles having about 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocycles can be connected to each other via a single carbon atom to form a spiro connection (e.g. spiropentane, spiro[4,5]decane, etc), via two adjacent carbon atoms to form a fused connection (e.g. carbocycles such as decahydronaphthalene, norsabinane, norcarane) or via two non-adjacent carbon atoms to form a bridged connection (e.g. norbornane, bicyclo[2.2.2] octane, etc). The "carbocycle" or "carbocyclyl" can also be optionally substituted with one or more (e.g. 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

The term "prodrug" as used herein refers to a compound that when administered to a biological system (e.g. a mammal such as a human) generates the drug substance, i.e. active ingredient, as a result of spontaneous chemical reaction(s), enzyme catalyzed chemical reaction(s), photolysis, and/or metabolic chemical reaction(s) or by some other process. A prodrug is thus a modified (e.g. covalently modified) analog or latent form of a therapeutically-active compound. A prodrug may also be an active metabolite or therapeutically-active compound itself. By way of example a prodrug may generate the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191; Tranoy-Opalinski, I., Fernandes, A., Thomas, M., Gesson, J.-P., and Papot, S., Anti-Cancer Agents in Med. Chem., 8 (2008) 618-637). Enzymes which are capable of an enzymatic activation mechanism with the prodrug compounds of the invention include, but are not limited to nitroreductase, proteases (e.g. serine proteases such as prostate specific antigen (PSA), amidases, esterases, microbial enzymes, phospholipases, cholinesterases, and phosphases).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond is drawn in a non-stereochemical manner (e.g. flat) the atom to which the bond is attached includes all stereochemical possibilities. It is also to be understood that when a bond is drawn in a stereochemical manner (e.g. bold, bold-wedge, dashed or dashed-wedge) the atom to which the stereochemical bond is attached has the stereochemistry as shown unless otherwise noted.

Accordingly, in one embodiment, a compound of the invention may be greater than 50% a single enantiomer. In another embodiment, a compound of the invention may be at least 51% a single enantiomer. In another embodiment, a compound of the invention may be at least 60% a single enantiomer. In another embodiment, a compound of the invention may be at least 70% a single enantiomer. In another embodiment, a compound of the invention may be at least 80% a single enantiomer. In another embodiment, a compound of the invention may be at least 90% a single enantiomer. In another embodiment, a compound of the invention may be at least 95% a single enantiomer. In another embodiment, a compound of the invention may be at least 98% a single enantiomer. In another embodiment, a compound of the invention may be at least 99% a single enantiomer. In another embodiment, a compound of the invention may be greater than 50% a single diastereomer. In another embodiment, a compound of the invention may be at least 51% a single diastereomer. In another embodiment, a compound of the invention may be at least 60% a single diastereomer. In another embodiment, a compound of the invention may be at least 70% a single diastereomer. In another embodiment, a compound of the invention may be at least 80% a single diastereomer. In another embodiment, a compound of the invention may be at least 90% a single diastereomer. In another embodiment, the compounds of the invention are at least 95% a single diastereomer. In another embodiment, a compound of the invention may be at least 98% a single diastereomer. In another embodiment, a compound of the invention may be at least 99% a single diastereomer.

It will be appreciated by those skilled in the art that compounds of formula I can also exist in various tautomeric forms (illustrated below).

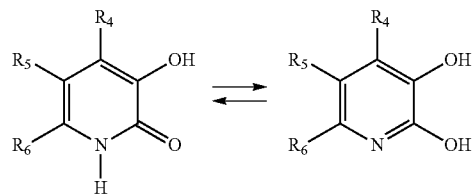

-continued

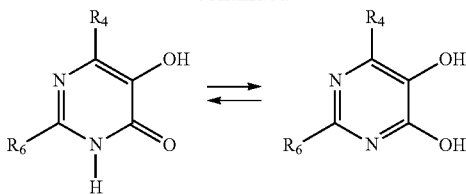

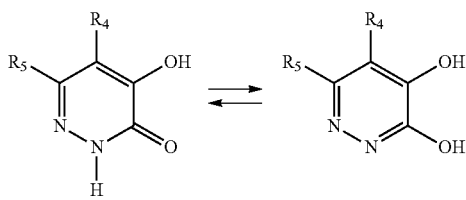

It is to be understood that the present invention encompasses all tautomeric forms of a compound of formula I as well as mixtures thereof, which possess the useful properties described herein.

Specific values listed below for radicals, substituents, and ranges, are for illustration only; they do not exclude other defined values or other values within defined ranges for the radicals and substituents. The specific listed below are values for compounds of formula I and all subformulas of formula I (e.g., compounds of formulas Ia, Ib and Ic). It is understood that two or more specific values may be combined together.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazolyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific group of compounds are compounds of formula Ia:

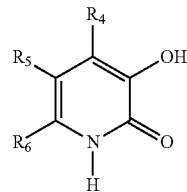

or salts thereof.

A specific group of compounds are compounds of formula Ib:

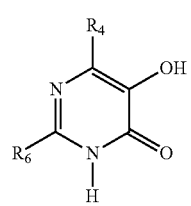

or salts thereof.

A specific group of compounds are compounds of formula Ic:

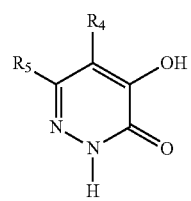

or salts thereof.

A specific group of compounds are compounds wherein $X^1$ is $CR_5$ and $X^2$ is $CR_6$.

A specific group of compounds are compounds wherein $X^1$ is N and $X^2$ is $CR_6$; or $X^1$ is $CR_5$ and $X^2$ is N.

A specific group of compounds I are compounds wherein $X^1$ is N and $X^2$ is $CR_6$.

A specific group of compounds are compounds wherein $X^1$ is $CR_5$ and $X^2$ is N.

A specific value for $R_4$ is H, fluoro, chloro, trifluoromethyl, or methyl.

A specific value for $R_4$ is H.

A specific value for $R_4$ is fluoro.

A specific value for $R_4$ is H, fluoro, chloro, trifluoromethyl, methyl or aryl, wherein any aryl of $R_4$ is optionally substituted with one or more groups independently selected from $R_n$.

A specific value for $R_n$ is halo.

A specific value for $R_4$ is H, fluoro, chloro, trifluoromethyl, methyl or phenyl, wherein phenyl is optionally substituted with one or more halo.

A specific value for $R_4$ is H or phenyl, wherein phenyl is optionally substituted with one or more halo.

A specific value for $R_4$ is H or 4-fluorophenyl.

A specific value for $R_4$ is methyl.

A specific value for $R_5$ is H, halo, $(C_1-C_6)$alkyl, $(C_3-C_{12})$carbocycle, $-NR^aR^b$, or aryl, wherein each $(C_1-C_6)$alkyl and $(C_3-C_{12})$carbocycle is optionally substituted with one or more groups independently selected from $R_m$; and wherein any aryl is optionally substituted with one or more groups independently selected from $R_n$.

A specific value for $R_5$ is H, halo or aryl, wherein any aryl of $R_5$ is optionally substituted with one or more groups independently selected from $R_n$.

A specific value for $R_5$ is H, halo or phenyl, wherein phenyl is optionally substituted with one or more groups independently selected from $R_n$.

A specific value for $R_n$ is independently selected from heteroaryl, halo, nitro, and $-CONR^eR^f$; wherein each aryl and heteroaryl of $R_n$ is optionally substituted with one or more groups independently selected from cyano, halo, nitro, hydroxy, oxo, carboxy, aryl, heteroaryl, aryloxy, heteroaryloxy, heterocycleoxy, $-NR^eR^f$, $-S(O)_nR^g$, $-N(R^y)S(O)_nR^g$, $-COOR^g$, $-S(O)_nNR^eR^f$, $(C_1-C_6)$alkoxy, and $-CONR^eR^f$.

A specific value for each $R_n$ is independently selected from heteroaryl, cyano, halo, nitro, and $-CONR^eR^f$.

A specific value for $R_5$ is H, methyl, 4-tetrazol-5-ylphenyl, cyclohexyl, 3-tetrazol-5-ylphenyl, 3-carboxyphenyl, 4-carboxyphenyl, 4-cyanophenylamino, 3-cyanophenyl, 3-carboxyphenyl, benzyl, 3-fluorophenyl, bromo, phenyl, 4-fluorophenyl, 3-aminocarbonylphenyl, 4-aminocarbonylphenyl, 4-nitrophenyl, or 4-cyanophenyl.

A specific value for $R_5$ is H, 3-fluorophenyl, bromo, phenyl, 4-fluorophenyl, 3-aminocarbonylphenyl, 4-aminocarbonylphenyl, or 4-nitrophenyl 4-cyanophenyl or 4-tetrazol-2-ylphenyl A specific value for $R_5$ is H, methyl, 3-fluorophenyl, bromo, phenyl, 4-fluorophenyl, 3-aminocarbonylphenyl, 4-aminocarbonylphenyl, or 4-nitrophenyl.

A specific value for $R_5$ is phenyl, benzyl, 2-pyridyl, 3-pyridyl, or 4-pyridyl wherein the phenyl or pyridyl is optionally substituted with one or more groups selected from the group consisting of $-COOH$, $-CONR^eR^f$, $-SO_3H$, $-SO_2NHCH_3$, OH, $OCH_3$, F, Cl, Br, $CH_3$; or wherein $R_5$ is methyl substituted with COOH, $SO_3H$, $SO_2NHCH_3$, OH, a $CF_3$ or a tetrazole.

A specific value for RP is H, halo, $(C_1-C_6)$alkyl, $(C_3-C_{12})$carbocycle or aryl, wherein each $(C_1-C_6)$alkyl and $(C_3-C_{12})$carbocycle is optionally substituted with one or more groups independently selected from $R_m$; and wherein any aryl is optionally substituted with one or more groups independently selected from $R_n$.

A specific value for $R_6$ is H, halo, $(C_3-C_{12})$carbocycle or aryl, wherein any aryl of $R_6$ is optionally substituted with one or more groups independently selected from $R_n$.

A specific value for $R_6$ is H, halo, cyclohexyl, cyclohexenyl, or phenyl, wherein any cyclohexyl, cyclohexenyl, or phenyl of $R_6$ is optionally substituted with one or more groups independently selected from $R_n$.

A specific value for each $R_n$ is independently selected from $(C_1-C_6)$alkyl $(C_1-C_6)$alkoxy, heteroaryl, cyano, halo, nitro, hydroxy, and $-CONR^eR^f$; wherein each $(C_1-C_6)$alkyl and $(C_1-C_6)$alkoxy of $R_n$ is optionally substituted with one or more groups independently selected from cyano, halo, nitro, hydroxy, carboxy, aryloxy, heteroaryloxy, heterocycleoxy, $-NR^eR^f$, $-S(O)_nR^g$, $-N(R^y)S(O)_nR^g$, $-COOR^g$, and $-CONR^eR^f$; wherein each heteroaryl of $R_n$ is optionally substituted with one or more groups independently selected from cyano, halo, nitro, hydroxy, oxo, carboxy, aryl, heteroaryl, aryloxy, heteroaryloxy, heterocycleoxy, $-NR^eR^f$, $-S(O)_nR^g$, $-N(R^y)S(O)_nR^g$, $-COOR^g$, $-S(O)_nNR^eR^f$, $(C_1-C_6)$alkoxy, and $-CONR^eR^f$.

A specific value for each $R_n$ is independently selected from $(C_1-C_6)$alkyl $(C_1-C_6)$alkoxy, heteroaryl, cyano, halo, nitro, hydroxy, and $-CONR^eR^f$; wherein each $(C_1-C_6)$alkyl of $R_n$ is optionally substituted with one or more halo.

A specific value for $R_6$ is H, bromo, phenyl, 4-tert-butylphenyl, 4-trifluoromethylphenyl, 4-fluorophenyl, 4-methoxyphenyl, 3-methoxyphenyl, 3-fluorophenyl, cyclohex-1-en-1-yl, cyclohexyl, 3,4-dihydroxyphenyl, 4-nitrophenyl, 3-aminocarbonylphenyl, 4-aminocarbonylphenyl, 4-cyanophenyl, 3-cyanophenyl, 3-tetrazol-5-ylphenyl, 3-carboxyphenyl, 4-phenylbenzyl, or 4-tetrazol-5-ylphenyl.

A specific value for $R_6$ is H, bromo, phenyl, 4-tert-butylphenyl, 4-trifluoromethylphenyl, 4-fluorophenyl, 4-methoxyphenyl, 3-methoxyphenyl, 3-fluorophenyl, cyclohex-1-en-1-yl, cyclohexyl, 3,4-dihydroxyphenyl, 4-nitrophenyl, 3-aminocarbonylphenyl, 4-aminocarbonylphenyl, 4-cyanophenyl, 3-cyanophenyl, 3-tetrazol-2-ylphenyl or 4-tetrazol-2-ylphenyl.

A specific value for $R_6$ is H, bromo, phenyl, 4-tert-butylphenyl, 4-trifluoromethylphenyl, 4-fluorophenyl, 3-methoxyphenyl, 3-fluorophenyl, cyclohex-1-en-1-yl, 3,4-dihydroxyphenyl, 4-cyclohexylphenyl, 4-nitrophenyl, 3-aminocarbonylphenyl, or 4-aminocarbonylphenyl.

A specific value for $R_6$ is phenyl or benzyl, which phenyl or benzyl is optionally substituted with one or more substituents selected from the group consisting of F, Cl, Br, $OCH_3$, $CH_3$, and $CONR^eR^f$.

A specific compound is a compound wherein:
$R_4$ is H;
$R_5$ is H, halo or aryl wherein each aryl of $R_5$ is optionally substituted with one or more groups independently selected from $R_n$; and
$R_6$ is $(C_3-C_{12})$carbocycle or aryl, wherein each $(C_3-C_{12})$carbocycle of $R_6$ is optionally substituted with one or more groups independently selected from $R_m$; and wherein each aryl of $R_6$ is optionally substituted with one or more groups independently selected from $R_n$.

A specific compound is a compound wherein:
$R_4$ is H;
$R_5$ is H, halo or phenyl wherein each phenyl of $R_5$ is optionally substituted with one or more groups independently selected from $R_n$; and
$R_6$ is $(C_6)$carbocycle or phenyl, wherein each $(C_6)$carbocycle of $R_6$ is optionally substituted with one or more groups independently selected from $R_m$; and wherein each phenyl of $R_6$ is optionally substituted with one or more groups independently selected from $R_n$.

A specific compound is a compound wherein:
$R_5$ is H, halo, cyano, nitro, $(C_1-C_6)$alkyl, $(C_2-C_6)$alkenyl, $(C_2-C_6)$alkynyl, $(C_1-C_6)$alkoxy, $(C_3-C_{12})$carbocycle, aryl, heteroaryl, heterocycle, $-NR^aR^b$, $-S(O)_nR^c$, $-N(R^y)S(O)_n$ $R^c$, $-S(O)_nNR^aR^b$, $-COOR^c$, or $-CONR^aR^b$, wherein each $(C_1-C_6)$alkyl, $(C_2-C_6)$alkenyl, $(C_2-C_6)$alkynyl, $(C_1-C_6)$alkoxy, $(C_3-C_{12})$carbocycle of $R_4$ is optionally substituted with one or more groups independently selected from $R_m$; and wherein each aryl and heteroaryl, of $R_4$ is optionally substituted with one or more groups independently selected from $R_n$; and
$R_6$ is bromo, $(C_1-C_6)$alkyl, $(C_2-C_6)$alkenyl, $(C_2-C_6)$alkynyl, $(C_1-C_6)$alkoxy, $(C_3-C_{12})$carbocycle, aryl, heteroaryl, heterocycle, $-NR^aR^b$, $-S(O)_nR^c$, $-N(R^y)S(O)_nR^c$, $-S(O)_nNR^aR^b$, $-COOR^c$, or $-CONR^aR^b$, wherein each $(C_1-C_6)$alkyl, $(C_2-C_6)$alkenyl, $(C_2-C_6)$alkynyl, $(C_2-C_6)$alkoxy, and $(C_3-C_{12})$carbocycle of $R_4$ is optionally substituted with one or more groups independently selected from $R_m$; and wherein each aryl and heteroaryl, of $R_4$ is optionally substituted with one or more groups independently selected from $R_n$.

A specific compound is a compound wherein:

$R_5$ is $(C_1-C_3)$alkyl, aryl, heteroaryl, wherein each $(C_1-C_3)$ alkyl of $R_5$ is optionally substituted with one or more groups independently selected from $R_m$; and wherein each aryl and heteroaryl of $R_5$ is optionally substituted with one or more groups independently selected from $R_n$; and $R_6$ is bromo, $(C_1-C_3)$alkyl, $(C_3-C_8)$carbocycle, aryl, heteroaryl, wherein each $(C_1-C_6)$alkyl, $(C_3-C_{12})$carbocycle of $R_6$ is optionally substituted with one or more groups independently selected from $R_m$; and wherein each aryl and heteroaryl, of $R_6$ is optionally substituted with one or more groups independently selected from $R_n$.

A specific compound is:

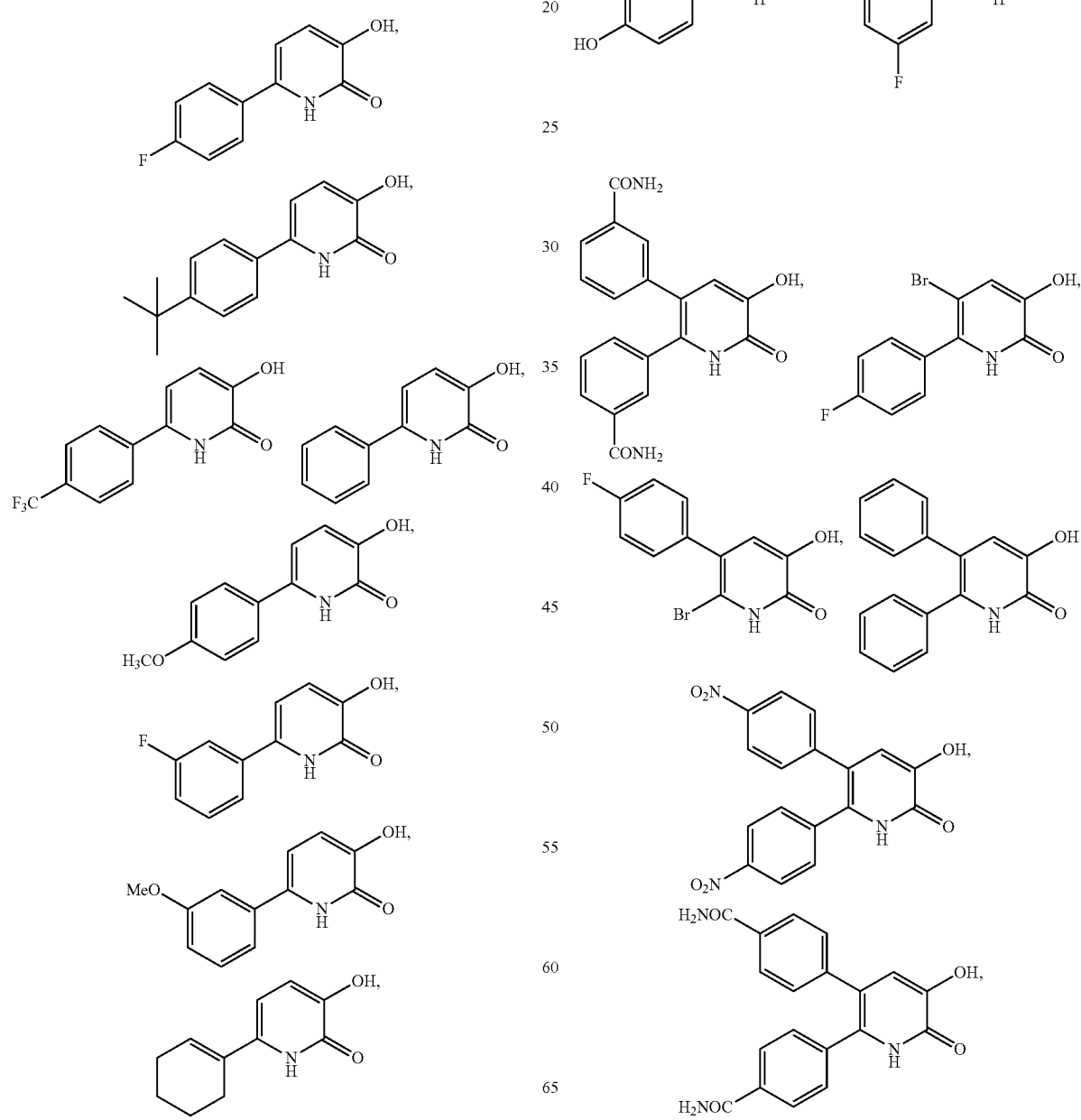

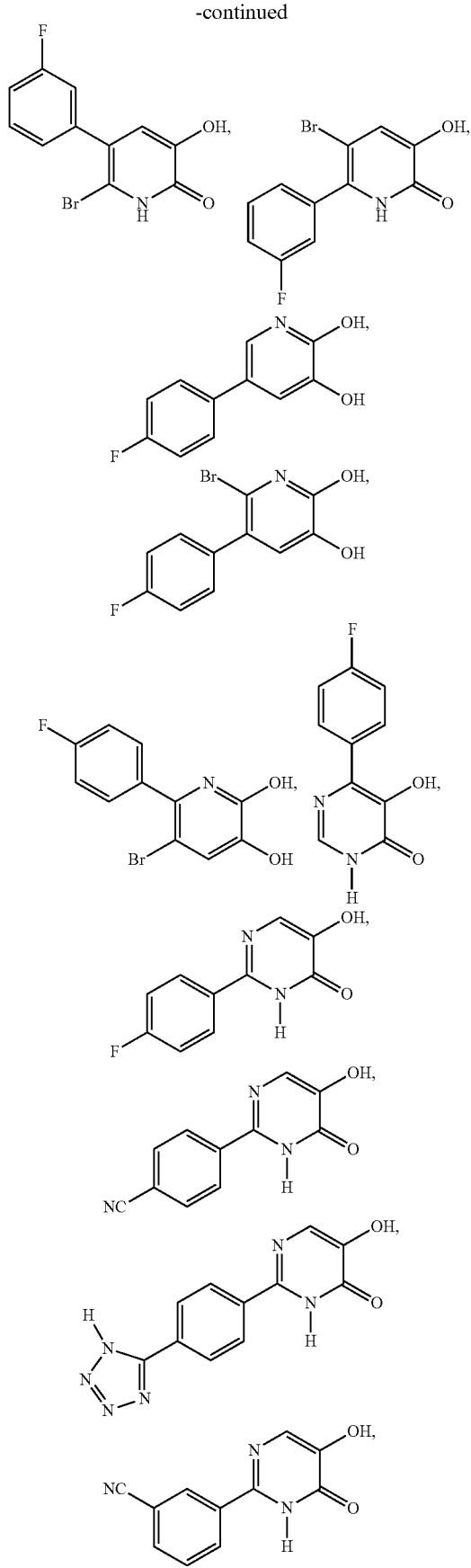
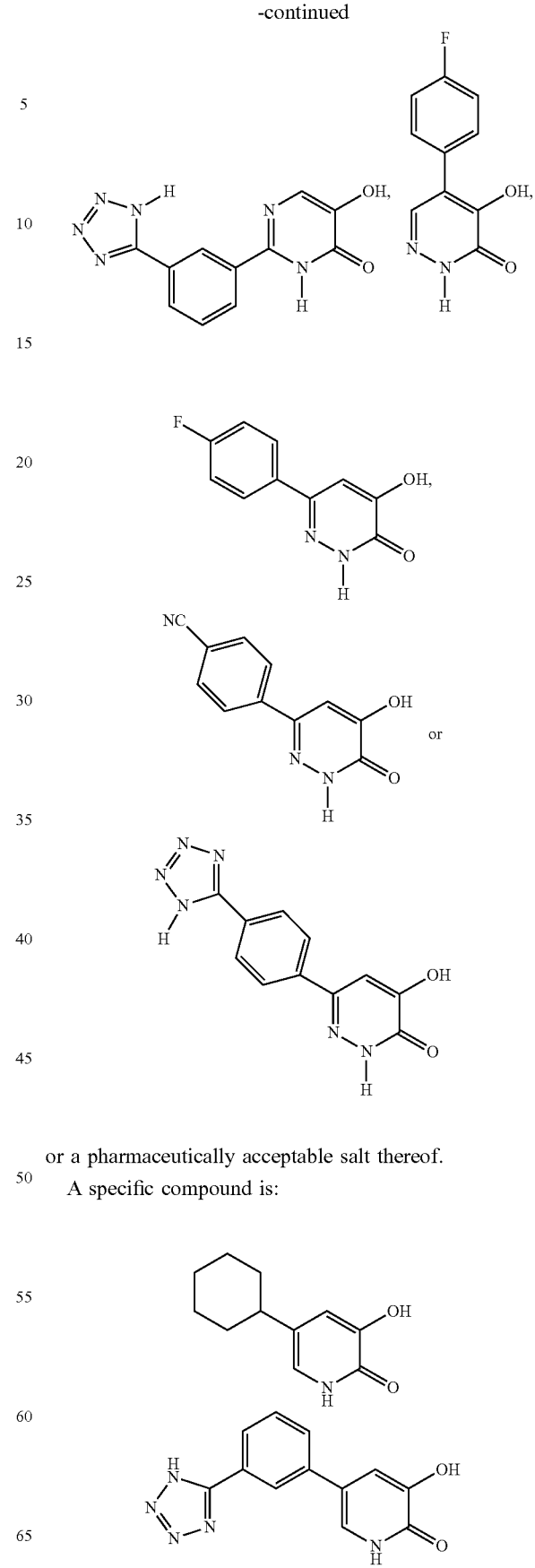
or a pharmaceutically acceptable salt thereof.
A specific compound is:
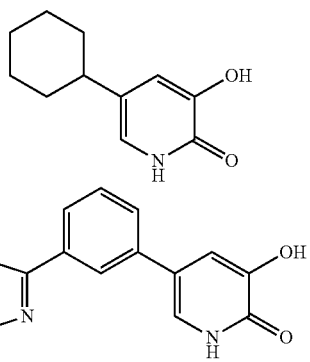

-continued
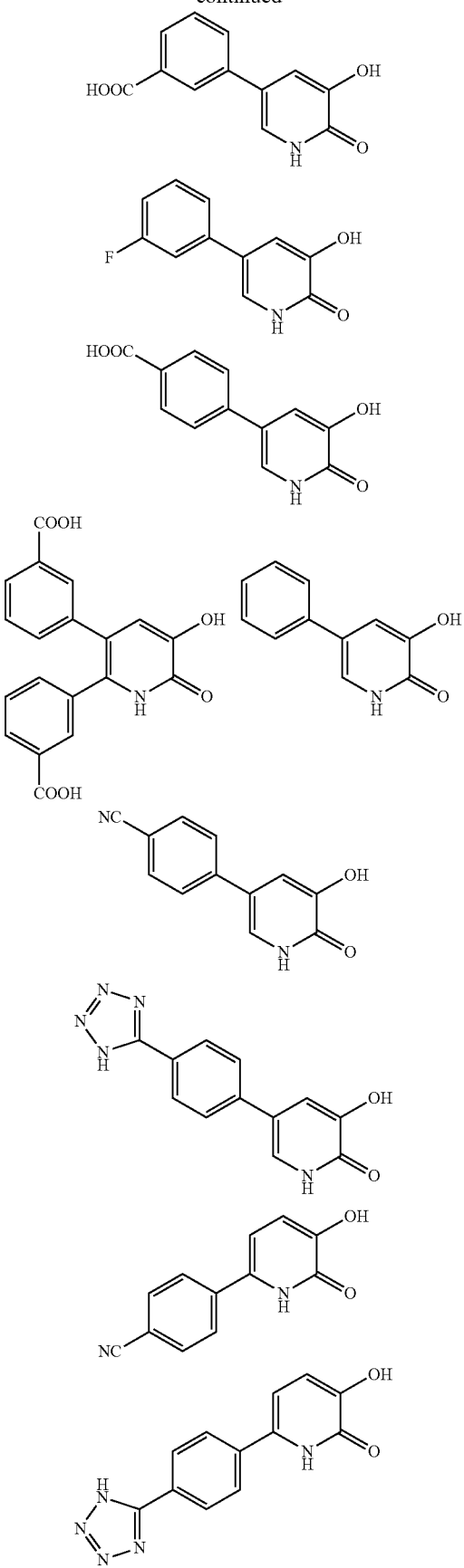
-continued
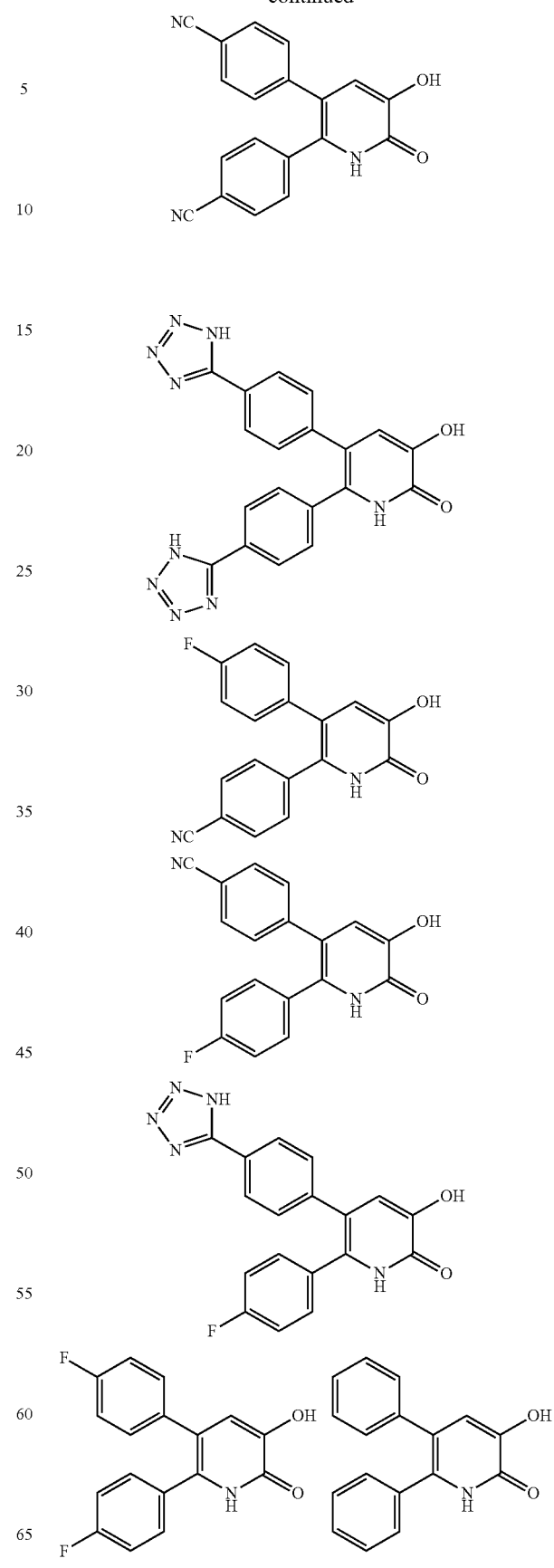

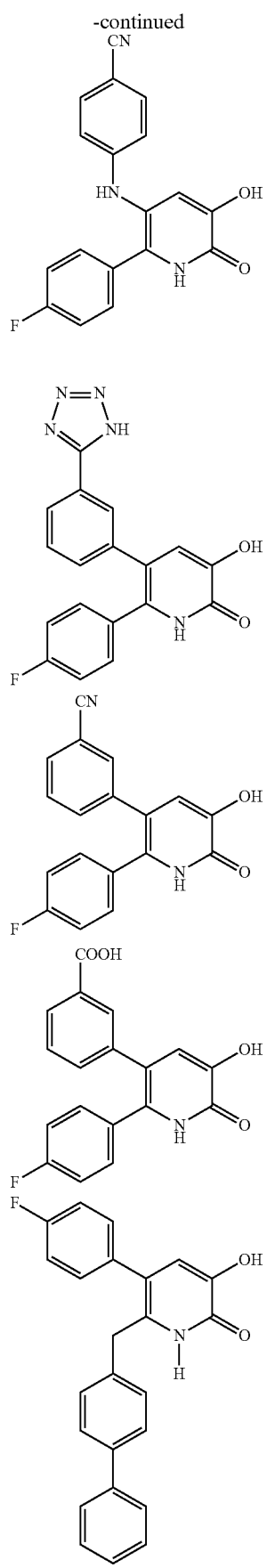

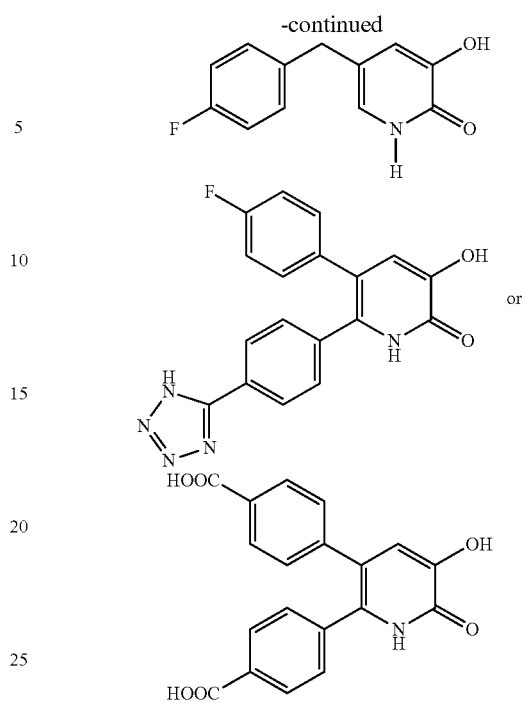

or a pharmaceutically acceptable salt thereof.

A specific group of compounds are compounds of formula Ia:

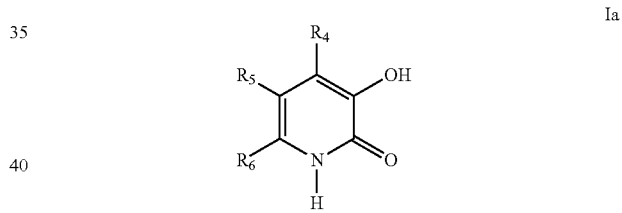

wherein:

$R_4$ is H, halo, cyano, nitro, $(C_1-C_6)$alkyl, $(C_2-C_6)$alkenyl, $(C_2-C_6)$alkynyl, $(C_1-C_6)$alkoxy, $(C_3-C_{12})$carbocycle, aryl, heteroaryl, heterocycle, —NR$^a$R$^b$, —S(O)$_n$R$^c$, —S(O)$_n$NR$^a$R$^b$, —N(R$^y$)S(O)$_n$R$^c$, —COOR$^c$, or —CONR$^a$R$^b$, wherein each $(C_1-C_6)$alkyl, $(C_2-C_6)$alkenyl, $(C_2-C_6)$alkynyl, $(C_1-C_6)$alkoxy, $(C_3-C_{12})$carbocycle of $R_4$ is optionally substituted with one or more groups independently selected from $R_m$; and wherein each aryl, heterocycle, and heteroaryl of $R_4$ is optionally substituted with one or more groups independently selected from $R_n$;

$R_5$ is H, halo, cyano, nitro, $(C_1-C_6)$alkyl, $(C_2-C_6)$alkenyl, $(C_2-C_6)$alkynyl, $(C_1-C_6)$alkoxy, $(C_3-C_{12})$carbocycle, aryl, heteroaryl, heterocycle, —NR$^a$R$^b$, —S(O)$_n$R$^c$, —N(R$^y$)S(O)$_n$ R$^c$, —S(O)$_n$NR$^a$R$^b$, —COOR$^c$, or —CONR$^a$R$^b$, wherein each $(C_1-C_6)$alkyl, $(C_2-C_6)$alkenyl, $(C_2-C_6)$alkynyl, $(C_1-C_6)$alkoxy, $(C_3-C_{12})$carbocycle of $R_5$ is optionally substituted with one or more groups independently selected from $R_m$; and wherein each aryl, heterocycle, and heteroaryl of $R_5$ is optionally substituted with one or more groups independently selected from $R_n$;

$R_6$ is H, halo, cyano, nitro, $(C_1-C_6)$alkyl, $(C_2-C_6)$alkenyl, $(C_2-C_6)$alkynyl, $(C_1-C_6)$alkoxy, $(C_3-C_{12})$carbocycle, aryl, heteroaryl, heterocycle, —NR$^a$R$^b$, —S(O)$_n$R$^c$, —N(R$^y$)S(O)$_n$R$^c$, —S(O)$_n$NR$^a$R$^b$, —COOR$^c$, or —CONR$^a$R$^b$, wherein each (C$_1$-C$_6$)alkyl, (C$_2$-C$_6$)alkenyl, (C$_2$-C$_6$)alkynyl, (C$_1$-C$_6$)alkoxy, (C$_3$-C$_{12}$)carbocycle of R$_6$ is optionally substituted with one or more groups independently selected from R$_m$; and wherein each aryl, heterocycle, and heteroaryl of R$_6$ is optionally substituted with one or more groups independently selected from R$_n$;

each R$^a$ and R$^b$ is independently selected from hydrogen, (C$_1$-C$_6$)alkyl, (C$_1$-C$_6$)alkanoyl, aryl(C$_1$-C$_6$)alkyl, heteroaryl (C$_1$-C$_6$)alkyl, (C$_3$-C$_{12}$)carbocycle, aryl, and heteroaryl, wherein each (C$_1$-C$_6$)alkyl, (C$_1$-C$_6$)alkanoyl, and (C$_3$-C$_{12}$) carbocycle of R$^a$ and R$^b$ is optionally substituted with one or more groups independently selected from R$_m$; and wherein each aryl and heteroaryl of R$^a$ and R$^b$ is optionally substituted with one or more groups independently selected from R$_n$;

each R$^c$ is independently selected from hydrogen, hydroxy, (C$_1$-C$_6$)alkyl, (C$_1$-C$_6$)alkanoyl, aryl(C$_1$-C$_6$)alkyl, heteroaryl(C$_1$-C$_6$)alkyl, (C$_3$-C$_{12}$)carbocycle, aryl, and heteroaryl, wherein each (C$_1$-C$_6$)alkyl, (C$_1$-C$_6$)alkanoyl, and (C$_3$-C$_{12}$)carbocycle of R$^c$ is optionally substituted with one or more groups independently selected from R$_m$; and wherein each aryl and heteroaryl of R$^c$ is optionally substituted with one or more groups independently selected from R$_n$;

each R$^e$ and R$^f$ is independently selected from hydrogen, (C$_1$-C$_6$)alkyl, (C$_1$-C$_6$)alkanoyl, aryl(C$_1$-C$_6$)alkyl, heteroaryl (C$_1$-C$_6$)alkyl, (C$_3$-C$_{12}$)carbocycle, aryl, and heteroaryl; and each R$^g$ is independently selected from hydrogen, (C$_1$-C$_6$)alkyl, (C$_1$-C$_6$)alkanoyl, aryl(C$_1$-C$_6$)alkyl, heteroaryl(C$_1$-C$_6$)alkyl, (C$_3$-C$_{12}$)carbocycle, aryl, and heteroaryl;

each R$_m$ is independently selected from cyano, halo, nitro, hydroxy, oxo, carboxy, aryl, heteroaryl, heterocycle, aryloxy, heteroaryloxy, heterocycleoxy, —NR$^e$R$^f$, —S(O)$_n$R$^g$, —N(R$^y$)S(O)$_n$R$^g$, —S(O)$_n$NR$^e$R$^f$, —COOR$^g$, and —CONR$^e$R$^f$; wherein each heterocycle of R$_m$ is optionally substituted with one or more groups independently selected from (C$_1$-C$_6$)alkyl, (C$_2$-C$_6$)alkenyl, (C$_2$-C$_6$)alkynyl, (C$_1$-C$_6$) alkoxy, (C$_3$-C$_{12}$)carbocycle, cyano, halo, nitro, hydroxy, oxo, carboxy, aryloxy, heteroaryloxy, heterocycleoxy, —NR$^e$R$^f$, —S(O)$_n$R$^g$, —N(R$^y$)S(O)$_n$R$^g$, —COOR$^g$, and —CONR$^e$R$^f$; wherein each aryl and heteroaryl of R$_m$ is optionally substituted with one or more groups independently selected from cyano, halo, nitro, hydroxy, carboxy, aryl, heteroaryl, aryloxy, heteroaryloxy, heterocycleoxy, —NR$^e$R$^f$, —S(O)$_n$R$^g$, —N(R$^y$)S(O)$_n$R$^g$, —S(O)$_n$NR$^e$R$^f$, (C$_1$-C$_6$)alkoxy, —COOR$^g$, and —CONR$^e$R$^f$;

each R$_n$ is independently selected from (C$_1$-C$_6$)alkyl, (C$_2$-C$_6$)alkenyl, (C$_2$-C$_6$)alkynyl, (C$_1$-C$_6$)alkoxy, (C$_3$-C$_{12}$) carbocycle, aryl, heteroaryl, heterocycle, cyano, halo, nitro, hydroxy, carboxy, aryloxy, heteroaryloxy, heterocycleoxy, —NR$^e$R$^f$, —S(O)$_n$R$^g$, —N(R$^y$)S(O)$_n$R$^g$, —S(O)$_n$NR$^e$R$^f$, —COOR$^g$, and —CONR$^e$R$^f$; wherein each (C$_1$-C$_6$)alkyl, (C$_2$-C$_6$)alkenyl, (C$_2$-C$_6$)alkynyl, (C$_1$-C$_6$)alkoxy, heterocycle, and (C$_3$-C$_{12}$)carbocycle of R$_n$ is optionally substituted with one or more groups independently selected from cyano, halo, nitro, hydroxy, carboxy, aryloxy, heteroaryloxy, heterocycleoxy, —NR$^e$R$^f$, —S(O)$_n$R$^g$, —N(R$^y$)S(O)$_n$R$^g$, —COOR$^g$, and —CONR$^e$R$^f$; wherein each aryl and heteroaryl of R$_n$ is optionally substituted with one or more groups independently selected from cyano, halo, nitro, hydroxy, oxo, carboxy, aryl, heteroaryl, aryloxy, heteroaryloxy, heterocycleoxy, —NR$^e$R$^f$, —S(O)$_n$R$^g$, —N(R$^y$)S(O)$_n$R$^g$, —COOR$^g$, —S(O)$_n$NR$^e$R$^f$, (C$_1$-C$_6$)alkoxy, and —CONR$^e$R$^f$;

each R$^y$ is independently selected from hydrogen and (C$_1$-C$_6$)alkyl; and n is 0, 1, or 2;

or a salt thereof.

In one embodiment the compound of formula I is not 5-chloro-3-hydroxypyridin-2(1H)-one, 5-bromo-3-hydroxypyridin-2(1H)-one, or 3-hydroxy-5-methylpyridin-2(1H)-one.

In one embodiment the compound of formula I is not a compound of the following formula:

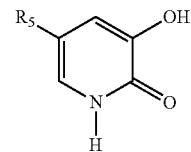

wherein R$_5$ is bromo, phenethyl, hydrogen, chloro, or methyl.

In one embodiment the compound of formula I is not a compound of the following formula:

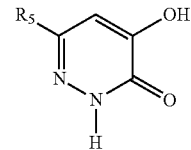

wherein R$_5$ is phenethyl, alpha-methylbenzyl, 3-phenylpropyl, 4-chlorophenethyl, 2-(4-chlorophenyl)ethenyl, 3,3-dimethylbytyl, phenoxymethyl, 2-fluorophenethyl, 3-fluorophenethyl, 3-methoxyphenethyl, 4-fluorophenethyl, 4-methoxyphenethyl, 3,5-difluorophenethyl, or 3,5-dimethoxyphenethyl.

Processes for preparing compounds of formula I are provided as further embodiments of the invention and are illustrated in the following Schemes wherein the meanings of the generic radicals are as given above unless otherwise qualified.

Scheme 1
General Methods for the Preparation of 4-Substituted 2,3-Dihydroxypyridines

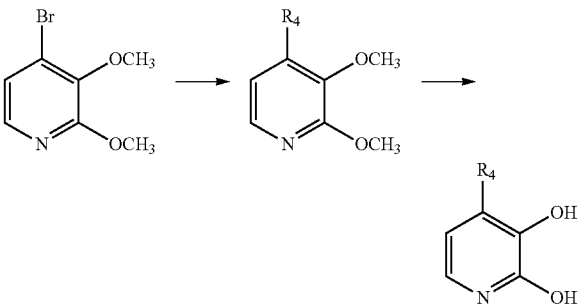

Scheme 2 General Methods for the Preparation of 5-Substituted 6-Bromo-2,3-Dihydroxypyridines and 6-Substituted 5-Bromo-2,3-dihydroxypyridines -continued

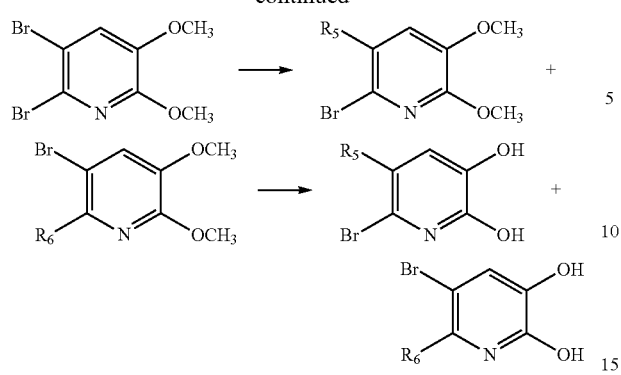

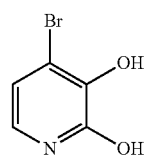

Preparation of 5,6-Dibromo-2,3-methoxypyridine

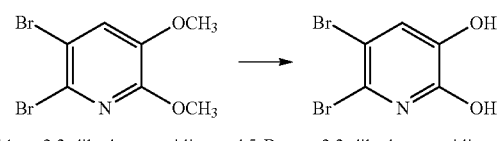

5-Chloro-2,3-dihydroxypyridine and 5-Bromo-2,3-dihydroxypyridine (Commercially Available)

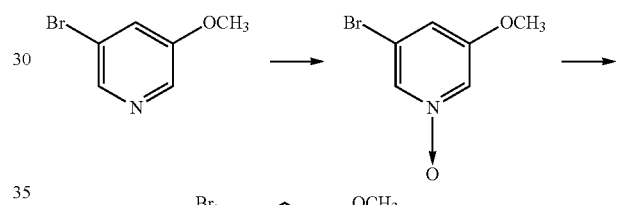

Preparation of 5-Bromo-2-ethoxy-3-methoxypyridine

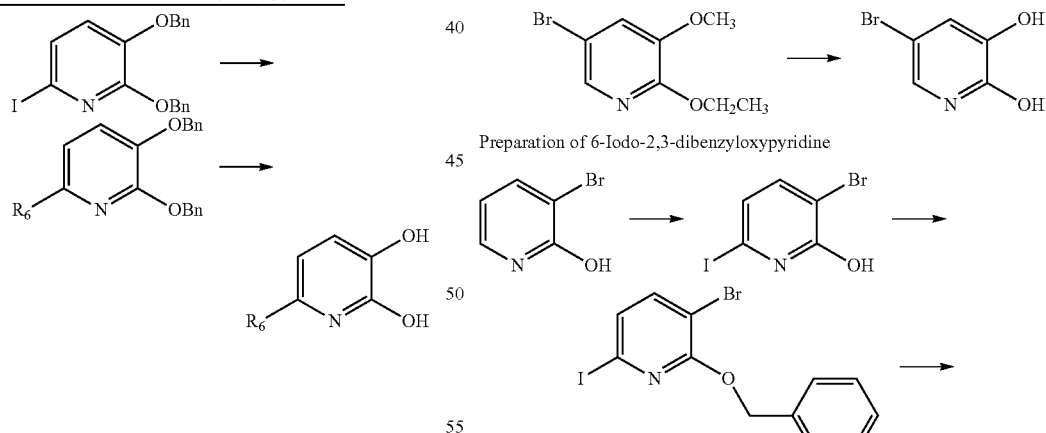

Preparation of 6-Iodo-2,3-dibenzyloxypyridine

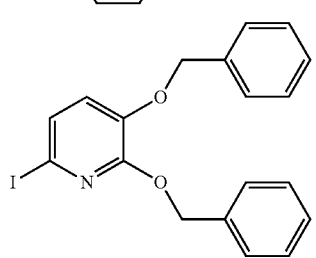

Scheme 3 General Methods for the Preparation of 5-Substituted 2,3-Dihydroxypyridines

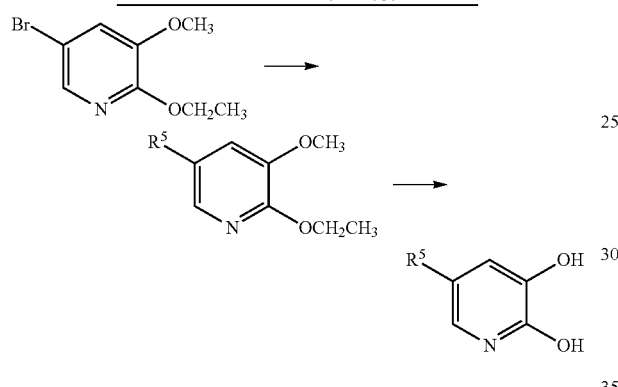

Scheme 4 General Methods for the Preparation of 6-Substituted 2,3-Dihydroxypyridines Scheme 5
General Methods for the Preparation of Halogenated 2,3-Dihydroxypyridines and Their Ether Derivatives Preparation of 4-Bromo-2,3-methoxypyridine

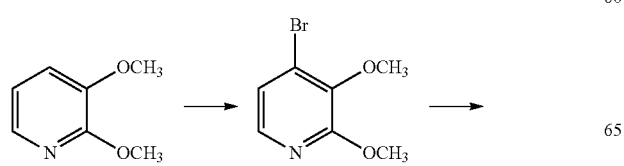

Scheme 6 General Methods for the Preparation of 4- and 6-Aminomethyl Substituted and 4,6-bis-(Aminomethyl) Substitited 2,3-Dihydroxypyridines
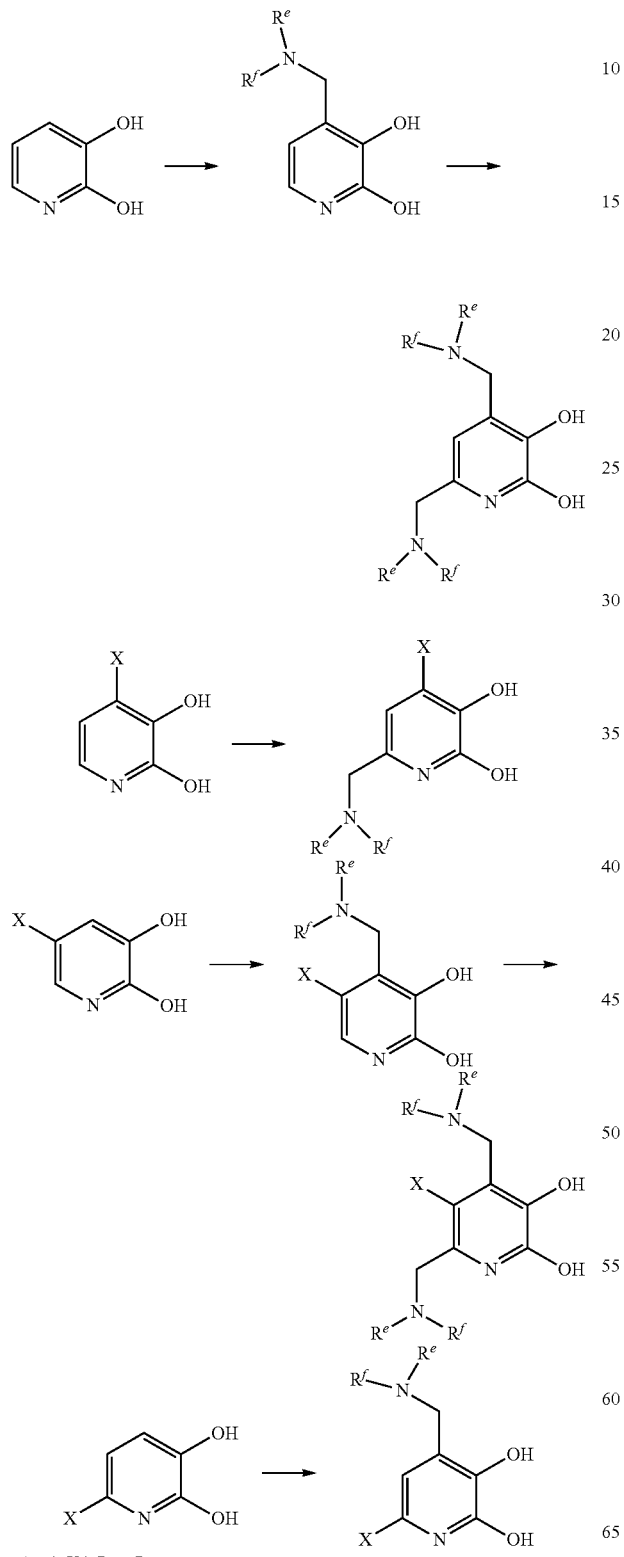
wherein X is $R_5$ or $R_6$
The above scheme can also be used to prepare compounds of formula I wherein the group $NR_eR_f$ is replaced with an N-linked heterocycle.
Scheme 7a Sequential Formation of 5-Then 6-Substituted 3-Hydroxypyridones
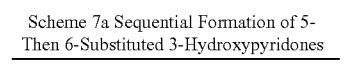
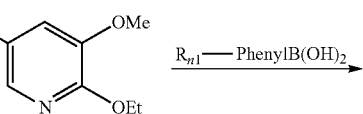
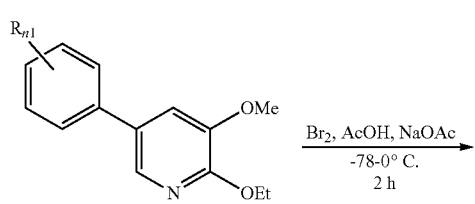
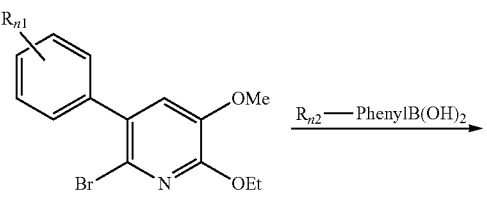
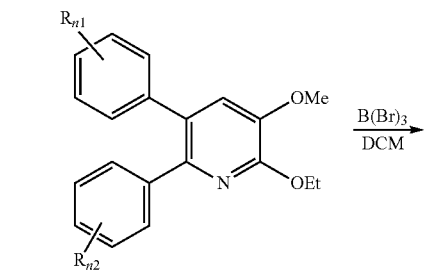
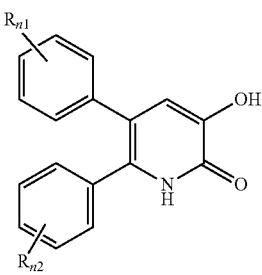

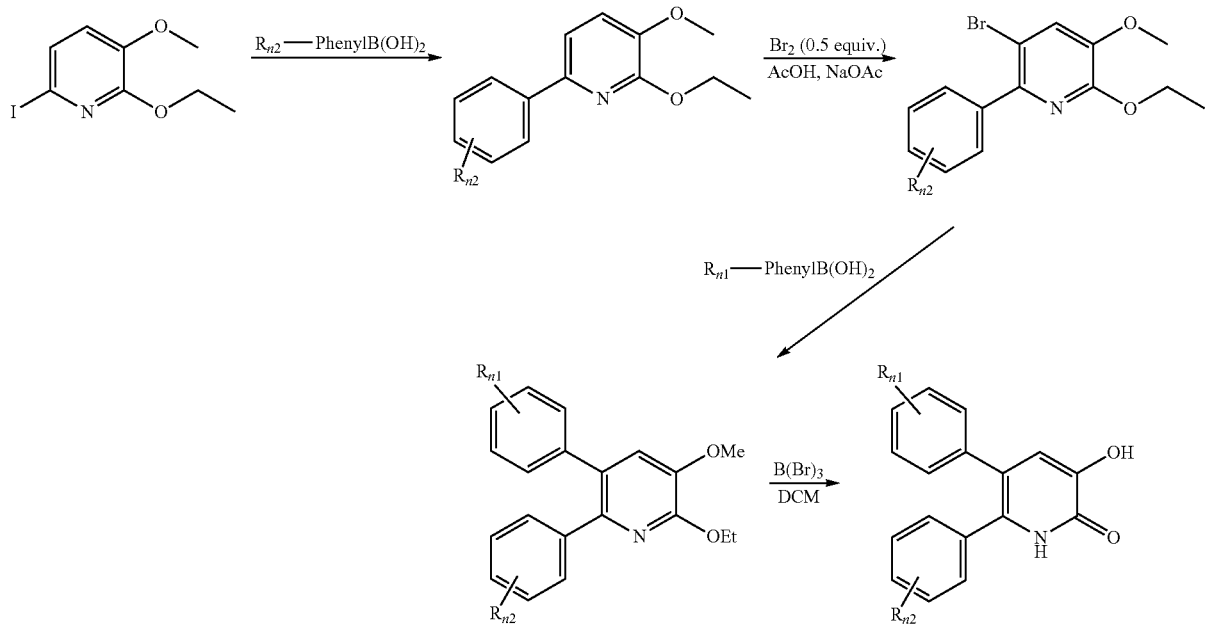
In Schemes 7a and 7b, the groups $R_{n1}$ and $R_{n2}$ are each independently selected from the values for Rn described herein.
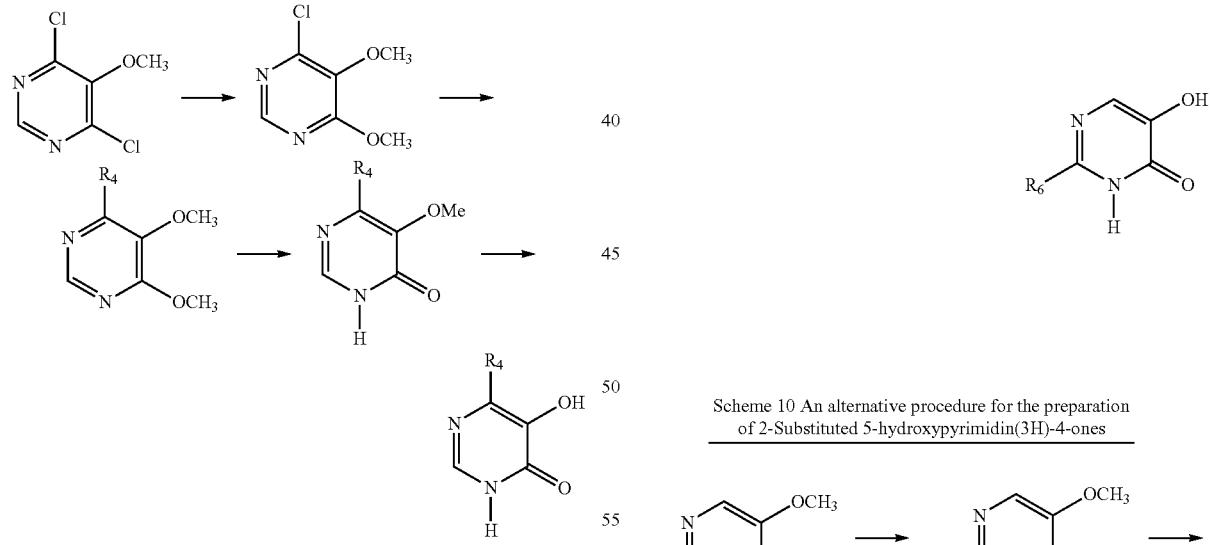
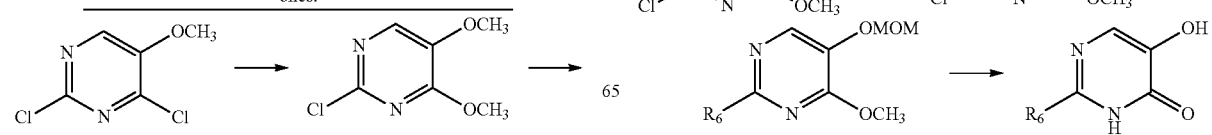

Scheme 11 General synthetic approach for the preparation of 5-Substituted 4-hydroxypyridazin-3(2H)-ones

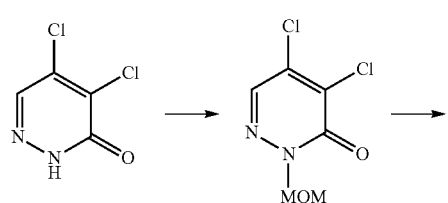

Scheme 13 Synthesis of Substituted 6-Phenyl-5-Hydroxypyrimidin4(3H)-ones

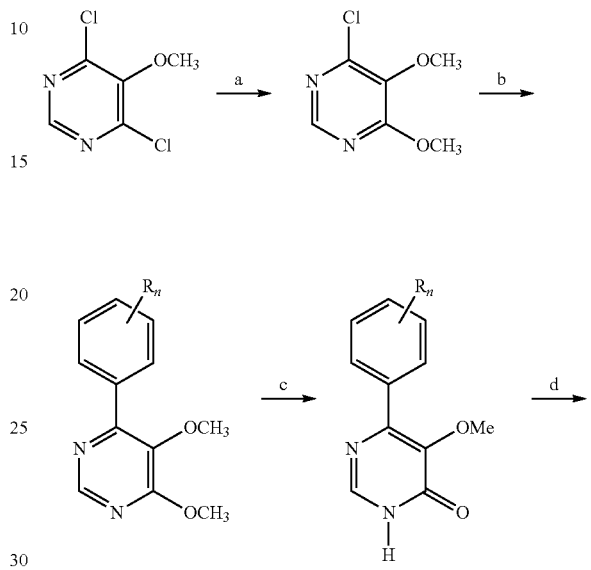

Reagents and conditions:
(a) NaOMe (1.1 mol equiv), MeOH under Ar;
(b) substituted (Rn) phenylboronic acid, Pd(PPh$_3$)$_4$, Na$_2$CO$_3$, dioxane/H$_2$O (3:1) under Ar;
(c) dioxane/2N HCl (1:1) under Ar;
(d) BBr$_3$ in CH$_2$Cl$_2$, 0° C to r.t. under Ar.

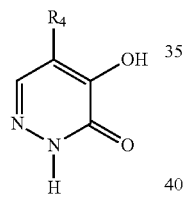

Scheme 12 General synthetic approach for the preparation of 6-Substituted 4-hydroxypyridazin-3(2H)-ones

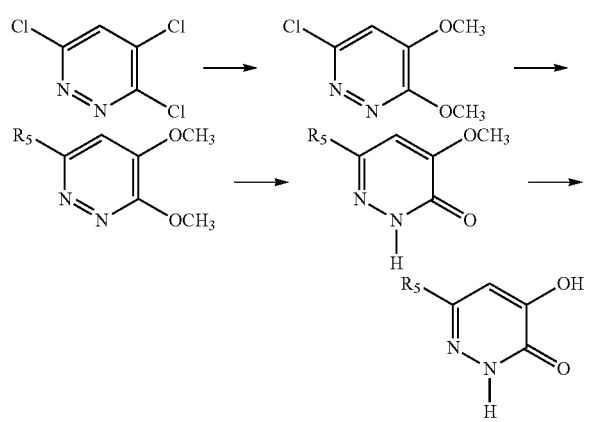

Scheme 14
Preparation of Substituted 2-Phenyl 5-Hydroxypyrimidin(3H)-4-ones

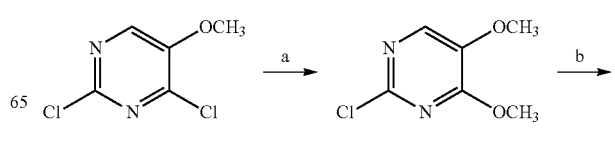

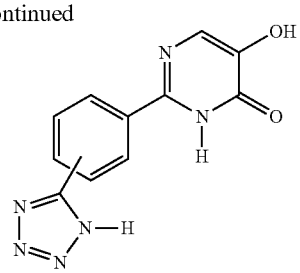

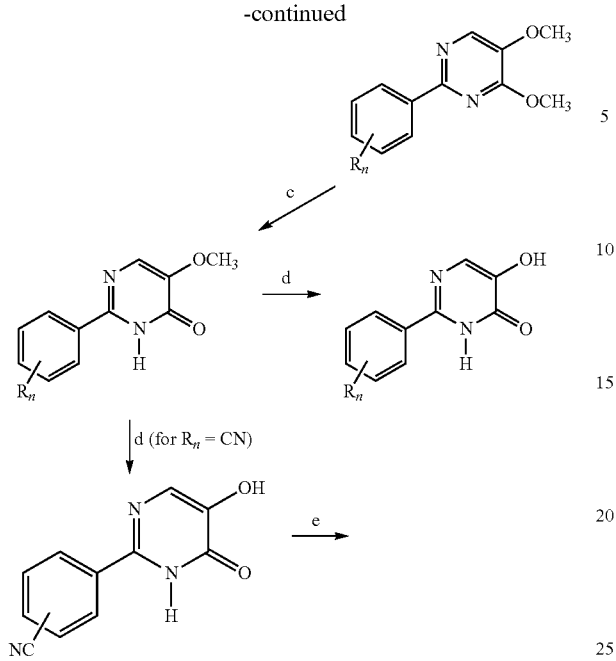

Reagents and conditions:
(a) K$_2$CO$_3$ (10 mol equiv), MeOH under Ar;
(b) substituted (R$_n$) phenylboronic acid (e.g., p-cyanophenylboronic acid and m-cyanophenylboronic acid) Pd(PPh$_3$)$_4$, Na$_2$CO$_3$, dioxane/H$_2$O (3:1), under Ar;
(c) dioxane/2N HCl (1:1) under Ar;
(d) BBr$_3$ in CH$_2$Cl$_2$, 0° C. to r.t. under Ar;
(e) NaN$_3$ (4.0 mol equiv), AcOH, DMF under Ar.

Scheme 15 Preparation of Substituted 2-Phenyl 5-Hydroxypyrimidin(3H)-4-ones.

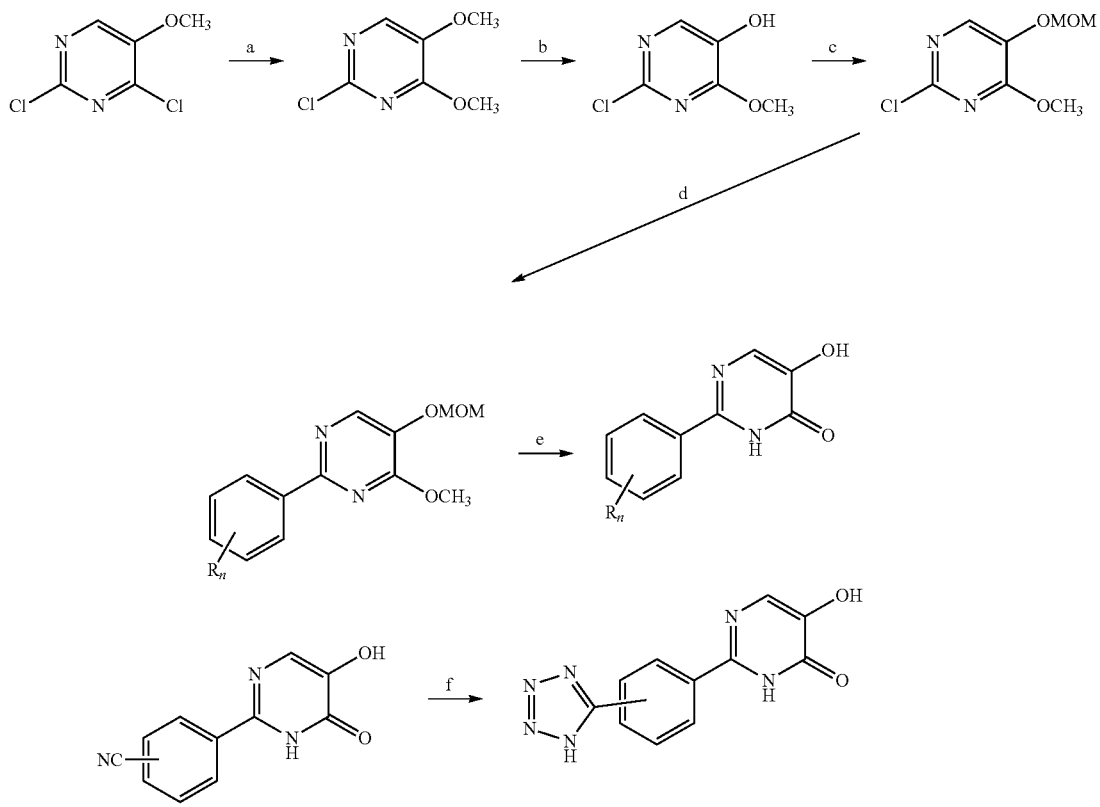

Reagents and conditions:
(a) K$_2$CO$_3$ (10 mol equiv), MeOH under Ar;
(b) dioxane/2N HCl (1:1) under Ar;
(c) MOMCl (1.2 mol equiv), DMAP (0.1 mol equiv);
(d) substituted (R$_n$) phenylboronic acid Pd(PPh$_3$)$_4$, Na$_2$CO$_3$, dioxane/H$_2$O (3:1), under Ar;;
(e) BBr$_3$ in CH$_2$Cl$_2$, 0° C. to r.t. under Ar;
(f) NaN$_3$ (4.0 mol equiv), AcOH, DMF under Ar.

Scheme 16 Synthesis of various Substituted 6-Phenyl 4-Hydroxypyridazin(2H)-3-ones.

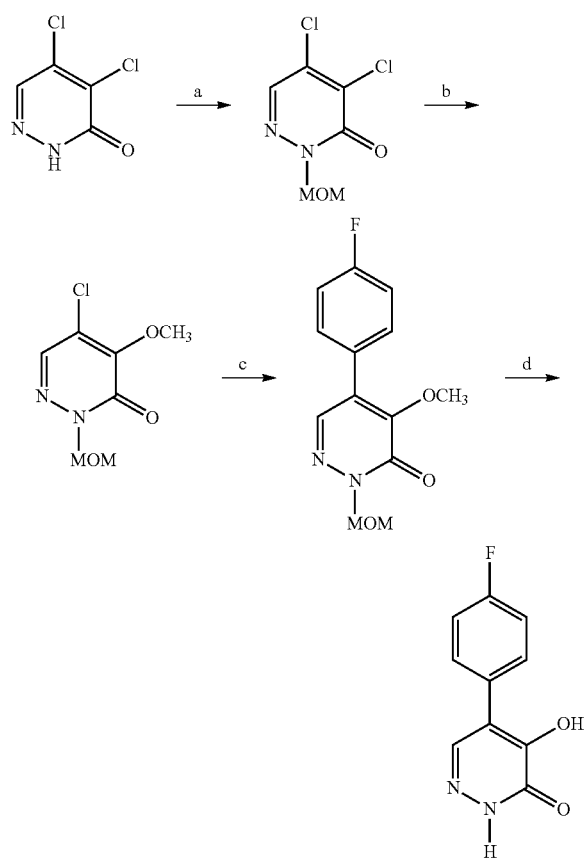

Reagents and conditions:
(a) MOMCl (1.2 mol equiv), DMAP (0.1 mol equiv), NEt$_3$ (1.4 mol equiv), CH$_2$Cl$_2$, 0° C. to r.t. under Ar;
(b) NaOMe (1.1 mol equiv), MeOH under Ar;
(c) substituted phenylboronic acid, Pd(PPh$_3$)$_4$, Na$_2$CO$_3$, dioxane/H$_2$O (3:1) under Ar;
(d) BBr$_3$ in CH$_2$Cl$_2$, 0° C. to r.t. under Ar.

Scheme 17 Synthesis of Various Substituted 5-Phenyl 4-Hydroxypyridazin(2H)-3-ones

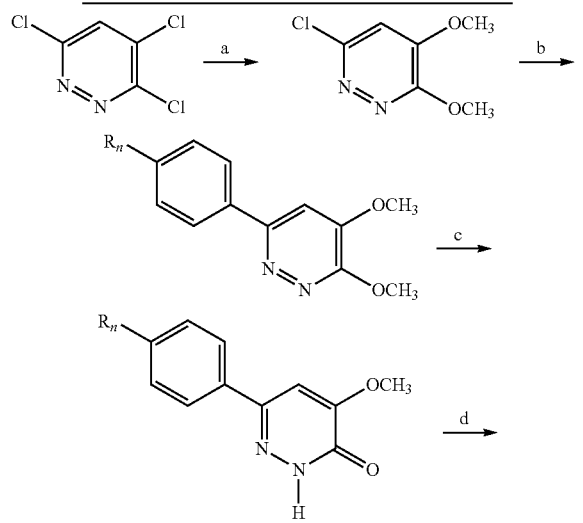

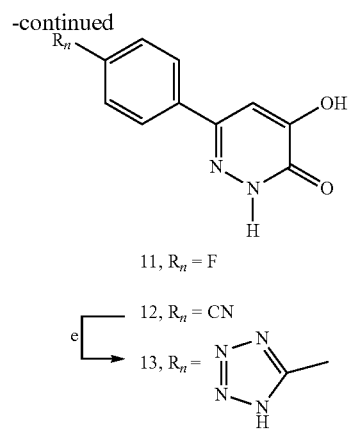

11, $R_n$ = F

12, $R_n$ = CN

13, $R_n$ = [tetrazole]

Reagents and conditions:
(a) NaOMe (2 mol equiv), MeOH under Ar;
(b) substituted phenylboronic acid Pd(PPh$_3$)$_4$, Na$_2$CO$_3$, dioxane/H$_2$O (3:1) under Ar;
(c) dioxane/2N HCl (1:1) under Ar;
(d) BBr$_3$ in CH$_2$Cl$_2$, 0° C. to r.t. under Ar;
(e) NaN$_3$ (4.0 mol equiv), AcOH, DMF, under Ar.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to an avian or a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

The compounds can also be administered by inhalation, for example, by oral or nasal inhalation and can be formulated accordingly.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds of the invention are useful for inhibiting endonucleases as well as for inhibiting exonucleases and polynucleotidyl transferases. Thus, the compounds of the invention are useful for treating conditions associated with endonuclease or exonucleases activity, and in particular, conditions wherein inhibition of endonuclease or exonucleases activity is indicated. Additionally, in one embodiment, the invention provides a method to treat a viral infection. Viral infections treatable with compounds of the invention include viruses of the Orthomyxoviridae family (e.g. influenza A, influenza B and influenza C), and viruses of the Arenaviridae and Bunyaviridae families of viruses (e.g. Hantavirus). In one specific embodiment the compounds of the invention are useful for treating viruses associated with "influenza A cap snatching endonucleases." In another specific embodiment the compounds of the invention are useful as anti-HIV integrase and RNase H agents;

thus, they are also useful for treating pathological conditions associated with such enzymes.

The invention will now be illustrated by the following non-limiting Examples.

EXAMPLES

Example 1

Preparation of Compound

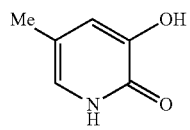

To a solution of 5-methyl-2-ethoxy-3-methoxypyridine (110 mg, 0.72 mmol) stirred in $CH_2Cl_2$ (3.0 ml) under nitrogen, was added boron tribromide (1M solution in $CH_2Cl_2$) (1.0 ml). After addition was completed, the reaction mixture was stirred for 16 hours at room temperature. Dichloromethane was removed under vacuum and aq.HCl (3N) was added. The resulting solid was filtered and then redissolved in $CH_2Cl_2$ and washed with $NaHCO_3$ and brine, dried and evaporated under reduced pressure to afford a tan solid (65 mg, 72% yield). $^1$H NMR (300 MHz, MeOD-$d_4$) δ:6.75 (s, 1H), 6.7 (s, 1H), 1.99 (s, 3H).

The intermediates were prepared as follows.

a. Preparation of Compound

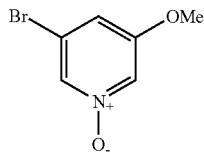

A solution of 3-(methoxy)-5-bromopyridine (2.0 g, 10.6 mmol.) and meta-chloroperbenzoic acid (mCPBA; 2.5 g, 14.8 mmol) in dichloromethane (50 ml) was stirred at room temperature for 3 hours. The reaction mixture was washed with 15 mL 2N KOH followed by brine. The organic layers were dried over anhydrous $MgSO_4$ and concentrated in vacuo to give product as white solid (1.06 g, 51%).

b. Preparation of Compound

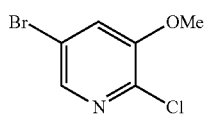

Phosphoryl chloride ($POCl_3$) (4.8 mL, 52.9 mmol) was added to a solution of 5-bromo-3-methoxy-pyridine oxide (540 mg, 2.6 mmol) in 15 ml $CH_2Cl_2$. The reaction mixture was stirred at room temperature overnight. The reaction mixture was washed with sat. sodium bicarbonate and brine. The organic layer was dried, concentrated and purified using ISCO flash chromatography using 50% ethyl acetate in hexane to provide 369 mg product (62% yield). $^1$H NMR (300 MHz, CDCl$_3$) δ: 8.05 (s, 1H), 7.34 (s, 1H), 3.93 (s, 3H).

c. Preparation of Compound

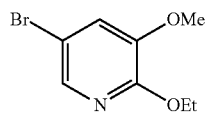

To a 25 mL flask containing (63.8 mg, 1.2 mmol) of sodium ethoxide was added 3 mL dry ethanol. The mixture was stirred for 30 minutes. 2-Chloro-3-methoxy-5-bromopyridine (230 mg, 1.04 mmol) was added to the mixture and heated to 60° C. for 16 hours. The reaction was allowed to cool and the solvent was removed. Ethyl acetate was added (50 ml) was added to the residue. The ethyl acetate solution was washed with water and then brine. The organic solvent was dried and concentrated, purified by ISCO flash chromatography using 10% ethyl acetate in hexane to give 220 mg (97% yield) of the desired product. $^1$H NMR (300 MHz, CDCl$_3$) δ: 7.71 (s, 1H), 7.09 (s, 1H), 4.37 (qt, 2H), 3.82 (s, 3H), 1.38 (t, 3H).

d. Preparation of Compound

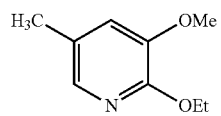

To a solution of known 2-ethoxy-3-methoxy-5-bromopyridine (100 mg, 0.34 mmol) in 1,4-dioxane (3.0 ml), trimethyl boroxine (80 mg, 0.69 mmol) and Pd(dppf)Cl$_2$ (56.3 mg, 0.069 mmol) was added, followed by $CsCO_3$ (300 mg, 0.92 mmol). The mixture was degassed for 30 minutes, and then heated to 90° C. for 16 hr. After cooling, the crude mixture was filtered on celite and extracted with EtOAc (3×), washed with NaCl, the organic layer was dried with Na$_2$SO$_4$ and concentrated to give crude product. The crude product was purified by ISCO flash chromatography using 10% EtOAc in hexane, giving 50 mg compound (Yield: 84%). $^1$H NMR (300 MHz, CDCl$_3$) δ: 7.52 (s, 1H), 6.84 (s, 1H), 4.45 (q, 2H), 3.82 (s, 3H), 2.21 (s, 3H), 1.39 (t, 3H).

Example 2

Preparation of Compound

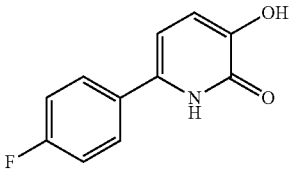 [SMILES: O=c1[nH]c(-c2ccc(F)cc2)ccc1O]

To a solution of 2,3-(dibenzyloxy)-6-(4-fluorophenyl)pyridine (50 mg, 0.129 mmol) in MeOH (10 ml), palladium 10 wt % on activated carbon (catalytic amount) was added. This mixture was then stirred under hydrogen using balloon for 16 hours. The mixture was then filtered through Celite and was washed with MeOH (15 ml). The solvent was then evaporated under reduced pressure to afford a tan solid 15 mg (yield: 57%). $^1$H NMR (300 MHz, MeOD-d$_4$) δ: 7.65-7.60 (m, 2H), 7.21 (t, J=9.0 Hz, 2H), 6.95 (d, J=6.0 Hz, 1H), 6.47 (d, J=6.0 Hz, 1H).

The intermediates were prepared as follows:

a. Preparation of Compound

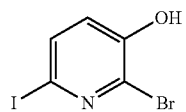

To a suspension of 2-bromopyridin-3-ol (2.41 g, 13.9 mmol) in 34.6 mL water was added potassium carbonate (3.83 g, 27.7 mmol), then iodine (3.87 g, 15.2 mmol), and this mixture was stirred at room temperature for 12 hours. The reaction mixture was then cooled to 0° C., 2N aq HCl was added until pH 6. The resulting precipitate was collected by filtration, washed with water and dried to give 2-bromo-6-iodopyridine-3-ol (3.6 g, 83% yield). LC/MS: 300 (M+H); $^1$H NMR (300 MHz, CDCl$_3$) δ: 7.45 (d, J=8.1 Hz, 1H), 6.85 (d, J=8.1 Hz, 1H).

b. Preparation of Compound

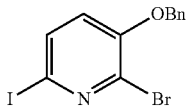

To a solution of 2-bromo-6-iodopyridine-3-ol (1.0 g, 3.33 mmol) in 10 mL methanol was added potassium carbonate (922 mg, 6.67 mmol) and benzyl bromide (1.19 mL, 10.0 mmol), and the resulting mixture was heated at 50° C. for 12 hours. After cooling to room temperature, the solvent was removed and the resulting residue was partitioned between water and ethyl acetate. The organic layer was dried and evaporated to give the crude product, which was pure enough for the next step. $^1$H NMR (300 MHz, CDCl$_3$) δ: 7.49 (d, J=8.4 Hz, 1H), 7.39-7.33 (m, 5H), 6.82 (d, J=8.4 Hz, 1H), 5.13 (s, 2H).

c. Preparation of Compound

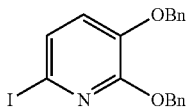

To a solution of benzyl alcohol (1.3 g) in 4 mL DMF was slowly added NaH (400 mg) at 0° C. The mixture was stirred at room temperature for 30 minutes after which 3-(benzyloxy)-2-bromo-6-iodopyridine (1.2 g) was added. The resulting solution was heated to 100° C. for 1 hour under nitrogen. After cooling, the mixture was diluted with water and extracted with ethyl acetate. The organic layer was dried, evaporated under vacuum and purified ISCO flash chromatography to give the desired product in 85% yield. $^1$H NMR (300 MHz, CDCl$_3$) δ: 7.50-7.22 (m, 10H), 7.13 (d, J=8.0 Hz, 1H), 6.74 (d, J=8.0 Hz, 1H), 5.44 (s, 2H), 5.1 (s, 2H).

d. Preparation of Compound

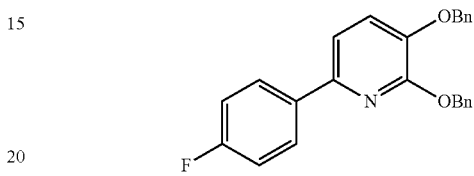

To a solution of 6-iodo-2,3-dibenzyloxypyridine (60 mg, 0.14 mmol) in 4 ml dioxane:water (3:1) was added 4-fluorophenylboronic acid (40 mg, 0.28 mmol) and potassium carbonate (39 mg, 0.28 mmol). The resulting mixture was degassed for 15 minutes after which Pd (PPh$_3$)$_4$ (16 mg, 0.014 mmol) was added and the mixture was further degassed for 15 minutes. The reaction mixture was then heated at 100° C. for 12 hours. After cooling to room temperature, the reaction mixture was diluted with ethyl acetate and was washed with saturated sodium bicarbonate, followed by brine. The organic phase was dried with sodium sulfate and concentrated under reduced pressure to afford crude product which was purified by ISCO flash chromatography using 10%-100% EtOAc in hexane to afford pure product 50 mg solid (90%). $^1$H NMR (300 MHz, CDCl$_3$) δ: 7.88-7.85 (m, 2H), 7.55-7.53 (m, 2H), 7.41-7.32 (m, 8H), 7.15-7.06 (m, 4H), 5.61 (s, 2H), 5.19 (s, 2H).

Example 3

Preparation of Compound

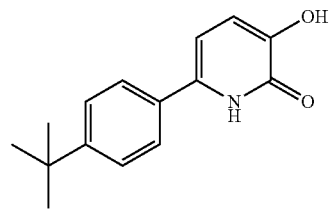 [SMILES: CC(C)(C)c1ccc(-c2ccc(O)c(=O)[nH]2)cc1]

To a solution of 2,3-(dibenzyloxy)-6-(4-t-butylphenyl)pyridine (25 mg, 0.06 mmol) in MeOH (10.0 ml), palladium (10 wt % on activated carbon, catalytic amount) was added. This mixture was then stirred under hydrogen using balloon for 16 hours. The mixture was then filtered through Celite and was washed with MeOH (15 ml). The solvent was then evaporated under reduced pressure to afford a tan solid 10 mg (yield: 70%). $^1$H NMR (300 MHz, MeOD-d$_4$) δ: 7.42

(m, 4H), 6.82 (d, J=6.0 Hz, 1H), 6.4 (d, J=6.0 Hz, 1H), 1.26 (s, 9H).

The intermediate was prepared as follows.

a. Preparation of Compound

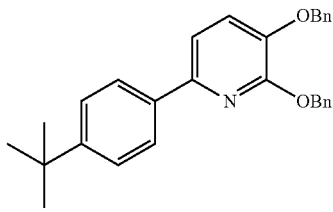 [SMILES: CC(C)(C)c1ccc(-c2ccc(OCc3ccccc3)c(OCc3ccccc3)n2)cc1]

To a solution of intermediate 2c (6-iodo-2,3-dibenzyloxy-pyridine) (60 mg, 0.14 mmol) in 4 ml dioxane:water (3:1) was added 4-t-butylphenylboronic acid (40 mg, 0.28 mmol) and potassium carbonate (39 mg, 0.28 mmol). The resulting mixture was degassed for 15 minutes after which Pd (PPh$_3$)$_4$ (16 mg, 0.014 mmol) was added and the mixture was further degassed for 15 minutes. The reaction mixture was then heated at 100° C. for 12 hours. After cooling to room temperature, the reaction mixture was diluted with ethyl acetate and was washed with saturated sodium bicarbonate, followed by brine. The organic phase was dried with sodium sulfate and concentrated under reduced pressure to afford crude product which was purified by ISCO flash chromatography using 10%-100% EtOAc in hexane to afford 44 mg product pure product (yield: 72%) $^1$H NMR (300 MHz, CDCl$_3$) δ: 7.85 (d, J=8.7 Hz, 2H), 7.54 (d, J=6.9 Hz, 2H), 7.45-7.3 (m, 10H), 7.20 (d, J=8.0 Hz, 1H), 7.10 (d, J=8.1 Hz, 1H), 5.63 (s, 2H), 5.17 (s, 2H), 1.35 (s, 9H).

Example 4

Preparation of Compound

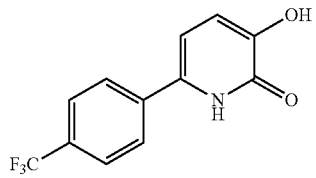

To a solution of 2,3-(dibenzyloxy)-6-[(4-CF$_3$)phenyl)]pyridine (25 mg, 0.057 mmol) in MeOH (10.0 ml), Palladium (10 wt % on activated carbon, catalytic amount) was added. This mixture was then stirred under hydrogen using balloon for 16 hours. The mixture was filtered through Celite and washed with MeOH (15 ml). The solvent was then evaporated under reduced pressure to afford a tan solid 10 mg (yield: 69%): $^1$H NMR (300 MHz, MeOD-d$_4$) δ: 7.72 (m, 4H), 7.0 (d, J=6.0 Hz, 1H), 6.48 (d, J=6.0 Hz, 1H).

The intermediate was prepared as follows.

a. Preparation of Compound

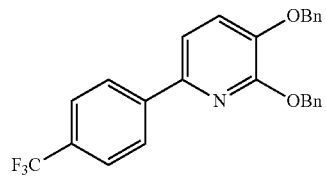 [SMILES: FC(F)(F)c1ccc(-c2ccc(OCc3ccccc3)c(OCc3ccccc3)n2)cc1]

To a solution of intermediate 2c (6-iodo-2,3-dibenzyloxy-pyridine) (50 mg, 0.12 mmol) in 4 ml dioxane:water (3:1) was added 4-(trifluoromethyl)phenylboronic acid (45.5 mg, 0.24 mmol) and potassium carbonate (36 mg, 0.24 mmol). The resulting mixture was degassed for 15 minutes after which Pd (PPh$_3$)$_4$ (14 mg, 0.012 mmol) was added and the mixture was further degassed for 15 minutes. The reaction mixture was then heated at 100° C. for 12 hours. After cooling to room temperature, the reaction mixture was diluted with ethyl acetate and was washed with saturated sodium bicarbonate, followed by brine. The organic phase was dried with sodium sulfate and concentrated under reduced pressure to afford crude product which was purified by ISCO flash chromatography using 10%-100% EtOAc in hexane to afford 25 mg product pure product (yield: 48%); $^1$H NMR (300 MHz, CDCl$_3$) δ: 7.99 (d, J=8.1 Hz, 2H), 7.64 (d, J=8.1 Hz, 2H), 7.53 (d, J=8.1 Hz, 2H), 7.43-7.23 (m, 11H), 7.11 (d, J=8.1 Hz, 1H), 5.61 (s, 2H), 5.19 (s, 2H).

Example 5

Preparation of Compound

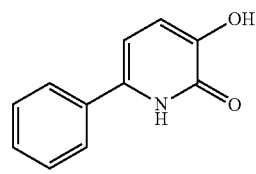 [SMILES: O=c1[nH]c(-c2ccccc2)ccc1O]

To a solution of 2,3-(dibenzyloxy)-6-(phenyl)pyridine (76 mg, 0.2 mmol) in MeOH (10 ml), Palladium 10 wt % on activated carbon (catalytic amount) was added. This mixture was then stirred under hydrogen using balloon for 16 hours. The mixture was then filtered through Celite and washed with MeOH (15 ml). The solvent was then evaporated under reduced pressure to afford a solid 25 mg (yield: 64%). $^1$H NMR (300 MHz, MeOD-d$_4$) δ: 7.60-7.41 (m, 5H), 6.94 (d, J=7.5 Hz, 1H), 6.50 (d, J=7.5 Hz, 1H).

The intermediate was prepared as follows.

a. Preparation of Compound

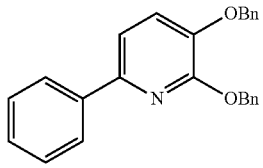 [SMILES: c1ccc(COc2ccc(-c3ccccc3)nc2OCc2ccccc2)cc1]

To a solution of intermediate 2c (6-iodo-2,3-dibenzyloxy-pyridine) (100 mg, 0.23 mmol) in (3:1) ml dioxane:water was added phenylboronic acid (58.2 mg, 0.47 mmol) and potassium carbonate (66 mg, 0.46 mmol). The resulting mixture was degassed for 15 minutes after which Pd (PPh$_3$)$_4$ (35 mg, 0.03 mmol) was added and the mixture was further degassed for 15 minutes. The reaction mixture was then heated at 100° C. for 12 hours. After cooling to room temperature, the reaction mixture was diluted with ethyl acetate and was washed with saturated sodium bicarbonate, followed by brine. The organic phase was dried with sodium sulfate and concentrated under reduced pressure to afford crude product which was purified by ISCO flash chromatography using 10%-100% EtOAc in hexane to afford 76 mg product pure product (yield: 86%) $^1$H NMR (300 MHz, CDCl$_3$) δ: 7.92 (d, J=7.2 Hz, 2H), 7.6 (d, J=7.2 Hz, 2H), 7.44-7.32 (m, 10H), 7.23 (d, J=8.4 Hz, 2H), 7.13 (d, 1H), 5.64 (s, 2H), 5.19 (s, 2H).

Example 6

Preparation of Compound

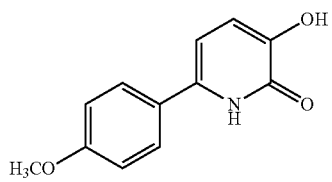 [SMILES: COc1ccc(-c2ccc(O)c(=O)[nH]2)cc1]

To a solution of 2,3-(dibenzyloxy)-6-(4-methoxyphenyl) pyridine (100 mg, 0.26 mmol) in MeOH (10 ml), Palladium 10 wt % on activated carbon (catalytic amount) was added. This mixture was then stirred under hydrogen using balloon for 16 hours. The mixture was then filtered through Celite and was washed with MeOH (15 ml). The solvent was then evaporated under reduced pressure to afford a solid 14 mg (yield: 25%). $^1$H NMR (300 MHz, MeOD-d$_4$) δ: 7.5 (d, J=6.0 Hz, 2H), 7.12 (d, 1H), 6.82 (d, 2H), 6.7 (d, J=6.0 Hz, 1H). 3.68 (s, 3H).

The intermediate was prepared as follows a. Preparation of Compound

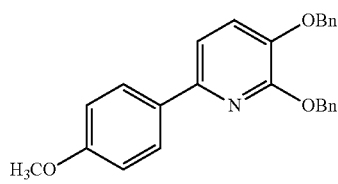 [SMILES: COc1ccc(-c2ccc(OCc3ccccc3)c(OCc3ccccc3)n2)cc1]

To a solution of intermediate 2c (6-iodo-2,3-dibenzyloxy-pyridine) (100 mg, 0.23 mmol) in 4 ml dioxane:water (3:1) added 4-methoxyphenylboronic acid (72.9 mg, 0.48 mmol) and potassium carbonate (66 mg, 0.48 mmol). The resulting mixture was degassed for 15 minutes after which Pd (PPh$_3$)$_4$ (35 mg, 0.03 mmol) was added and the mixture was further degassed for 15 minutes. The reaction mixture was then heated at 100° C. for 12 hours. After cooling to room temperature, the reaction mixture was diluted with ethyl acetate and was washed with saturated sodium bicarbonate, followed by brine. The organic phase was dried with sodium sulfate and concentrated under reduced pressure to afford crude product which was purified by ISCO flash chromatography using 10%-100% EtOAc in hexane to afford 90 mg of the desired product (yield: 94%) $^1$H NMR (300 MHz, CDCl$_3$) δ: 7.84 (d, J=9.0 Hz, 2H), 7.52 (d, J=9.0 Hz, 2H), 7.4-7.3 (m, 8H), 7.10 (qt, J=7.8 Hz, 2H), 6.92 (d, J=9.0 Hz, 2H), 5.60 (s, 2H), 5.16 (s, 2H), 3.83 (s, 3H).

Example 7

Preparation of Compound

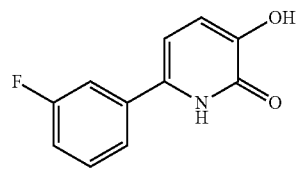 [SMILES: O=c1[nH]c(-c2cccc(F)c2)ccc1O]

To a solution of 2,3-bis(benzyloxy)-6-(3-fluorophenyl) pyridine (100 mg, 0.23 mmol) in MeOH (10.0 ml), palladium 10 wt % on activated carbon (catalytic amount) was added. This mixture was charged with hydrogen using balloon and the reaction was run for 16 hours. The mixture was filtered on celite and was washed with MeOH (15.0 ml). The filtrate was evaporated under reduced pressure to afford a solid (25 mg) in 50.1% yield. $^1$H NMR (300 MHz, DMSO-d$_6$) δ: 9.36 (s, 1H), 7.7 (m, 2H), 7.23 (m, 1H), 6.84 (s, 1H), 6.60 (s, 1H).

The intermediate was prepared as follows a. Preparation of Compound

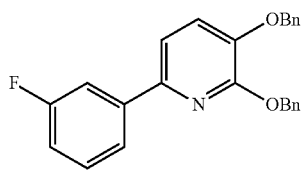 [SMILES: Fc1cccc(-c2ccc(OCc3ccccc3)c(OCc3ccccc3)n2)c1]

To a solution of intermediate 2c (6-iodo-2,3-dibenzyloxy-pyridine) (83 mg, 0.2 mmol) in 4 ml dioxane:water (3:1) was added 2-fluorophenylboronic acid (42 mg, 0.3 mmol) and potassium carbonate (66 mg, 0.48 mmol). The resulting mixture was degassed for 15 minutes after which Pd (PPh$_3$)$_4$ (35 mg, 0.03 mmol) was added and the mixture was further degassed for 15 minutes. The reaction mixture was then heated at 100° C. for 12 hours. After cooling to room temperature, the reaction mixture was diluted with ethyl acetate and was washed with saturated sodium bicarbonate, followed by brine. The organic phase was dried with sodium sulfate and concentrated under reduced pressure to afford crude product which was purified by ISCO flash chromatography using 10%-100% EtOAc in hexane to afford 68 mg of the desired product (Yield: 81%) $^1$H NMR (300 MHz, CDCl$_3$) δ: 7.74-7.64 (m, 2H), 7.61-7.55 (m, 2H), 7.50-7.29 (m, 9H), 7.28 (d, 1H), 7.15 (d, 1H), 7.09-6.99 (m, 1H), 5.67 (s, 2H), 5.23 (s, 2H).

Example 8

Preparation of Compound

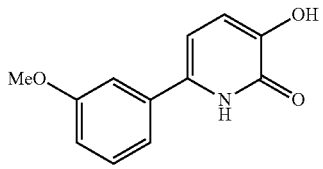 [SMILES: COc1cccc(-c2ccc(O)c(=O)[nH]2)c1]

To a solution of 2,3-bis(benzyloxy)-6-(3-methoxyphenyl)pyridine (80 mg, 0.2 mmol) in MeOH (10 ml), palladium (10 wt % on activated carbon, catalytic amount) was added. This mixture was charged with hydrogen using balloon and the reaction was run for 16 hours. The mixture was filtered through Celite and was washed with MeOH (15 ml). The filtrate was evaporated under reduced pressure to afford a solid (25 mg) in 58% yield. LC/MS. Found, 217.85 (M+H).

The intermediate was prepared as follows.

a. Preparation of Compound

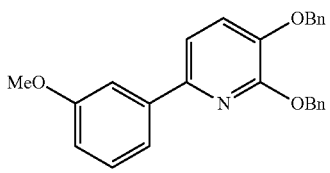 [SMILES: COc1cccc(-c2ccc(OCc3ccccc3)c(OCc3ccccc3)n2)c1]

To a solution of intermediate 2c (6-iodo-2,3-dibenzyloxy-pyridine) (100 mg, 0.24 mmol) in 4 ml dioxane:water (3:1) was added 3-methoxyphenylboronic acid (74 mg, 0.48 mmol) and potassium carbonate (66 mg, 0.5 mmol). The resulting mixture was degassed for 15 minutes after which Pd (PPh$_3$)$_4$ (35 mg, 0.03 mmol) was added and the mixture was further degassed for 15 minutes. The reaction mixture was then heated at 100° C. for 12 hours. After cooling to room temperature, the reaction mixture was diluted with ethyl acetate and was washed with saturated sodium bicarbonate, followed by brine. The organic phase was dried with sodium sulfate and concentrated under reduced pressure to afford crude product which was purified by ISCO flash chromatography using 10-100% EtOAc in hexane to afford 90 mg of the desired product (Yield: 84%)$^1$H NMR (300 MHz, CDCl$_3$) δ: 7.57-7.53 (m, 2H), 7.51-7.3 (m, 10H), 7.26 (d, 1H), 7.16 (d, 1H), 7.9-6.84 (m, 1H), 5.67 (s, 2H), 5.21 (s, 2H).

Example 9

Preparation of Compound

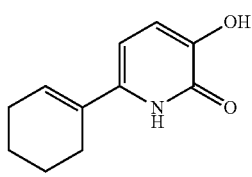 [SMILES: O=c1[nH]c(C2=CCCCC2)ccc1O]

To a solution of 6-cyclohexenyl-2-ethoxy-3-methoxypyridine (50 mg, 0.21 mmol) stirred in CH$_2$Cl$_2$ (3.0 ml) under nitrogen, was added boron tribromide (1M solution in CH$_2$Cl$_2$) (1.0 ml). After addition was completed, the reaction mixture was stirred for 16 hours at room temperature. Dichloromethane was removed under vacuum and aq.HCl (3N) was added. The resulting solid was filtered and then redissolved in dichloromethane and washed with NaHCO$_3$ and brine, dried and evaporated under reduced pressure to afford a tan solid, yield: 34% (14 mg). $^1$H NMR (300 MHz, CDCl$_3$) δ: 6.85 (d, J=7.8 Hz, 1H), 6.25 (s, 1H), 6.14 (d, J=7.8 Hz, 1H), 2.22-2.12 (m, 4H), 1.67-1.54 (m, 4H).

The intermediates were prepared as follows:

a. Preparation of Compound

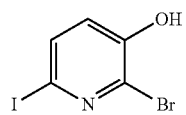

To a solution of 2-bromopyridin-3-ol (2.4 g, 13.8 mmol) in H$_2$O (34 ml) was added potassium carbonate (2.85 g, 20.7 mmol) followed by iodine (3.8 g, 15.2 mmol) and this mixture was stirred at room temperature overnight. This mixture was cooled to 0° C., then slowly quenched by 2N HCl to pH=6. The resulting precipitate was collected by filtration, washed with water and dried to give 2-bromo-6-iodopyridine-3-ol (3 g, 73% yield). LC/MS: 300 (M+H).

b. Preparation of Compound

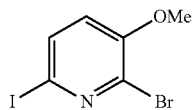

To a solution of 6-iodo-2-bromopyridin 3-ol (1.7 g, 5.9 mmol) in THF (50 ml), K$_2$CO$_3$ (1.22 g, 8.85 mmol) was added, and the mixture was stirred for 10 minutes at 0° C. in an ice bath. To this mixture CH$_3$I (1.0 g, 7.0 mmol) was then added slowly. The reaction mixture was stirred for 16 hours at room temperature. The reaction mixture poured into ice water (100 ml), then extracted with EtOAc (3×), dried in Na$_2$SO$_4$ and evaporated under reduced pressure to afford a white solid 1.5 g (yield: 80.96%). $^1$H NMR (300 MHz, CDCl$_3$) δ: 7.50 (d, J=8.1 Hz, 1H), 6.74 (d, J=8.4 Hz, 1H), 3.88 (s, 3H).

c. Preparation of Compound

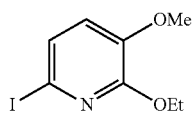 [SMILES: CCOc1nc(I)ccc1OC]

To a solution of 6-iodo-2-bromo-3-methoxypyridine (1.5 g, 4.8 mmol) in EtOH (100 ml), NaOEt (487.6 mg) in EtOH (20 ml) was added for 30 minutes. This reaction was heated to 100° C. for 2 hours. After cooling to room temperature, ethanol was removed under reduced pressure and diluted with 50 ml water. The resulting residue was extracted with CH$_2$Cl$_2$ (3×), washed with brine, dried over Na$_2$SO$_4$ and evaporated under reduced pressure to give a crude oil, which was purified by ISCO flash chromatography using 20% EtOAc in hexanes, recovered starting material (400 mg), collected 6-iodo-2-ethoxyl-3-methoxylpyridine: 600 mg (yield: 45%). $^1$H NMR (300 MHz, CDCl$_3$) δ: 7.22 (d, J=7.8 Hz, 1H), 7.78 (d, J=7.8 Hz, 1H), 4.45 (qt, J=7.5 Hz, 2H), 3.86 (s, 3H), 1.45 (t, J=4.5 Hz, 3H).

d. Preparation of Compound

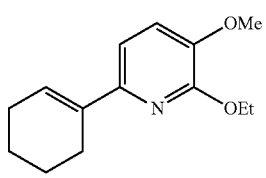 [SMILES: CCOc1nc(C2=CCCCC2)ccc1OC]

A solution of 6-iodo-2-ethoxy-3-methoxy pyridine (150 mg, 0.54 mmol), cyclohexenyl pinacol ester (167 mg, 0.8 mmol), potassium carbonate (138 mg, 1 mmol) in 6 mL (dioxane:water) (3:1) was degassed for 15 minutes. Pd (PPh$_3$)$_4$ (92 mg, 0.08 mmol) was then added and the resulting mixture was heated at 100° C. overnight. The reaction mixture was cooled to room temperature and was diluted with ethyl acetate, washed with NaHCO$_3$ followed by brine. The organic layer was dried over sodium sulfate, evaporated under reduced pressure to give a crude product. Purification by ISCO flash chromatography using a gradient of 10-100% ethyl acetate in hexane afforded the pure product in 83% yield (105 mg). $^1$H NMR (300 MHz, CDCl$_3$) δ: 6.98 (d, J=6.0 Hz, 1H), 6.8 (d, J=6.0 Hz, 1H), 6.7 (m, 1H), 4.5 (qt, 2H), 3.82 (s, 3H), 2.4 (m, 2H), 2.25 (m, 2H), 1.8-1.6 (m, 4H), 1.43 (t, 3H).

Example 10

Preparation of Compound

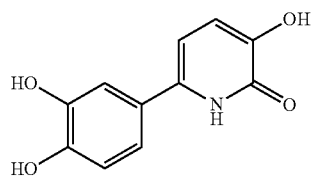 [SMILES: O=c1[nH]c(-c2ccc(O)c(O)c2)ccc1O]

To a solution of 6-(3,4-methylenedioxy)-2-ethoxy-3-methoxypyridine (50 mg, 0.18 mmol) stirred in CH$_2$Cl$_2$ (3.0 ml) under nitrogen, was added boron tribromide (1M solution in CH$_2$Cl$_2$) (0.8 ml). After addition was completed, the reaction mixture was stirred for 16 hours at room temperature. Dichloromethane was removed under vacuum and aq.HCl (3N) was added. The resulting solid was filtered and then redissolved in dichloromethane and washed with NaHCO$_3$ and brine, dried using anhydrous sodium sulfate and evaporated under reduced pressure to afford a crude product which was then purified in ISCO flash chromatography using 10% MeOH in CH$_2$Cl$_2$ to give the desired product, yield: 38% (15 mg). LC/MS. Found, 220 (M+H).

The intermediate was prepared as follows.

a. Preparation of Compound

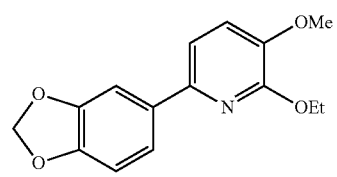 [SMILES: CCOc1nc(-c2ccc3c(c2)OCO3)ccc1OC]

A solution of 6-iodo-2-ethoxy-3-methoxy pyridine (100 mg, 0.36 mmol), 3,4-methylenedioxy-phenylboronic acid (77 mg, 0.46 mmol), potassium carbonate (97 mg, 0.7 mmol)) in 6:2 mL (dioxane:water) was degassed for 15 minutes. Pd (PPh$_3$)$_4$ (63 mg, 0.05 mmol) was then added and the resulting mixture was heated at 100° C. overnight. The reaction mixture was cooled to room temperature and was diluted with ethyl acetate, washed with NaHCO$_3$ followed by brine. The organic layer was dried over sodium sulfate, evaporated under reduced pressure to give a crude product. Purification in ISCO using 10-100% ethyl acetate in hexane afforded the pure product in 100% yield (100 mg). $^1$H NMR (300 MHz, CDCl$_3$) δ: 7.45 (m, 2H), 7.15 (d, J=9.0 Hz, 1H), 7.05 (d, J=9.0 Hz, 1H), 6.84 (d, J=9.0 Hz, 1H), 5.97 (s, 2H), 4.55 (qt, J=9.0 Hz, 2H), 3.87 (s, 3H), 1.47 (t, J=7.2 Hz, 3H).

Example 11

Preparation of Compound

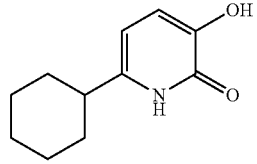 [SMILES: O=c1[nH]c(C2CCCCC2)ccc1O]

To a solution of 6-cyclohexyl-2-ethoxy-3-methoxypyridine (25 mg, 0.11 mmol) stirred in CH$_2$Cl$_2$ (3.0 ml) under nitrogen, was added boron tribromide (1M solution in CH$_2$Cl$_2$) (0.8 ml). After addition was completed, the reaction mixture was stirred for 16 hours at room temperature. Dichloromethane was removed under vacuum and aq.HCl (3N) was added. The resulting solid was filtered and then redissolved in CH$_2$Cl$_2$ and washed with NaHCO$_3$ and brine, dried using anhydrous sodium sulfate and evaporated under reduced pressure to afford a crude product which was then purified by ISCO flash chromatography using 10% MeOH in CH$_2$Cl$_2$ to give the desired product, yield: 49% (10 mg). $^1$H NMR (300 MHz, CDCl$_3$) δ: 6.83 (d, J=6.0 Hz, 1H), 5.98 (d, J=6.0 Hz, 1H), 2.5-1.3 (m, 11H).

The intermediate was prepared as follows.

a. Preparation of Compound

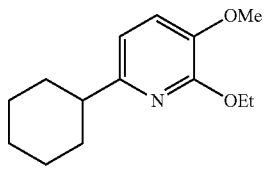

To a solution of 6-(cyclohexen-1-yl)-2-ethoxy-3-methoxypyridine (see Example 9 part d) (50 mg, 0.214 mmol) in MeOH (10.0 ml), palladium 10 wt % on activated carbon (catalytic amount) was added. This mixture was charged with hydrogen using balloon and the reaction was run for 16 hours. The mixture was filtered on Celite and was washed with MeOH (15 ml). The filtrate was evaporated under reduced pressure to afford a solid (30 mg) in 60% yield. $^1$H NMR (300 MHz, CDCl$_3$) δ: 6.92 (d, J=6.0 Hz, 1H), 6.6 (d, J=6.0 Hz, 1H), 4.46 (qt, J=6.3 Hz, 2H), 3.81 (s, 3H), 2.5 (m, 1H), 1.9-1.3 (m, 13H).

Example 12

Preparation of Compound

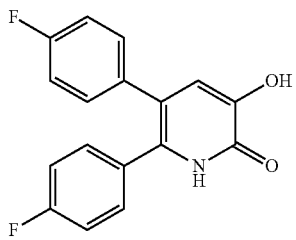 [SMILES: O=c1[nH]c(-c2ccc(F)cc2)c(-c2ccc(F)cc2)cc1O]

To a solution of 2,3-dimethoxy-5,6-bis(4-fluorophenyl) pyridine (100 mg, 0.3 mmol) in CH$_2$Cl$_2$ (3.0 ml) under nitrogen, was added boron tribromide (1.0 M solution in CH$_2$Cl$_2$) (1.5 ml). After addition was completed, the reaction mixture was stirred for 16 hours at room temperature. Dichloromethane was removed from the reaction mixture followed by addition of HCl (3N). The resulting solid was filtered, which was redissolved in CH$_2$Cl$_2$ and washed with NaHCO$_3$ and brine, dried using anhydrous sodium sulfate and evaporated under reduced pressure to afford a solid (80 mg), yield: 87%. $^1$H NMR (300 MHz, DMSO-d$_6$) δ: 7.66 (m, 2H), 7.6 (m, 2H), 7.46 (m, 2H), 7.20 (d, J=6.0 Hz, 2H), 7.08 (m, 1H), 6.7 (d, 1H), 6.28 (d, 1H). LC/MS: 300.20 (M+H).

The intermediates were prepared as follows:

a. Preparation of Compound

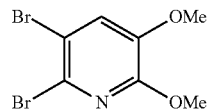

To a solution of commercially available 2,3-dimethoxypyridine (2.0 g, 14.7 mmol) and NaOAc (5.4 g, 44 mmol) in AcOH (25 ml) at 0° C. was added a solution of bromine (2.0 ml, 36.6 mmol) in AcOH (0.5 ml). The cooling bath was removed and the reaction was then stirred at room temperature for 16 hours. The mixture was poured into crushed ice followed by neutralization with 25% aqueous NaOH solution, the aqueous phase was extracted with CH$_2$Cl$_2$ (3×). The combined organic phases were dried over Na$_2$SO$_4$ and concentrated. Purification by ISCO flash chromatography using a gradient of 10-15% EtOAc in hexanes provided the desired product 3.86 g, tan solid (89%): $^1$H NMR (300 MHz, CDCl$_3$) δ: 7.18 (s, 1H), 3.98 (s, 3H), 3.84 (s, 3H).

b. Preparation of Compound

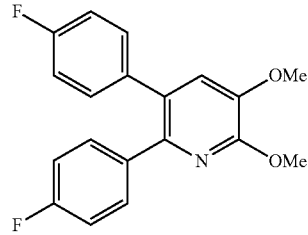 [SMILES: COc1cc(-c2ccc(F)cc2)c(-c2ccc(F)cc2)nc1OC]

The mixture of 5,6-dibromo-2,3-dimethoxypyridine (260 mg, 0.87 mmol), 4-fluorophenylboronic acid (367 mg, 3.0 mmol), Pd(PPh$_3$)$_4$ (303 mg, 0.26 mmol) and K$_2$CO$_3$ (414 mg, 3.0 mmol) in 1,4-dioxane (4.0 mL) and H$_2$O (1.0 ml) was degassed for 30 minutes. This mixture was heated to 100° C. and stirred for 16 hours. The reaction mixture was cooled to room temperature and partitioned between NaHCO$_3$ and EtOAc (3×), and washed with NaCl (1×). The organic phase was dried over Na$_2$SO$_4$ and was concentrated under vacuum. The resulting residue was purified by ISCO flash chromatography using 10% EtOAc in hexane to give 210 mg of the desired product, yield: 73%. $^1$H NMR (300 MHz, CDCl$_3$) δ: 7.35 (m, 2H), 7.20 (m, 2H), 7.20 (m, 2H), 7.17 (m, 2H), 7.04-6.98 (m, 4H), 4.18 (s, 3H), 3.01 (s, 3H). LC/MS: 328.205 (M+H).

Example 13

Preparation of Compound

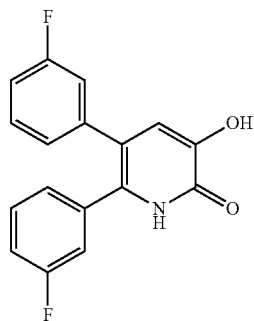 [SMILES: O=c1[nH]c(-c2cccc(F)c2)c(-c2cccc(F)c2)cc1O]

To a solution of 2,3-dimethoxy-5,6-(3-fluorophenyl) pyridine (200 mg, 0.61 mmol) in CH$_2$Cl$_2$ (6.0 ml) under nitrogen, was added boron tribromide (1.0 M solution in CH$_2$Cl$_2$)

(2.0 ml). After addition was completed, the reaction mixture was stirred for 16 hours at room temperature. CH$_2$Cl$_2$ was removed from the reaction mixture followed by addition of HCl (3N). The resulting solid was filtered which was redissolved in CH$_2$Cl$_2$ and washed with NaHCO$_3$ and brine, dried and evaporated under reduced pressure to afford a solid (160 mg), yield: 87%. $^1$H NMR (300 MHz, DMSO-d$_6$) δ: 7.2-7.10 (m, 4H), 7.06-7.03 (m, 4H), 6.80 (s, 1H). LC/MS: 300.202 (M+H).

The intermediate was prepared as follows.

a. Preparation of Compound

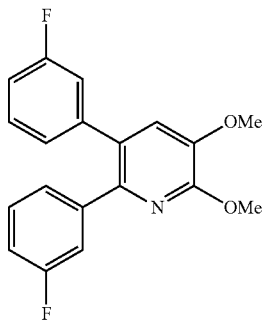 [SMILES: COc1cc(-c2cccc(F)c2)c(-c2cccc(F)c2)nc1OC]

The mixture of 5,6-dibromo-2,3-dimethoxypyridine (260 mg, 0.87 mmol), 3-fluorophenylboronic acid (367 mg, 3.6 mmol), Pd(PPh$_3$)$_4$ (300 mg, 0.26 mmol) and K$_2$CO$_3$ (731 mg, 5.3 mmol) in 1,4-dioxane (5.0 mL) and H$_2$O (1.5 ml) was degassed for 30 minutes. This mixture was heated to 100° C. and stirred for 16 hours. The reaction mixture was cooled to room temperature and partitioned between NaHCO$_3$ and EtOAc (3×), and washed with NaCl (1×). The organic phase was dried over Na$_2$SO$_4$ and was concentrated under vacuum. The resulting residue was purified by ISCO flash chromatography using 10% EtOAc in hexane to give 190 mg of the desired product, yield: 66%. $^1$H NMR (300 MHz, CDCl$_3$) δ: 7.25 (m, 2H), 7.05 (m, 2H), 7.0-6.8 (m, 5H), 4.04 (s, 3H), 3.87 (s, 3H).

Example 14

Preparation of Compound

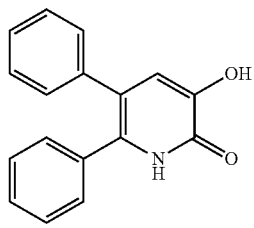 [SMILES: O=c1[nH]c(-c2ccccc2)c(-c2ccccc2)cc1O]

To a solution of 2,3-dimethoxy-5,6-(diphenyl)pyridine (130 mg, 0.45 mmol) in CH$_2$Cl$_2$ (6.0 ml) under nitrogen, was added boron tribromide (2.0 ml of a 1.0 M solution in CH$_2$Cl$_2$). After addition was completed, the reaction mixture was stirred for 16 hours at room temperature. Dichloromethane was removed from the reaction mixture followed by addition of HCl (3N). The resulting solid was filtered. The solid was redissolved in CH$_2$Cl$_2$ and washed with NaHCO$_3$ and brine. The organic phase was then dried and evaporated under reduced pressure to afford a solid (60 mg), yield: 55%. $^1$H NMR (300 MHz, DMSO-d$_6$) δ: 7.58 (m, 6H), 7.23 (t, 1H), 7.15 (m, 1H), 7.07 (t, 1H), 6.7 (d, J=7.2 Hz, 1H).

The intermediate was prepared as follows.

a. Preparation of Compound

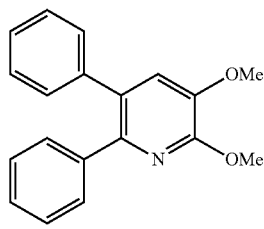 [SMILES: COc1cc(-c2ccccc2)c(-c2ccccc2)nc1OC]

A mixture of 5,6-dibromo-2,3-dimethoxypyridine (150 mg, 0.5 mmol, phenylboronic acid (242 mg, 2.0 mmol), Pd(PPh$_3$)$_4$ (231 mg, 0.2 mmol) and K$_2$CO$_3$ (276 mg, 2.0 mmol) in 1,4-dioxane (5.0 mL) and H$_2$O (1.5 ml) was degassed for 30 minutes. This mixture was heated to 100° C. and stirred for 16 hours. The reaction mixture was cooled to room temperature and partitioned between NaHCO$_3$ and EtOAc (3×), and washed with NaCl (1×). The organic phase was dried over Na$_2$SO$_4$ and was concentrated under vacuum. The resulting residue was purified by ISCO flash chromatography using 10% EtOAc in hexane to give 130 mg of the desired product, yield: 89%. $^1$H NMR (300 MHz, CDCl$_3$) δ: 7.35 (m, 2H), 7.20 (m, 2H), 7.20 (m, 2H), 7.17 (m, 2H), 7.04-6.98 (m, 4H), 4.18 (s, 3H), 3.01 (s, 3H). LC/MS: 328.205 (M+H). $^1$H NMR (300 MHz, CDCl$_3$) δ: 7.4 (m, 2H), 7.29 (m, 3H), 7.24-7.21 (m, 5H), 7.12 (s, 1H), 4.15 (s, 3H), 3.96 (s, 3H). LC/MS: 292.23 (M+H).

Example 15

Preparation of Compound

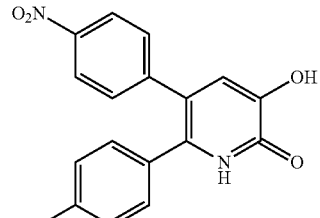

To a solution of 2,3-dimethoxy-5,6-(4-nitrophenyl)pyridine (50 mg, 0.13 mmol) in CH$_2$Cl$_2$ (4.0 ml) under nitrogen, was added boron tribromide (1.0 M solution in CH$_2$Cl$_2$) (1.0 ml). After addition was completed, the reaction mixture was stirred for 16 hours at room temperature. CH$_2$Cl$_2$ was removed from the reaction mixture followed by addition of HCl (3N). The resulting solid was filtered which was redissolved in CH$_2$Cl$_2$ and washed with NaHCO$_3$ and brine, dried and evaporated under reduced pressure to afford a solid (35 mg), yield: 76%. $^1$H NMR (300 MHz, DMSO-d$_6$) δ: 8.14-

8.06 (m, 4H), 7.45 (d, J=8.7 Hz, 2H), 7.31 (d, J=8.1 Hz, 2H), 6.93 (s, 1H). LC/MS: 354.07 (M+H).

The intermediate was prepared as follows.

a. Preparation of Compound

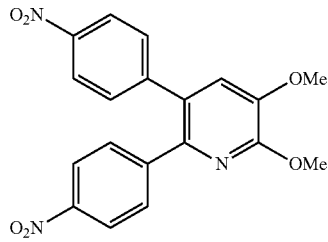 [SMILES: COc1cc(-c2ccc([N+](=O)[O-])cc2)c(-c2ccc([N+](=O)[O-])cc2)nc1OC]

A mixture of 5,6-dibromo-2,3-dimethoxypyridine (296 mg, 1.0 mmol, 4-nitrophenyl pinacol boronate ester 996 mg, 4.0 mmol), Pd(PPh$_3$)$_4$ (462 mg, 0.4 mmol) and K$_2$CO$_3$ (552 mg, 4.0 mmol) in 1,4-dioxane (5.0 mL) and H$_2$O (1.5 ml) was degassed for 30 minutes. This mixture was heated to 100° C. and stirred for 16 hours. The reaction mixture was cooled to room temperature and partitioned between NaHCO$_3$ and EtOAc (3×), and washed with NaCl (1×). The organic phase was dried over Na$_2$SO$_4$ and was concentrated under vacuum. The resulting residue was purified by ISCO flash chromatography using 10% EtOAc in hexane to give 150 mg of the desired product, yield: 39%. $^1$H NMR (300 MHz, CDCl$_3$) δ: 8.15 (d, J=9.0 Hz, 2H), 8.06 (d, J=9.0 Hz, 2H), 7.46 (d, J=8.7 Hz, 2H), 7.33 (d, J=8.7 Hz, 2H), 7.05 (s, 1H), 4.10 (s, 3H), 3.96 (s, 3H).

Example 16

Preparation of Compound

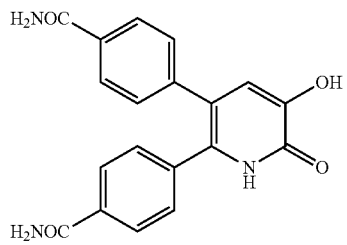 [SMILES: NC(=O)c1ccc(-c2cc(O)c(=O)[nH]c2-c2ccc(C(N)=O)cc2)cc1]

To a solution of 2,3-dimethoxy-5,6-bis(4-carboxyamidophenyl)pyridine (50 mg, 0.123 mmol) in CH$_2$Cl$_2$ (4.0 ml) under nitrogen, was added boron tribromide (1.5 ml, 1.0 M solution in CH$_2$Cl$_2$). After addition was completed, the reaction mixture was stirred for 16 hours at room temperature. Dichloromethane was removed from the reaction mixture followed by addition of HCl (3N). The resulting solid was filtered. The solid was then redissolved in CH$_2$Cl$_2$ and washed with NaHCO$_3$ and brine, dried using anhydrous sodium sulfate and evaporated under reduced pressure to afford a solid (25 mg), yield: 54%. $^1$H NMR (300 MHz, DMSO d$_3$) δ: 8.0 (s, 1H), 7.93 (s, 1H), 7.76 (m, 4H), 7.42 (s, 1H), 7.34 (s, 1H), 7.22 (d, J=9.0 Hz, 2H), 7.11 (d, J=9.0 Hz, 2H), 6.85 (s, 1H).

The intermediate was prepared as follows.

a. Preparation of Compound

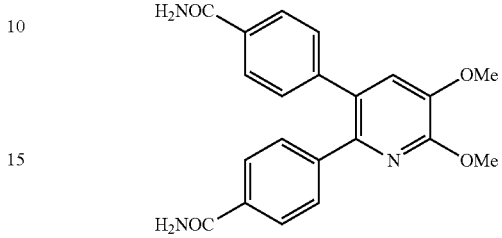

A mixture of 5,6-dibromo-2,3-dimethoxypyridine (296 mg, 1.0 mmol), 4-carboxamidophenyl boronic acid (659 mg, 4.0 mmol-4 equiv), Pd(PPh$_3$)$_4$ (462 mg, 0.4 mmol) and K$_2$CO$_3$ (552 mg, 4.0 mmol) in 1,4-dioxane (5.0 mL) and H$_2$O (1.5 ml) was degassed for 30 minutes. This mixture was heated to 100° C. and stirred for 16 hours. The reaction mixture was cooled to room temperature and partitioned between NaHCO$_3$ and EtOAc (3×), and washed with NaCl (1×). The organic phase was dried over Na$_2$SO$_4$ and was concentrated under vacuum. The resulting residue was purified by ISCO flash chromatography using 10% EtOAc in hexane to give 250 mg of the desired product, yield: 66%; $^1$H NMR (300 MHz, MeOD-d$_4$) δ: 7.70 (d, J=8.1 Hz, 2H), 7.61 (d, J=8.1 Hz, 2H), 7.31 (d, J=8.1 Hz, 2H), 7.19 (m, 3H), 3.95 (s, 3H), 3.83 (s, 3H).

Example 17

Preparation of Compound

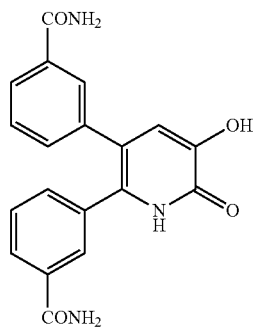 [SMILES: NC(=O)c1cccc(-c2cc(O)c(=O)[nH]c2-c2cccc(C(N)=O)c2)c1]

To a solution of 2,3-dimethoxy-5,6-bis(3-carboxyamidophenyl)pyridine (50 mg, 0.123 mmol) in CH$_2$Cl$_2$ (4.0 ml) under nitrogen, was added boron tribromide (1.5 ml, 1.0 M solution in CH$_2$Cl$_2$). After addition was completed, the reaction mixture was stirred for 16 hours at room temperature. The dichloromethane was removed from the reaction mixture followed by addition of HCl (3N). The resulting solid was filtered which was redissolved in CH$_2$Cl$_2$ and washed with NaHCO$_3$ and brine, dried and evaporated under reduced pressure to afford a solid (19 mg), yield: 41%. $^1$H NMR (300 MHz, DMSO d$_3$) δ:7.89 (d, J=6.0 Hz, 1H), 7.8-7.63 (m, 3H), 7.37-7.10 (m, 4H), 7.0 (d, J=6.0 Hz, 1H), 6.89 (s, 1H).

The intermediate was prepared as follows.

a. Preparation of Compound

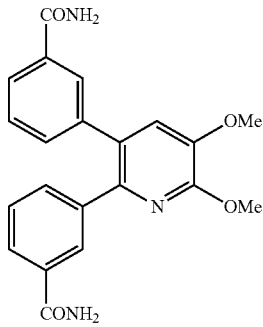 [SMILES: COc1cc(-c2cccc(C(N)=O)c2)c(-c2cccc(C(N)=O)c2)nc1OC]

A mixture of 5,6-dibromo-2,3-dimethoxypyridine (200 mg, 0.67 mmol), 3-carboxamidophenyl boronic acid (442 mg, 2.68 mmol-4 equiv.), Pd(PPh$_3$)$_4$ (346 mg, 0.3 mmol) and K$_2$CO$_3$ (250 mg, 1.8 mmol) in 1,4-dioxane (4.0 mL) and H$_2$O (1.0 ml) was degassed for 30 minutes. This mixture was heated to 100° C. and stirred for 16 hours. The reaction mixture was cooled to room temperature and partitioned between NaHCO$_3$ and EtOAc (3×), and washed with NaCl (1×). The organic phase was dried over Na$_2$SO$_4$ and was concentrated under vacuum. The resulting residue was purified by ISCO flash chromatography using 10% EtOAc in hexane to give 160 mg of the desired product, yield: 63%; $^1$H NMR (300 MHz, MeODd$_4$) δ: 7.86 (s, 1H), 7.74 (s, 1H), 7.68-7.59 (m, 2H), 7.29-7.14 (m, 5H), 3.96 (s, 3H), 3.83 (s, 3H).

Example 18

Preparation of Compound

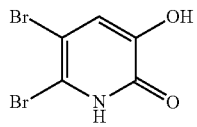

To a solution of 5,6-dibromo-2,3-dimethoxypyridine (120 mg, 0.4 mmol) in CH$_2$Cl$_2$ (3.0 ml) under nitrogen, was added boron tribromide (1.2 ml, 1.0 M solution in CH$_2$Cl$_2$). After addition was completed, the reaction mixture was stirred for 16 hours at room temperature. Methylenechloride was removed from the reaction mixture followed by addition of HCl (3N). The resulting solid was filtered. The solid was then redissolved in CH$_2$Cl$_2$ and washed with NaHCO$_3$ and brine, dried using anhydrous sodium sulfate and the organic phase evaporated under reduced pressure to afford a solid (80 mg), yield: 74%. $^1$H NMR (300 MHz, DMSO-d$_6$) δ: 7.3 (s, 1H).

Example 19

Preparation of Compounds

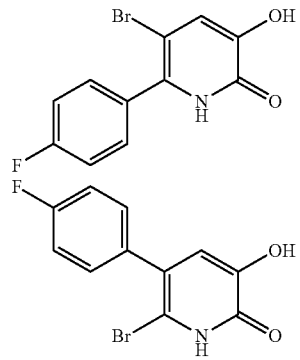

To a mixture of substituted 2,3-dimethoxy-5-bromo-6-phenylpyridine and 2,3-dimethoxy-5-phenyl-6-bromopyridine (85 mg, 0.27 mmol) in CH$_2$Cl$_2$ (3.0 ml) under nitrogen, was added boron tribromide (1.0 ml. 1.0 M solution in CH$_2$Cl$_2$). After addition was completed, the reaction mixture was stirred for 16 hours at room temperature. The dichloromethane was removed from the reaction mixture followed by addition of HCl (3N) to the residue. The resulting solid was filtered. The solid was redissolved in CH$_2$Cl$_2$ and washed with NaHCO$_3$ and brine, dried using anhydrous sodium sulfate and evaporated under reduced pressure to afford a solid (70 mg), yield: 90%. LC/MS: Calculated 284. found: 284.29, 286.23. Rt=2.47 (39%), 2.97 (61%).

The intermediate was prepared as follows.

a. Preparation of Compounds

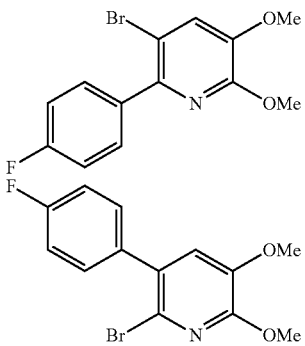

A mixture of 5,6-dibromo-2,3-dimethoxypyridine (296 mg, 1.0 mmol), 4-fluorophenylboronic acid (167 mg, 1.2 mmol-1.2 equiv), Pd(PPh$_3$)$_4$ (138 mg, 0.12 mmol) and K$_2$CO$_3$ (272 mg, 2.0 mmol) in 1,4-dioxane (3.0 mL) and H$_2$O (1.0 ml) was degassed for 30 minutes. This mixture was heated to 100° C. and stirred for 16 hours. The reaction mixture was cooled to room temperature and partitioned between NaHCO$_3$ and EtOAc (3×), and washed with NaCl (1×). The organic phase was dried over Na$_2$SO$_4$ and was concentrated under vacuum. The resulting residue was purified by ISCO flash chromatography using 10% EtOAc in hexane to give 85 mg of the desired (1:1) mixture of products, yield: 27%; ¹H NMR (300 MHz, CDCl₃) δ: 7.29-7.25 (m, 2H), 7.11 (m, 2H), 6.98-6.87 (m, 4H), 4.07 (s, 3H), 3.91 (s, 3H).

Example 20

Preparation of Compounds

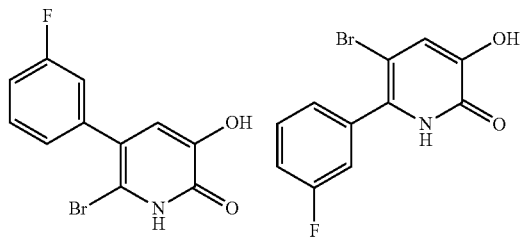

To a mixture of the disubstituted dimethoxypyridine (120 mg, 0.38 mmol) in CH₂Cl₂ (4.0 ml) under nitrogen, was added boron tribromide (1.2 ml, 1.0 M solution in CH₂Cl₂). After addition was completed, the reaction mixture was stirred for 16 hours at room temperature. The dichoromethane was removed from the reaction mixture followed by addition of HCl (3N) to the residue. The resulting solid was filtered. The solid was then redissolved in CH₂Cl₂ and washed with NaHCO₃ and brine, dried using anhydrous sodium sulfate and evaporated under reduced pressure to afford a solid (85 mg), yield: 78%. LC/MS: Calculated, 284. found: 284.25, 286.20, Rt=2.20 (36%), 2.48 (64%).

The intermediate was prepared as follows.

a. Preparation of Compounds

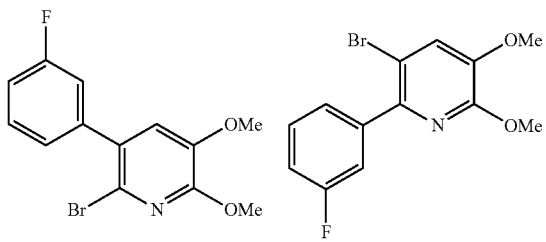

A mixture of 5,6-dibromo-2,3-dimethoxypyridine (296 mg, 1.0 mmol), 3-fluorophenylboronic acid (168 mg, 1.2 mmol-1.2 equiv-), Pd(PPh₃)₄ (138 mg, 0.12 mmol) and K₂CO₃ (272 mg, 2.0 mmol) in 1,4-dioxane (3.0 mL) and H₂O (1.0 ml) was degassed for 30 minutes. This mixture was heated to 100° C. and stirred for 16 hours. The reaction mixture was cooled to room temperature and partitioned between NaHCO₃ and EtOAc (3×), and washed with NaCl (1×). The organic phase was dried over Na₂SO₄ and was concentrated under vacuum. The resulting residue was purified by ISCO flash chromatography using 10% EtOAc in hexane to give 120 mg of the desired mixture (1:1) of products, yield: 38%; ¹H NMR (300 MHz, CDCl₃) δ: 7.5 (m, 1H), 7.43-7.31 (m, 2H), 7.23 (s, 1H), 7.10-7.01 (m, 1H), 3.99 (s, 3H), 3.87 (s, 3H).

Example 21

Preparation of Compound

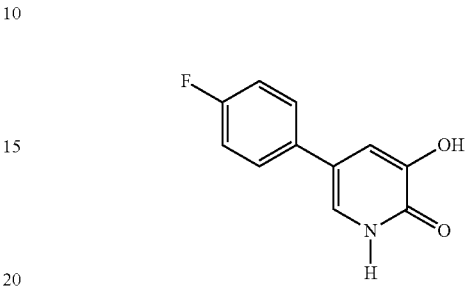

To a solution of 2-ethoxy-3-methoxy-5-(4-fluorophenyl)pyridine (30 mg, 0.12 mmol) stirred in CH₂Cl₂ (1.0 ml) under nitrogen, was added boron tribromide (1M solution in CH₂Cl₂) (0.5 ml). After addition was completed, the reaction mixture was stirred for 16 hours at room temperature. Dichloromethane was removed under vacuum and aq.HCl (3N) was added. The resulting solid was filtered and then redissolved in CH₂Cl₂ and washed with NaHCO₃ and brine, dried and evaporated under reduced pressure to afford a tan solid 19 mg (77% yield). ¹H NMR (300 MHz, DMSO-d₆) δ: 9.19 (s, 1H), 7.51 (m, 2H), 7.14 (m, 3H).

The intermediates were prepared as follows.

a. Preparation of Compound

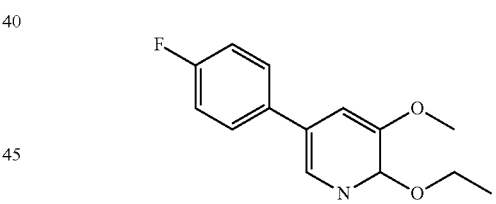

To a solution of intermediate 2c (2-ethoxy-3-methoxy-5-bromopyridine) (140 mg, 0.5 mmol) in 4 ml dioxane:water (3:1) was added 4-(fluoromethyl)phenylboronic acid (104 mg, 0.75 mmol) and potassium carbonate (138 mg, 1.0 mmol). The resulting mixture was degassed for 15 minutes after which Pd (PPh₃)₄ (60 mg, 0.06 mmol) was added and the mixture was further degassed for 15 minutes. The reaction mixture was then heated at 100° C. for 12 hours. After cooling to room temperature, the reaction mixture was diluted with ethyl acetate and was washed with saturated sodium bicarbonate, followed by brine. The organic phase was dried with sodium sulfate and concentrated under reduced pressure to afford crude product which was purified by ISCO flash chromatography using 10%-100% EtOAC in hexane to afford 119 mg product pure product (yield: 96%); ¹H NMR (300 MHz, CDCl₃) δ: 7.84 (s, 1H), 7.44 (m, 2H), 7.14-7.08 (m, 3H), 4.46 (qt, J=7.2 Hz, 2H), 3.88 (s, 3H), 1.44 (qt, J=7.2 Hz, 3H).

Example 22

Preparation of Compound

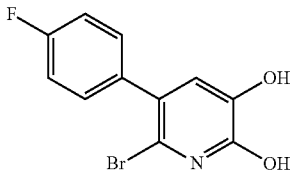 [SMILES: Oc1cc(-c2ccc(F)cc2)c(Br)nc1O]

To a solution of 2-ethoxy-3-methoxy-6-bromo-5-(4-fluorophenyl)pyridine (30 mg, 0.08 mmol) stirred in $CH_2Cl_2$ (4.0 ml) under nitrogen, was added boron tribromide (1M solution in $CH_2Cl_2$) (0.5 ml). After addition was completed, the reaction mixture was stirred for 16 hours at room temperature. Dichloromethane was removed under vacuum and aq. HCl (3N) was added. The resulting solid was filtered and then redissolved in $CH_2Cl_2$ and washed with $NaHCO_3$ and brine, dried and evaporated under reduced pressure to afford a solid (15 mg (60% yield). $^1$H NMR (300 MHz, DMSO-$d_6$) δ: 7.39 (m, 2H), 7.23 (m, 2H), 6.95 (s, 1H).

The intermediates were prepared as follows.

a. Preparation of Compound

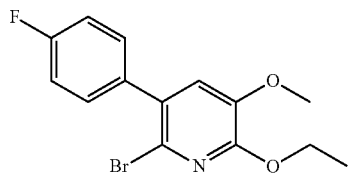 [SMILES: CCOc1nc(Br)c(-c2ccc(F)cc2)cc1OC]

To a mixture of 21a (2-ethoxy-3-methoxy-5-(4-fluorophenyl)pyridine) (85 mg, 0.34 mmol) in acetic acid (1.0 mL) was added sodium acetate (187 mg, 1.4 mmol). The reaction mixture was cooled to −32° C. and $Br_2$ (0.008 mL) in acetic acid (0.3 mL) was added dropwise. The reaction mixture was stirred at this temperature for 2 h. The temperature of the cooling bath was raised to 0° C. and the stirring was continued for 1 h. To this mixture 25% NaOH was added at 0° C. until pH 6 and then extracted with dichloromethane three times. The organic layer wad dried, concentrated and purified by ISCO using 5% EtOAC in hexane to afford a white solid as pure product 65 mg (58% yield). $^1$H NMR (300 MHz, CDCl$_3$) δ: 7.38-7.34 (m, 2H), 7.13-7.07 (m, 2H), 6.96 (s, 1H), 4.47 (qt, J=7.2 Hz, 2H), 3.85 (s, 3H), 1.45 (qt, J=7.2 Hz, 3H). LC/MS: 332 (M+H).

Example 23

Preparation of Compound

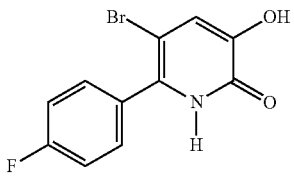 [SMILES: O=c1[nH]c(-c2ccc(F)cc2)c(Br)cc1O]

To a solution of 2-ethoxy-3-methoxy-5-bromo-6-(4-fluorophenyl)pyridine (30 mg, 0.9 mmol) stirred in $CH_2Cl_2$ (1.0 ml) under nitrogen, was added boron tribromide (1M solution in $CH_2Cl_2$) (0.5 ml). After addition was completed, the reaction mixture was stirred for 16 hours at room temperature. Dichloromethane was removed under vacuum and aq.HCl (3N) was added. The resulting solid was filtered and then redissolved in $CH_2Cl_2$ and washed with $NaHCO_3$ and brine, dried and evaporated under reduced pressure to afford a tan solid. $^1$H NMR (300 MHz) (DMSO-$d_6$) δ 9.75 (bs, 1H), 8.46 (bs, 1H), 7.49-7.26 (m, 4H), 6.96 (s, 1H).

The intermediates were prepared as follows.

a. Preparation of Compound

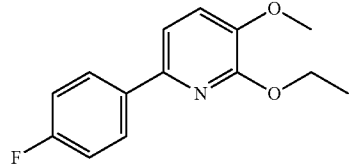 [SMILES: CCOc1nc(-c2ccc(F)cc2)ccc1OC]

To a solution of intermediate 9c (2-ethoxy-3-methoxy-6-iodopyridine) (140 mg, 0.5 mmol) in 4 ml dioxane:water (3:1) was added 4-(fluoro)phenylboronic acid (104 mg, 0.75 mmol) and potassium carbonate (138 mg, 1.0 mmol). The resulting mixture was degassed for 15 minutes after which Pd (PPh$_3$)$_4$ (60 mg, 0.06 mmol) was added and the mixture was further degassed for 15 minutes. The reaction mixture was then heated at 100° C. for 12 hours. After cooling to room temperature, the reaction mixture was diluted with ethyl acetate and was washed with saturated sodium bicarbonate, followed by brine. The organic phase was dried with sodium sulfate and concentrated under reduced pressure to afford crude product which was purified by ISCO flash chromatography using 10%-100% EtOAC in hexane to afford 120 mg product pure product (yield: 97%); $^1$H NMR (300 MHz, CDCl$_3$) δ: 7.97-7.92 (m, 2H), 7.26-7.05 (m, 4H), 4.59 (qt, J=6.9 Hz, 2H), 3.92 (s, 3H), 1.52 (t, J=7.0 Hz, 3H).

b. Preparation of Compound

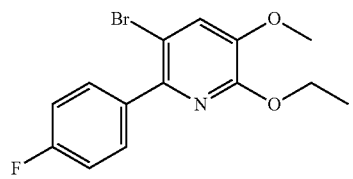 [SMILES: CCOc1nc(-c2ccc(F)cc2)c(Br)cc1OC]

To a mixture of 23a (2-ethoxy-3-methoxy-6-(4-fluorophenyl)pyridine) (120 mg, 0.48 mmol) in acetic acid (2.0 mL) was added sodium acetate (264 mg, 1.9 mmol). The reaction mixture was cooled to −32° C. and $Br_2$ (0.013 mL) in acetic acid (1.0 mL) was added dropwise. The reaction mixture was stirred at this temperature for 2 hours. The temperature of the cooling bath was raised to 0° C. and the stirring was continued for 1 hour. To this mixture 25% NaOH was added at 0° C. until pH 6 and then extracted with dichloromethane three times. Organic layer wad dried, concentrated and purified by ISCO using 10% EtOAC in hexane to afford a white solid as pure product 86 mg (55% yield). $^1$H NMR (300 MHz, MeOD-$d_4$) δ: 7.73-7.68 (m, 2H), 7.48 (s, 1H), 7.18-7.13 (m, 2H), 4.43 (qt, J=7.2 Hz, 2H), 3.90 (s, 3H), 1.40 (t, J=7.2 Hz, 3H). LC/MS: 326 (M+H).

Example 24

Preparation of Compound

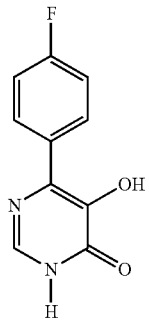 [SMILES: O=c1[nH]cnc(-c2ccc(F)cc2)c1O]

6-(4-Fluorophenyl)-5-hydroxypyrimidin-4(3H)-one 6-(4-Fluorophenyl)-5-methoxypyrimidin-4(3H)-one (107 mg, 0.49 mmol) was dissolved in anhydrous DCM (5 mL). The reaction mixture was cooled to 0° C. and the 1M in DCM $BBr_3$ (5 mL, 5 mmol) was added. It was then allowed to warm to room temperature and stirred for 24 hours. Then, the solvent was removed under reduced pressure. The resulting residue was diluted with EtOAc, which was washed with sat. $NaHCO_3$ followed by brine. The organic layer was dried over $Na_2SO_4$ followed by concentration under the vacuum. The residue was then flash chromatographed on silica gel eluting with 0-10% MeOH/DCM to provide 6-(4-fluorophenyl)-5-hydroxypyrimidin-4(3H)-one as a white solid (50 mg, 50%); m.p. 285-287° C.; $^1$H NMR (400 MHz, DMSO-$d_6$) δ 12.67 (bs, 1H), 9.83 (bs, 1H), 8.20 (dd, J=9 Hz, J=6 Hz, 2H), 7.87 (s, 1H), 7.29-7.25 (m, 2H); $^{13}$C NMR (100 MHz, DMSO-$d_6$) δ 161.9 ($J_{C,F}$=245 Hz), 158.7, 141.1, 138.5, 136.0, 132.3, 130.7 ($J_{C,F}$=8 Hz), 114.8 ($J_{C,F}$=21 Hz); $^{19}$F NMR (376 MHz, DMSO-$d_6$) δ −113.0;

a. Preparation of Compound

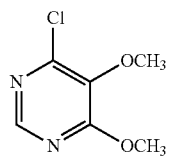 [SMILES: COc1ncnc(Cl)c1OC]

4-Chloro-5,6-dimethoxypyrimidine 4,6-Dichloro-5-methoxypyrimidine (300 mg, 1.68 mmol) was added to MeOH (10 mL). Then the reaction mixture was cooled to 0° C. It was treated with NaOMe (99 mg, 1.85 mmol) and allowed to warm to room temperature. The reaction mixture was then stirred for 19 hours at room temperature. After the reaction was completed, it was put under the vacuum to remove MeOH. The resulting residue was diluted with EtOAc, which was then washed with sat. $NH_4Cl$ followed by brine. The organic layer was dried over $Na_2SO_4$ and then concentrated. The residue was flash chromatographed on silica gel eluting with 0 to 10% EtOAc/Hexane to provide 4-chloro-5,6-dimethoxypyrimidine as a white solid (168 mg, 57%); m.p. 53-55° C.; $^1$H NMR (400 MHz, $CDCl_3$) δ 8.27 (s, 1H), 4.03 (s, 3H), 3.88 (s, 3H); $^{13}$C NMR (100 MHz, $CDCl_3$) δ 163.6, 151.6, 151.3, 138.2, 60.7, 54.8.

b. Preparation of Compound

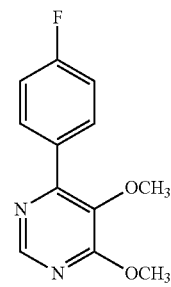 [SMILES: COc1ncnc(-c2ccc(F)cc2)c1OC]

4-(4-Fluorophenyl)-5,6-dimethoxypyrimidine

4-Chloro-4,5-dimethoxypyrimidine (165 mg, 0.95 mmol), (4-fluorophenyl)boronic acid (99 mg, 1.42 mmol), $Pd(PPh_3)_4$ (110 mg, 0.095 mmol) and $Na_2CO_3$ (300 mg, 2.84 mmol) were dissolved in a mixture of dioxane (9 mL) and water (3 mL). The air was evacuated and replaced with $N_2$. Then, the reaction mixture was refluxed for 19 hours. After the reaction was completed, it was cooled to room temperature and it was diluted with EtOAc and washed with sat. $NH_4Cl$ followed by brine. The organic layer was dried over $Na_2SO_4$ and concentrated under reduced pressure and the resulting residue was flash chromatographed on silica gel eluting with 0 to 10% EtOAc/Hexane. This afforded 4-(4-fluorophenyl)-5,6-dimethoxypyrimidine as a white solid (181 mg, 82%); m.p. 62-64° C.; $^1$H NMR (400 MHz, $CDCl_3$) δ 8.53 (s, 1H), 8.07 (dd, J=9 Hz, J=6 Hz, 2H), 7.15-7.11 (m, 2H), 4.07 (s, 3H), 3.73 (s, 3H); $^{13}$C NMR (100 MHz, $CDCl_3$) δ 163.7 ($J_{C,F}$=249 Hz), 164.0, 154.3, 152.0, 139.4, 131.4 ($J_{C,F}$=8 Hz), 131.3, 115.3 ($J_{C,F}$=21 Hz), 60.2, 54.2; $^{19}$F NMR (376 MHz, $CDCl_3$) δ −111.0;

c. Preparation of Compound

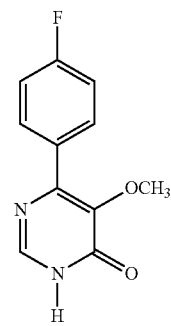 [SMILES: COc1c(-c2ccc(F)cc2)nc[nH]c1=O]

6-(4-Fluorophenyl)-5-methoxypyrimidin-4(3H)-one 4-(4-Fluorophenyl)-5,6-dimethoxypyrimidine (134 mg 0.57 mmol) was dissolved in a mixture of 2N HCl (5 mL) and dioxane (5 mL). The reaction mixture was then refluxed for 12 hours. It was then cooled to room temperature. The reaction mixture was put under the vacuum to remove the solvent, which gave white residue. This residue was diluted with water and filtered. The solid was collected and gave 6-(4-fluorophenyl)-5-methoxypyrimidin-4(3H)-one as a white solid (109 mg, 87%); m.p. 204-206° C.; $^1$H NMR (400 MHz, DMSO-d$_6$) δ 12.76 (s, 1H), 8.07 (s, 1H), 8.04 (dd, J=9 Hz, J=6 Hz, 2H), 7.33-7.28 (m, 2H), 3.34 (s, 3H); $^{13}$C NMR (100 MHz, DMSO-d$_6$) δ 162.5 ($J_{C,F}$=246 Hz), 158.8, 147.4, 143.7, 142.9, 131.7, 131.2 ($J_{C,F}$=8 Hz), 115.0 ($J_{C,F}$=21 Hz), 58.8; $^{19}$F NMR (376 MHz, DMSO-d$_6$) δ −111.8

Example 25

Preparation of Compound

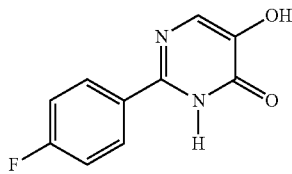 [SMILES: O=c1[nH]c(-c2ccc(F)cc2)ncc1O]

2-(4-Fluorophenyl)-5-hydroxypyrimidin-4(3H)-one 2-(4-Fluorophenyl)-5-methoxypyrimidin-4(3H)-one (58 mg, 0.26 mmol) was dissolved in anhydrous DCM (5 mL). The reaction mixture was cooled to 0° C. and the 1M in DCM BBr$_3$ (3 mL, 3 mmol) was added. It was then allowed to warm to room temperature and stirred for 24 hours. Then, the solvent was removed under reduced pressure. The resulting residue was suspended in water. It was filtered and the solid was collected and dried under vacuum to provide 2-(4-fluorophenyl)-5-hydroxypyrimidin-4(3H)-one as a white solid (23 mg, 42%); m.p. 252-254° C.; $^1$H NMR (400 MHz, DMSO-d$_6$) δ 12.88 (bs, 1H), 9.64 (bs, 1H), 8.05 (dd, J=9 Hz, J=5 Hz, 2H), 7.54 (s, 1H), 7.33-7.29 (m, 2H); $^{13}$C NMR (100 MHz, DMSO-d$_6$) δ 163.4 ($J_{C,F}$=246 Hz), 159.0, 146.9, 143.4, 131.7, 129.4 ($J_{C,F}$=9 Hz), 129.1, 115.5 ($J_{C,F}$=22 Hz); $^{19}$F NMR (376 MHz, DMSO-d$_6$) δ −110.5;

a. Preparation of Compound

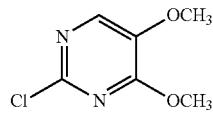

2-Chloro-4,5-dimethoxypyrimidine 2,4-Dichloro-5-methoxypyrimidine (2.37 g, 13.2 mmol) and K$_2$CO$_3$ (1.8 g, 13.2 mmol) were dissolved in MeOH (50 mL) and stirred for 19 hours at room temperature. The solvent was removed under reduced pressure. The resulting residue was dissolved in EtOAc and washed with distilled water followed by brine. The organic layer was dried over Na$_2$SO$_4$ and concentrated. It was then flash chromatographed on silica gel eluting with 0 to 20% EtOAc/Hexane to give 2-chloro-4,5-dimethoxypyrimidine as a white solid (1.70 g, 73%); m.p. 65-67° C.; $^1$H NMR (400 MHz, CDCl$_3$) δ 7.84 (s, 1H), 4.03 (s, 3H), 3.88 (s, 3H); $^{13}$C NMR (100 MHz, CDCl$_3$) δ 161.2, 150.0, 141.7, 138.2, 56.6, 55.0.

b. Preparation of Compound

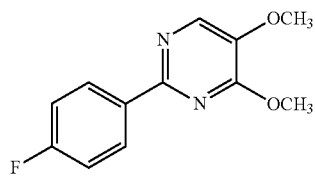 [SMILES: COc1cnc(-c2ccc(F)cc2)nc1OC]

2-(4-Fluorophenyl)-4,5-dimethoxypyrimidine

2-Chloro-4,5-dimethoxypyrimidine (500 mg, 2.86 mmol), (4-fluorophenyl)boronic acid (601 mg, 4.30 mmol), Pd(PPh$_3$)$_4$ (330 mg, 0.29 mmol) and Na$_2$CO$_3$ (910 mg, 8.59 mmol) were dissolved in a mixture of dioxane (12 mL) and water (4 mL). The air was evacuated and replaced with N$_2$. Then, the reaction mixture was refluxed for 5 hours. After the reaction was completed, it was cooled to room temperature and it was diluted with EtOAc and washed with sat. NH$_4$Cl followed by brine. The organic layer was dried over Na$_2$SO$_4$ and concentrated under reduced pressure and the resulting residue was flash chromatographed on silica gel eluting with 0 to 10% EtOAc/Hexane. This afforded 2-(4-fluorophenyl)-4,5-dimethoxypyrimidine as a white solid (123 mg, 77%); m.p. 114-116° C.; $^1$H NMR (400 MHz, CDCl$_3$) δ 8.37 (dd, J=9 Hz, J=6 Hz, 2H), 8.12 (s, 1H), 7.16-7.12 (m, 2H), 4.17 (s, 3H), 3.98 (s, 3H); $^{13}$C NMR (100 MHz, CDCl$_3$) δ 163.1 ($J_{C,F}$=248 Hz), 159.7, 155.3, 141.0, 137.2, 133.6 ($J_{C,F}$=3 Hz), 129.6 ($J_{C,F}$=8 Hz), 115.3 ($J_{C,F}$=22 Hz), 56.4, 54.0; $^{19}$F NMR (376 MHz, CDCl$_3$) δ −111.9.

c. Preparation of Compound

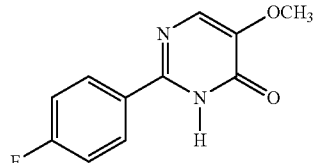

2-(4-Fluorophenyl)-5-methoxypyrimidin-4(3H)-one 2-(4-Fluorophenyl)-4,5-dimethoxypyrimidine (187 mg, 0.799 mmol) was dissolved in a mixture of 2N HCl (5 mL) and dioxane (5 mL). The reaction mixture was then refluxed for 12 hours. It was then cooled to room temperature. The reaction mixture was diluted with EtOAc and washed with sat. NaHCO$_3$ followed by brine. The organic layer was dried over Na$_2$SO$_4$ and concentrated. The resulting residue was flash chromatographed on silica gel eluting with 50% to 100% EtOAc/Hexane to give 2-(4-fluorophenyl)-5- methoxypyrimidin-4(3H)-one as white solid (41 mg, 23%); m.p. 229-231° C.; $^1$H NMR (400 MHz, DMSO-d$_6$) δ12.79 (s, 1H), 7.68 (s, 1H), 8.08 (dd, J=9 Hz, J=5 Hz, 2H), 7.35-7.30 (m, 2H), 3.79 (s, 3H); $^{13}$C NMR (100 MHz, DMSO-d$_6$) δ 163.6 (J$_{C,F}$=247 Hz), 158.1, 148.4, 145.4, 130.4, 129.6 (J$_{C,F}$=9 Hz), 129.1, 115.5 (J$_{C,F}$=22 Hz), 56.0; $^{19}$F NMR (376 MHz, DMSO-d$_6$) δ −110.2.

Example 26

Preparation of Compound

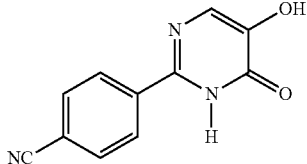 [SMILES: N#Cc1ccc(-c2ncc(O)c(=O)[nH]2)cc1]

4-(5-hydroxy-6-oxo-1,6-dihydropyrimidin-2-yl)benzonitrile 4-(5-Methoxy-6-oxo-1,6-dihydropyrimidin-2-yl)benzonitrile (50 mg, 0.22 mmol) was dissolved in anhydrous DCM (5 mL). The reaction mixture was cooled to 0° C. and the 1M in DCM BBr$_3$ (2.2 mL, 2.2 mmol) was added. It was then allowed to warm to room temperature and stirred for 18 hours. Then, the solvent was removed under reduced pressure. The resulting residue was suspended in water. It was filtered and the solid was collected and dried under vacuum to provide 4-(5-hydroxy-6-oxo-1,6-dihydropyrimidin-2-yl)benzonitrile as a white solid (15 mg, 32%); m.p. 324-326° C.; $^1$H NMR (400 MHz, DMSO-d$_6$) δ 13.05 (bs, 1H), 9.91 (bs, 1H), 8.18 (d, J=8 Hz, 2H), 7.95 (d, J=8 Hz, 2H), 7.64 (s, 1H); $^{13}$C NMR (100 MHz, DMSO-d$_6$) δ 158.8, 132.5, 129.4, 127.6, 127.2, 127.1, 126.7, 118.4, 112.5.

a. Preparation of Compound

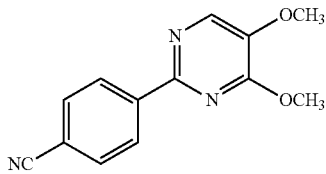 [SMILES: COc1cnc(-c2ccc(C#N)cc2)nc1OC]

4-(4,5-dimethoxypyridin-2-yl)benzonitrile

2-Chloro-4,5-dimethoxypyrimidine (100 mg, 0.57 mmol), (4-cyanophenyl)boronic acid (126 mg, 0.86 mmol), Pd(PPh$_3$)$_4$ (66 mg, 0.06 mmol) and Na$_2$CO$_3$ (182 mg, 1.72 mmol) were dissolved in a mixture of dioxane (9 mL) and water (3 mL). The air was evacuated and replaced with N$_2$. Then, the reaction mixture was refluxed for 4 hours. After the reaction was completed, it was cooled to room temperature and it was diluted with EtOAc and washed with sat. NH$_4$Cl followed by brine. The organic layer was dried over Na$_2$SO$_4$ and concentrated in vacuo and the resulting residue was flash chromatographed on silica gel eluting with 0 to 20% EtOAc/hexane. This afforded 4-(4,5-dimethoxypyrimidin-2-yl)benzonitrile as a white solid (69 mg, 74%); m.p. 170-172° C.; $^1$H NMR (400 MHz, CDCl$_3$) δ 8.49 (d, J=9 Hz, 2H), 8.18 (s, 1H), 7.76 (d, J=9 Hz, 2H), 4.20 (s, 3H), 4.02 (s, 3H); $^{13}$C NMR (100 MHz, CDCl$_3$) δ 159.8, 154.0, 141.8, 141.5, 137.0, 132.3, 128.0, 119.0, 113.0, 56.4, 54.2.

b. Preparation of Compound

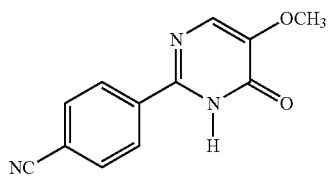 [SMILES: COc1cnc(-c2ccc(C#N)cc2)[nH]c1=O]

4-(5-Methoxy-6-oxo-1,6-dihydropyrimidin-2-yl)benzonitrile 4-(4,5-Dimethoxypyrimidin-2-yl)benzonitrile (53 mg, 0.22 mmol) was dissolved in a mixture of 2N HCl (5 mL) and dioxane (5 mL). The reaction mixture was then refluxed for 5 hours. It was then cooled to room temperature. The reaction mixture was diluted with EtOAc and washed with sat. NaHCO$_3$ followed by brine. The organic layer was dried over Na$_2$SO$_4$ and concentrated. The resulting residue was flash chromatographed on silica gel eluting with 0 to 5% MeOH/DCM to give 4-(5-methoxy-6-oxo-1,6-dihydropyrimidin-2-yl)benzonitrile as a white solid (50 mg, 100%); m.p. 297-299° C.; $^1$H NMR (400 MHz, DMSO-d$_6$) δ 12.99 (bs, 1H), 8.19 (d, J=8 Hz, 2H), 7.96 (d, J=8 Hz, 2H), 7.75 (s, 1H), 3.81 (s, 3H); $^{13}$C NMR (100 MHz, DMSO-d$_6$) 157.8, 147.4, 146.2, 136.5, 132.5, 130.0, 127.8, 118.4, 112.8, 56.1.

Example 27

Preparation of Compound

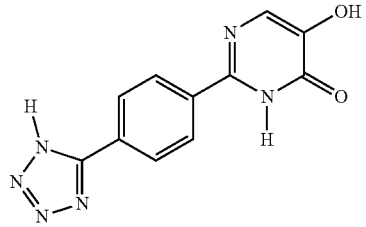 [SMILES: O=c1[nH]c(-c2ccc(-c3nnn[nH]3)cc2)ncc1O]

2-(4-(1H-Tetrazol-5-yl)phenyl)-5-hydroxypyrimidin-4(3H)-one 4-(5-Hydroxy-6-oxo-1,6-dihydropyrimidin-2-yl)benzonitrile (68 mg, 0.32 mmol) and NaN$_3$ (79 mg, 1.21 mmol) were dissolved in anhydrous DMF (1 mL). The reaction mixture was treated with 2 drops of acetic acid. It was sealed and then it was heated at 130° C. for 17 hours. The reaction was cooled to room temperature and gave brownish suspension. DMF was removed by Kugelrohr distillation. The resulting residue was suspended in water and filtered to give 2-(4-

(1H-tetrazol-5-yl)phenyl)-5-hydroxypyrimidin-4(3H)-one as a dark brown solid (42 mg, 51%); ¹H NMR (400 MHz, DMSO-d₆) δ 8.08 (d, J=9 Hz, 2H), 8.03 (d, J=8 Hz, 2H), 7.55 (s, 1H).

Example 28

Preparation of Compound

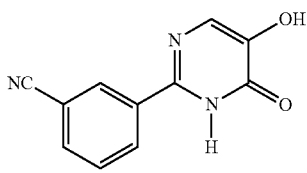 [SMILES: N#Cc1cccc(-c2ncc(O)c(=O)[nH]2)c1]

3-(5-Hydroxy-6-oxo-1,6-dihydropyrimidin-2-yl)benzonitrile 3-(5-Methoxy-6-oxo-1,6-dihydropyrimidin-2-yl)benzonitrile (50 mg, 0.219 mmol) was dissolved in anhydrous DCM (5 mL). The reaction mixture was cooled to 0° C. and the 1M in DCM BBr₃ (2.2 mL, 2.2 mmol) was added. It was then allowed to warm to room temperature and stirred for 18 hours. Then, the solvent was removed under reduced pressure. The resulting residue was suspended in water. It was filtered and the solid was collected and dried under vacuum to provide 3-(5-hydroxy-6-oxo-1,6-dihydropyrimidin-2-yl)benzonitrile as a white solid (27 mg, 58%); m.p. 294-296° C.; ¹H NMR (400 MHz, DMSO-d₆) δ 8.44 (s, 1H), 8.35 (d, J=8 Hz, 1H), 7.93 (d, J=8 Hz, 1H), 7.68 (t, J=8 Hz, 1H), 7.61 (s, 1H); ¹³C NMR (100 MHz, DMSO-d₆) δ 159.3, 146.4, 143.9, 134.3, 133.4, 131.9, 131.5, 130.4, 129.8, 118.4, 111.7.

a. Preparation of Compound

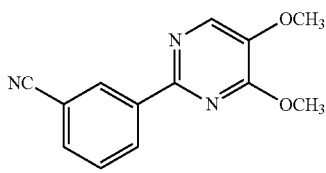 [SMILES: COc1cnc(-c2cccc(C#N)c2)nc1OC]

3-(4,5-Dimethoxypyrimidin-2-yl)benzonitrile

2-Chloro-4,5-dimethoxypyrimidine (100 mg, 0.57 mmol), (3-cyanophenyl)boronic acid (126 mg, 0.86 mmol), Pd(PPh₃)₄ (66 mg, 0.06 mmol) and Na₂CO₃ (182 mg, 1.72 mmol) were dissolved in a mixture of dioxane (9 mL) and water (3 mL). The air was evacuated and replaced with N₂. Then, the reaction mixture was refluxed for 5 hours. After the reaction was completed, it was cooled to room temperature and it was diluted with EtOAc and washed with sat. NH₄Cl followed by brine. The organic layer was dried over Na₂SO₄ and concentrated in vacuo and the resulting residue was flash chromatographed on silica gel eluting with 0 to 20% EtOAc/Hexane. This afforded 3-(4,5-dimethoxypyrimidin-2-yl)benzonitrile as a white solid (138 mg, 100%); m.p. 134-136° C.; ¹H NMR (400 MHz, CDCl₃) δ 8.61 (s, 1H), 8.54 (d, J=8 Hz, 1H), 8.09 (s, 1H), 7.65 (d, J=8 Hz, 1H), 7.51 (t, J=8 Hz, 1H), 4.13 (s, 3H), 3.95 (s, 3H); ¹³C NMR (100 MHz, CDCl₃) δ 159.8, 153.6, 141.7, 138.5, 137.0, 132.8, 131.6, 131.3, 129.2, 118.9, 112.6, 56.4, 54.2.

b. Preparation of Compound

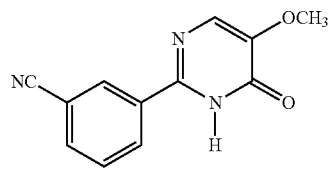 [SMILES: COc1cnc(-c2cccc(C#N)c2)[nH]c1=O]

3-(5-Methoxy-6-oxo-1,6-dihydropyrimidin-2-yl)benzonitrile 3-(4,5-Dimethoxypyrimidin-2-yl)benzonitrile (138 mg, 0.57 mmol) was dissolved in a mixture of 2N HCl (5 mL) and dioxane (5 mL). The reaction mixture was then refluxed for 6 hours. It was then cooled to room temperature. The reaction mixture was diluted with EtOAc and washed with sat. NaHCO₃ followed by brine. The organic layer was dried over Na₂SO₄ and concentrated. The resulting residue was flash chromatographed on silica gel eluting with 0 to 10% MeOH/DCM to give 3-(5-methoxy-6-oxo-1,6-dihydropyrimidin-2-yl)benzonitrile as a white solid (56 mg, 43%); m.p. 255-257° C.; ¹H NMR (400 MHz, DMSO-d₆) δ 12.93 (bs, 1H), 8.44 (s, 1H), 8.34 (d, J=8 Hz, 1H), 7.99 (d, J=8 Hz, 1H), 7.74-7.70 (m, 2H), 3.82 (s, 3H); ¹³C NMR (100 MHz, DMSO-d₆) δ 157.9, 147.5, 145.9, 133.9, 133.7, 131.7, 130.7, 130.4, 129.9, 118.3, 111.7, 56.1.

Example 29

Preparation of Compound

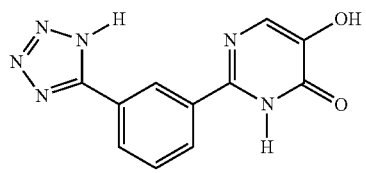 [SMILES: O=c1[nH]c(-c2cccc(-c3nnn[nH]3)c2)ncc1O]

2-(3-(1H-tetrazol-5-yl)phenyl)-5-hydroxypyrimidin-4(3H)-one 3-(5-Hydroxy-6-oxo-1,6-dihydropyrimidin-2-yl)benzonitrile (108 mg, 0.50 mmol) and NaN₃ (131 mg, 2.02 mmol) were dissolved in anhydrous DMF (1 mL). The reaction mixture was treated with 2 drops of acetic acid. It was sealed and then it was heated at 130° C. for 18 hours. The reaction was cooled to room temperature and gave brownish suspension. It was filtered and greenish solid was obtained. The greenish solid was suspended in 2N HCl followed by second filtration to provide 2-(3-(1H-tetrazol-5-yl)phenyl)-5-hydroxypyrimidin-4(3H)-one as a beige solid (32 mg, 25%); ¹H NMR (400 MHz, DMSO-d₆) δ 8.67 (s, 1H), 8.11 (d, J=8 Hz, 1H), 7.97 (d, J=8 Hz, 1H), 7.63 (s, 1H), 7.56 (t, J=8 Hz, 1H); ¹³C NMR (100 MHz, DMSO-d₆) δ162.3, 159.1, 158.7, 148.0, 143.4, 133.1, 130.4, 128.9, 127.9, 126.5, 125.1.

Example 30

Preparation of Compound

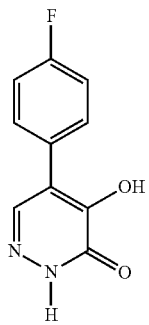 [SMILES: O=c1[nH]ncc(-c2ccc(F)cc2)c1O]

5-(4-Fluorophenyl)-4-hydroxypyridazin-3(2H)-one 5-(4-Fluorophenyl)-4-methoxy-2-(methoxymethyl) pyridazin-3(2H)-one (55 mg, 0.21 mmol) was dissolve in anhydrous DCM (10 mL). The reaction mixture was cooled to 0° C. and the 1M in DCM BBr$_3$ (2.1 mL, 2.1 mmol) was added. It was then allowed to warm to room temperature and stirred for 24 hours. Then, the solvent was removed under reduced pressure. This gave 5-(4-fluorophenyl)-4-methoxy-pyridazin-3(2H)-one, which was again recharged with 1M in DCM BBr$_3$ (2.1 mL, 2.1 mmol). The reaction mixture was stirred for 24 hours at room temperature. Then, the solvent was again removed under reduced pressure. The resulting residue was suspended with water and filtered. The filtered solid was then flash chromatographed on silica gel eluting with 0-10% MeOH/DCM. This gave 5-(4-fluorophenyl)-4-hydroxypyridazin-3(2H)-one as a white solid (6.2 mg, 14%); m.p. 274-276° C.; $^1$H NMR (400 MHz, DMSO-d$_6$) δ 12.70 (s, 1H), 7.76 (s, 1H), 7.58 (J=8 Hz, J=5 Hz, 2H), 7.21-7.17 (m, 2H); $^{13}$C NMR (100 MHz, DMSO-d$_6$) δ 161.2 (J$_{C,F}$=243 Hz), 161.9, 154.6, 132.7, 132.4 (J$_{C,F}$=8 Hz), 127.2 (J$_{C,F}$=4 Hz), 115.8, 114.2 (J$_{C,F}$=21 Hz); $^{19}$F NMR (376 MHz, DMSO-d$_6$) δ -114.1 a. Preparation of Compound

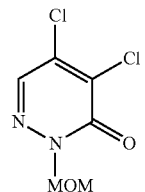

4,5-Dichloro-2-(methoxymethyl)pyridazin-3(2H)-one 4,5-Dichloropyridazin-3(2H)-one (200 mg, 1.21 mmol) and 4-Dimethylaminopyridine (15 mg, 0.12 mmol) were dissolved in anhydrous DCM (20 mL). Then, the reaction mixture was cooled to 0° C. and treated with NEt$_3$ (0.29 mL, 1.70 mmol) followed by MOM-Cl (0.110 mL, 1.454 mmol). The reaction mixture was allowed to warm to room temperature and stirred for 17 hours. It was then poured into DCM and it was washed with sat. NH$_4$Cl followed by brine. The organic layer was dried over Na$_2$SO$_4$, which was concentrated. The resulting residue was flash chromatographed on silica gel eluting with 0 to 30% EtOAc/Hexane to provide 4,5-dichloro-2-(methoxymethyl)pyridazin-3 (2H)-one as a white solid (84 mg, 33%); m.p. 65-67° C.; $^1$H NMR (400 MHz, CDCl$_3$) δ 7.78 (s, 1H), 5.41 (s, 2H), 3.43 (s, 3H); $^{13}$C NMR (100 MHz, CDCl$_3$) δ 156.9, 137.0, 136.0, 134.9, 82.4, 58.1.

b. Preparation of Compound

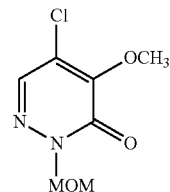

5-Chloro-4-methoxy-2-(methoxymethyl)pyridazin-3 (2H)-one 4,5-Dichloro-2-(methoxymethyl)pyridazin-3(2H)-one (84 mg, 0.40 mmol) was added to MeOH (10 mL). Then the reaction mixture was cooled to 0° C. It was treated with NaOMe (24 mg, 0.442 mmol) and allowed to warm to room temperature. The reaction mixture was then stirred for 18 hours at room temperature. After the reaction was completed, it was put under the vacuum to remove MeOH. The resulting residue was diluted with EtOAc, which was then washed with sat. NH$_4$Cl followed by brine. The organic layer was dried over Na$_2$SO$_4$ and then concentrated. The residue was flash chromatographed on silica gel eluting with 0 to 30% EtOAc/Hexane to provide 5-chloro-4-methoxy-2-(methoxymethyl)pyridazin-3(2H)-one as a white solid (59 mg, 72%); m.p. 101-103° C.; $^1$H NMR (400 MHz, CDCl$_3$) δ 7.85 (s, 1H), 5.45 (s, 2H), 4.08 (s, 3H), 3.44 (s, 3H); $^{13}$C NMR (100 MHz, CDCl$_3$) δ 159.1, 155.1, 127.1, 116.9, 81.9, 57.9, 57.8.

c. Preparation of Compound

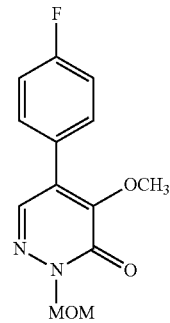

5-(4-Fluorophenyl)-4-methoxy-2-(methoxymethyl)pyridazin-3(2H)-one

5-Chloro-4-methoxy-2-(methoxymethyl)pyridazin-3(2H)-one (58 mg, 0.28 mmol), (4-fluorophenyl)boronic acid (140 mg, 0.43 mmol), Pd(PPh$_3$)$_4$ (32 mg, 0.028 mmol) and Na$_2$CO$_3$ (90 mg, 0.85 mmol) were dissolved in a mixture of dioxane (9 mL) and water (3 mL). The air was evacuated and replaced with N$_2$. Then, the reaction mixture was refluxed for 14 hours. After the reaction was completed, it was cooled to room temperature and it was diluted with EtOAc and washed with sat. NH$_4$Cl followed by brine. The organic layer was dried over Na$_2$SO$_4$ and concentrated in vacuo and the resulting residue was flash chromatographed on silica gel eluting with 0 to 30% EtOAc/Hexane. This afforded 5-(4-fluorophenyl)-4-methoxy-2-(methoxymethyl)pyridazin-3(2H)-one as a white solid (56 mg, 74%); m.p. 123-125° C.; $^1$H NMR (400 MHz, CDCl$_3$) δ 7.95 (s, 1H), 7.53 (dd, J=9 Hz, J=6 Hz, 2H), 7.11-7.07 (m, 2H), 5.48 (s, 2H), 3.93 (s, 3H), 3.49 (s, 3H); $^{13}$C NMR (100 MHz, CDCl$_3$) δ 162.6 (J$_{C,F}$=247 Hz), 161.6, 154.8, 132.3 (J$_{C,F}$=8 Hz), 128.5, 125.7, 120.7, 112.9 (J$_{C,F}$=22 Hz), 81.6, 57.9, 57.3; $^{19}$F NMR (376 MHz, CDCl$_3$) δ −112.6.

Example 31

Preparation of Compound

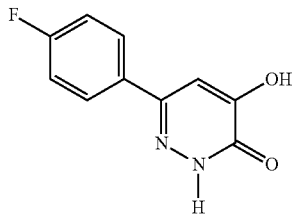 [SMILES: O=c1[nH]nc(-c2ccc(F)cc2)cc1O]

6-(4-Fluorophenyl)-4-hydroxypyridazin-3(2H)-one 6-(4-Fluorophenyl)-4-methoxypyridazin-3(2H)-one (16 mg, 0.074 mmol) was dissolve in anhydrous DCM (5 mL). The reaction mixture was cooled to 0° C. and the 1M in DCM BBr$_3$ (0.74 mL, 0.74 mmol) was added. It was then allowed to warm to room temperature and stirred for 36 hours. Then, the solvent was removed under reduced pressure. The resulting residue was suspended in water. It was filtered and the solid was collected and dried under vacuum to provide 6-(4-fluorophenyl)-4-hydroxypyridazin-3(2H)-one as a white solid (5 mg, 35%); m.p. 281-283° C.; $^1$H NMR (400 MHz, DMSO-d$_6$) δ 13.10 (bs, 1H), 11.02 (bs, 1H), 7.87 (dd, J=9 Hz, J=5 Hz, 2H), 7.30-7.26 (m, 2H), 7.19 (s, 1H); $^{13}$C NMR (100 MHz, DMSO-d$_6$) δ 162.6 (J$_{C,F}$=245 Hz), 157.6, 155.4, 145.2, 132.0 (J$_{C,F}$=3 Hz), 128.0 (J$_{C,F}$=9 Hz), 115.6 (J$_{C,F}$=22 Hz), 106.0; $^{19}$F NMR (376 MHz, DMSO-d$_6$) δ −113.0.

a. Preparation of Compound

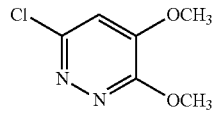

6-Chloro-3,4-dimethoxypyridazine 3,4,6-Trichloropyridazine (200 mg, 1.09 mmol) was added to MeOH (15 mL). Then the reaction mixture was cooled to 0° C. It was treated with NaOMe (117 mg, 2.17 mmol) and allowed to warm to room temperature. The reaction mixture was then stirred for 10 hours at room temperature. After the reaction was completed, it was put under the vacuum to remove MeOH. The resulting residue was diluted with EtOAc, which was then washed with sat. NH$_4$Cl followed by brine. The organic layer was dried over Na$_2$SO$_4$ and then concentrated. The residue was flash chromatographed on silica gel eluting with 0 to 30% EtOAc/Hexane to provide 4-chloro-5,6-dimethoxypyrimidine as a white solid (101 mg, 53%); m.p. 117-119° C.; $^1$H NMR (400 MHz, CDCl$_3$) δ 6.71 (s, 1H), 4.08 (s, 3H), 3.88 (s, 3H); $^{13}$C NMR (100 MHz, CDCl$_3$) δ 156.9, 151.1, 149.8, 108.4, 56.2, 55.3.

b. Preparation of Compound

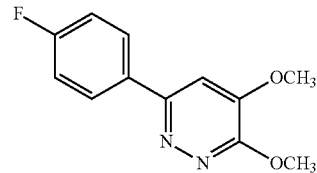 [SMILES: COc1cc(-c2ccc(F)cc2)nnc1OC]

6-(4-Fluorophenyl)-3,4-dimethoxypyridazine

6-Chloro-3,4-dimethoxypyridazine (101 mg, 0.58 mmol), (4-fluorophenyl)boronic acid (122 mg, 0.87 mmol), Pd(PPh$_3$)$_4$ (67 mg, 0.06 mmol) and Na$_2$CO$_3$ (184 mg, 1.74 mmol) were dissolved in a mixture of dioxane (15 mL) and water (5 mL). The air was evacuated and replaced with N$_2$. Then, the reaction mixture was refluxed for 3 hours. After the reaction was completed, it was cooled to room temperature and it was diluted with EtOAc and washed with sat. NH$_4$Cl followed by brine. The organic layer was dried over Na$_2$SO$_4$ and concentrated under reduced pressure and the resulting residue was flash chromatographed on silica gel eluting with 0 to 20% EtOAc/Hexane. This afforded 6-(4-fluorophenyl)-3,4-dimethoxypyridazine as a white solid (109 mg, 80%); m.p. 103-105° C.; $^1$H NMR (400 MHz, CDCl$_3$) δ 7.88 (dd, J=9 Hz, J=5 Hz, 2H), 7.10-7.06 (m, 2H), 7.00 (s, 1H), 4.14 (s, 3H), 3.93 (s, 3H); $^{13}$C NMR (100 MHz, CDCl$_3$) δ 163.7 (J$_{C,F}$=247 Hz), 156.5, 155.7, 148.9, 132.9 (J$_{C,F}$=3 Hz), 128.5 (J$_{C,F}$=9 Hz), 115.8 (J$_{C,F}$=21 Hz), 104.7, 55.7, 55.2; $^{19}$F NMR (376 MHz, CDCl$_3$) δ −112.2.

c. Preparation of Compound

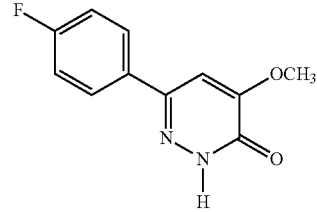 [SMILES: COc1cc(-c2ccc(F)cc2)n[nH]c1=O]

6-(4-Fluorophenyl)-4-methoxypyridazin-3(2H)-one 6-(4-Fluorophenyl)-3,4-dimethoxypyridazine (122 mg, 0.52 mmol) was dissolved in a mixture of 2N HCl (5 mL) and dioxane (5 mL). The reaction mixture was then refluxed for 11 hours. It was then cooled to room temperature. The reaction mixture was diluted with EtOAc and washed with sat. NaHCO$_3$ followed by brine. The organic layer was dried over Na$_2$SO$_4$ and concentrated. The resulting residue was flash chromatographed on silica gel eluting with 0 to 10% MeOH/DCM to give 6-(4-fluorophenyl)-4-methoxypyridazin-3(2H)-one as a white solid (41 mg, 36%); m.p. 211-213° C.; $^1$H NMR (400 MHz, DMSO-d$_6$) δ 13.05 (br s, 1H), 7.96 (dd, J=9 Hz, J=6 Hz, 2H), 7.34-7.29 (m, 2H), 7.28 (s, 1H), 3.92 (s, 3H); $^{13}$C NMR (100 MHz, DMSO-d$_6$) δ 162.7 (J$_{C,F}$=245 Hz), 156.2, 155.7, 144.3, 132.0 (J$_{C,F}$=3 Hz), 128.2 (J$_{C,F}$=8 Hz), 115.6 (J$_{C,F}$=22 Hz), 104.4, 56.2; $^{19}$F NMR (376 MHz, DMSO-d$_6$) δ −112.9.

Example 32

Preparation of Compound

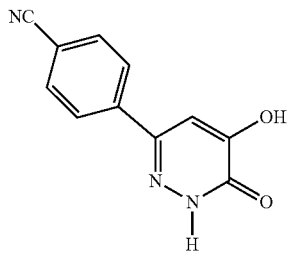 [SMILES: N#Cc1ccc(-c2cc(O)c(=O)[nH]n2)cc1]

4-(5-Hydroxy-6-oxo-1,6-dihydropyridazin-3-yl)benzonitrile 4-(5-Methoxy-6-oxo-1,6-dihydropyridazin-3-yl)benzonitrile (109 mg, 0.48 mmol) was dissolved in anhydrous DCM (5 mL). The reaction mixture was cooled to 0° C. and the 1M in DCM BBr$_3$ (4.8 mL, 4.8 mmol) was added. It was then allowed to warm to room temperature and stirred for 20 hours. Then, the solvent was removed under reduced pressure. The resulting residue was suspended in water. It was filtered and the solid was collected. The solid was dry loaded on silica gel and flash chromatographed eluting with 0 to 10% MeOH/DCM. This afforded 4-(5-hydroxy-6-oxo-1,6-dihydropyridazin-3-yl)benzonitrile as a white solid (75 mg, 73%); m.p. 305-307° C.; $^1$H NMR (400 MHz, DMSO-d$_6$) δ 13.29 (s, 1H), 11.15 (bs, 1H), 8.03 (d, J=9 Hz, 2H), 7.92 (d, J=9 Hz, 2H), 7.29 (s, 1H); $^{13}$C NMR (100 MHz, DMSO-d$_6$) δ 157.7, 154.6, 144.4, 139.8, 132.7, 126.5, 118.6, 111.4, 106.0 a. Preparation of Compound

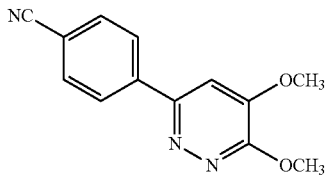 [SMILES: COc1cc(-c2ccc(C#N)cc2)nnc1OC]

4-(5,6-Dimethoxypyridazin-3-yl)benzonitrile

6-Chloro-3,4-dimethoxypyridazine (298 mg, 1.71 mmol), (4-cyanophenyl)boronic acid (376 mg, 2.56 mmol), Pd(PPh$_3$)$_4$ (198 mg, 0.17 mmol) and Na$_2$CO$_3$ (543 mg, 5.12 mmol) were dissolved in a mixture of dioxane (15 mL) and water (5 mL). The air was evacuated and replaced with N$_2$. Then, the reaction mixture was refluxed for 15 hours. After the reaction was completed, it was cooled to room temperature and it was diluted with EtOAc and washed with sat. NH$_4$Cl followed by brine. The organic layer was dried over Na$_2$SO$_4$ and concentrated under reduced pressure and the resulting residue was flash chromatographed on silica gel eluting with 0 to 30% EtOAc/Hexane. This afforded 4-(5,6-dimethoxypyridazin-3-yl)benzonitrile as a white solid (130 mg, 31%); m.p. 187-189° C.; $^1$H NMR (400 MHz, CDCl$_3$) δ 8.10 (d, J=8 Hz, 2H), 7.77 (d, J=8 Hz, 2H), 7.14 (s, 1H), 4.23 (s, 3H), 4.03 (s, 3H); $^{13}$C NMR (100 MHz, CDCl$_3$) δ 157.1, 154.7, 149.1, 140.9, 132.6, 127.3, 118.5, 113.0, 104.9, 55.9, 55.3.

b. Preparation of Compound

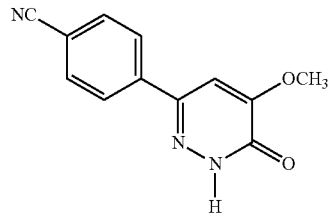 [SMILES: COc1cc(-c2ccc(C#N)cc2)n[nH]c1=O]

4-(5-Methoxy-6-oxo-1,6-dihydropyridazin-3-yl)benzonitrile 4-(5,6-Dimethoxypyridazin-3-yl)benzonitrile (125 mg, 0.52 mmol) was dissolved in a mixture of 2N HCl (5 mL) and dioxane (5 mL). The reaction mixture was then refluxed for 4 hours. It was then cooled to room temperature and then put under reduced pressure. The resulting residue was suspended in water and filtered. The product 4-(5-methoxy-6-oxo-1,6-dihydropyridazin-3-yl)benzonitrile was collected as a white solid (82 mg, 70%); m.p. 271-273° C.; $^1$H NMR (400 MHz, DMSO-d$_6$) δ 13.97 (bs, 1H), 8.02 (d, J=8 Hz, 2H), 7.94 (d, J=8 Hz, 2H), 6.62 (s, 1H), 3.96 (s, 3H).

Example 33

Preparation of Compound

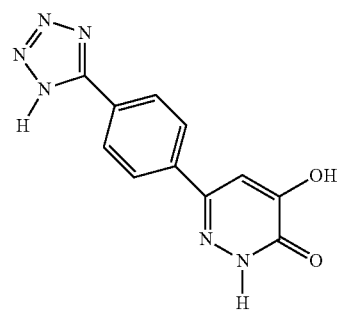

6-(4-(1H-Tetrazol-5-yl)phenyl)-4-hydroxypyridazin-3(2H)-one 4-(5-Methoxy-6-oxo-1,6-dihydropyridazin-3-yl)benzonitrile (56 mg, 0.26 mmol) and NaN$_3$ (69 mg, 1.06 mmol) were dissolved in anhydrous DMF (1 mL). The reaction mixture was treated with 2 drops of acetic acid. It was sealed and then it was heated at 130° C. for 21 hours. The reaction was cooled to room temperature and gave brownish suspension. The suspension was filtered and gave a white solid, which was treated with 2N HCl and filtered again. This afforded 6-(4-(1H-tetrazol-5-yl)phenyl)-4-hydroxypyridazin-3(2H)-one as a white solid (33 mg, 48%); $^1$H NMR (400 MHz, DMSO-d$_6$) δ 11.13 (s, 1H), 8.09 (d, J=8 Hz, 2H), 7.95 (d, J=7 Hz, 2H), 7.25 (s, 1H).

Example 34

Preparation of Compound

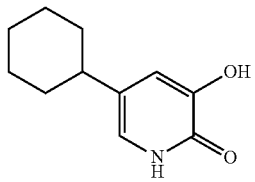 [SMILES: O=c1[nH]cc(C2CCCCC2)cc1O]

5-Cyclohexyl-3-hydroxypyridin-2(1H)-one

To a solution of 2-ethoxy-3-methoxy-5-cyclohexylpyridinepyridine (30 mg, 0.13 mmol) in CH$_2$Cl$_2$ (2.0 ml) under nitrogen, was added boron tribromide (0.5 ml of a 1.0 M solution in CH$_2$Cl$_2$). After addition was completed, the reaction mixture was stirred for 16 h at room temperature. Dichloromethane was removed from the reaction mixture followed by addition of HCl (3N). The resulting solid was filtered. The solid was redissolved in CH$_2$Cl$_2$ and washed with NaHCO$_3$ and brine. The organic phase was then dried and evaporated under reduced pressure to afford the product (22 mg) as solid, yield: 90%. $^1$H NMR (300 MHz, DMSO-d$_6$) δ: 6.65 (s, 1H), 6.55 (s, 1H), 2.2 (m, 1H), 1.7 (m, 5H), 1.35 (m, 5H).

The requisite intermediate was prepared as follows a. Preparation of Compound

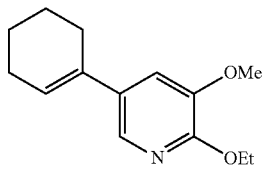 [SMILES: CCOc1ncc(C2=CCCCC2)cc1OC]

A mixture of 5-bromo-2-ethoxy-3-methoxypyridine (279 mg, 1.0 mmol), 1-cyclohexenyl boronic acid pinacole ester (250 mg, 1.2 mmol), Pd(PPh$_3$)$_4$ (139 mg, 0.12 mmol) and K$_2$CO$_3$ (277 mg, 2.0 mmol) in 1,4-dioxane (3.0 ml) and H$_2$O (1.0 ml) was degassed for 30 min. This mixture was heated to 100° C. and stirred for 16 h. The reaction mixture was cooled to room temperature and partitioned between NaHCO$_3$ and EtOAc (3×), and washed with NaCl (1×). The organic phase was dried over Na$_2$SO$_4$ and was concentrated. The resulting residue was purified by ISCO flash chromatography using 10% EtOAc in hexane to give 551 mg (97%) of the desired product. $^1$H NMR (300 MHz, CDCl$_3$) δ: 7.7 (s, 1H), 7.04 (s, 1H), 6.0 (m, 1H), 4.4 (qt, 2H), 3.84 (s, 3H), 2.36 (m, 2H), 2.18 (m, 2H), 1.78 (m, 2H), 1.7 (m, 2H), 1.4 (t, 3H).

b. Preparation of Compound

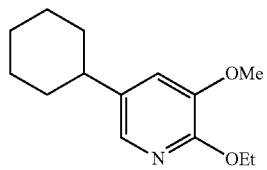 [SMILES: CCOc1ncc(C2CCCCC2)cc1OC]

To a solution of 5-cyclohexenyl-2-ethoxy-3-methoxypyridine (200 mg, 0.86 mmol) in methanol (10 ml) was added catalytic amount of Pd/C. The mixture was evacuated three times and then was charged with hydrogen in a balloon. The reaction mixture was stirred at room temperature for 16 h after which the catalyst was filtered off and the solvent was removed to afford the crude product. The crude product was purified by ISCO flash chromatography using 5% EtOAc in hexane to give 172 mg (85%) of the desired product. $^1$H NMR (300 MHz, CDCl$_3$) δ: 7.48 (s, 1H), 6.84 (s, 1H), 4.36 (qt, 2H), 3.79 (s, 3H), 2.4 (m, 1H), 1.79 (m, 5H), 1.39-1.31 (m, 8H).

Example 35

Preparation of Compound

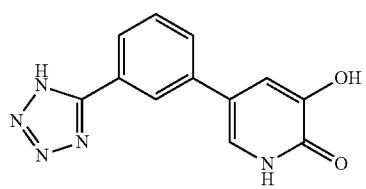 [SMILES: O=c1[nH]cc(-c2cccc(-c3nnn[nH]3)c2)cc1O]

5-[3-(1H-Tetrazol-5-yl)phenyl]-3-hydroxypyridin-2(1H)-one

To a sealed tube equipped with a small stirring bar was added 3-(5,6-dihydroxypyridin-3-yl)benzonitrile (65 mg, 0.31 mmol), DMF (2.0 ml), NaN$_3$ (80 mg, 1.2 mmol) followed by few drops of AcOH. The resulting mixture was heated to 120° C. overnight. After the completion of the reaction, the solvent was removed under vacuum. Addition of 1N HCl and stirring produced a solid which was filtered to give the pure product (13 mg, 17% yield). $^1$H NMR (300

MHz, DMSO-d$_6$) δ: 9.35 (bs, 1H), 8.18 (s, 1H), 7.97 (m, 1H), 7.77 (m, 1H), 7.63 (m, 1H), 7.36 (m, 1H), 7.21 (m, 1H).

The requisite intermediates were prepared as follows a. Preparation of Compound

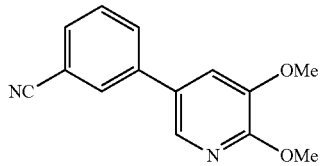 [SMILES: COc1cc(-c2cccc(C#N)c2)cnc1OC]

A mixture of 5-bromo-2,3-dimethoxypyridine (217 mg, 1.0 mmol), 3-cyanophenylboronic acid (220 mg, 1.5 mmol), Pd(PPh$_3$)$_4$ (173 mg, 0.15 mmol) and K$_2$CO$_3$ (276 mg, 2.0 mmol) in 1,4-dioxane (5.0 ml) and H$_2$O (1.5 ml) was degassed for 30 min. This mixture was heated to 100° C. and stirred for 16 h. The reaction mixture was cooled to room temperature and partitioned between NaHCO$_3$ and EtOAc (3×), and washed with NaCl (1×). The organic phase was dried over Na$_2$SO$_4$ and was concentrated. The resulting residue was purified by ISCO flash chromatography using 20% EtOAc in hexane to give 190 mg (79% yield) desired product as white solid. $^1$H NMR (300 MHz, CDCl$_3$) δ: 7.91 (d, J=2.1 Hz, 1H), 7.79-7.73 (m, 2H), 7.61-7.53 (m, 2H), 7.17 (d, J=2.1 Hz, 1H), 4.05 (s, 3H), 3.94 (s, 3H).

b. Preparation of Compound

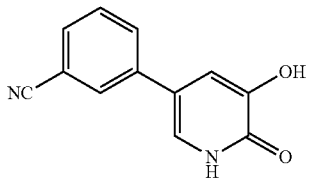 [SMILES: N#Cc1cccc(-c2c[nH]c(=O)c(O)c2)c1]

5-(m-Cyanophenyl-3-hydroxypyridin-2(1H)-one

To a solution of 2,3-dimethoxy-5(3-cyanophenyl)pyridine (40 mg, 0.167 mmol) in DCM (4.0 ml) under nitrogen, boron tribromide (0.8 ml of 1.0 M solution in CH$_2$Cl$_2$) was added. After addition was completed, the reaction mixture was stirred at room temperature overnight. The solvent was removed from the reaction mixture and the resulting solid was purified in ISCO using 10% MeOH in DCM to furnish the pure product (20 mg) yield: 53%. $^1$H NMR (300 MHz, Acetone d$_6$) δ: LC/MS: 213 (M+H).

Example 36

Preparation of Compound

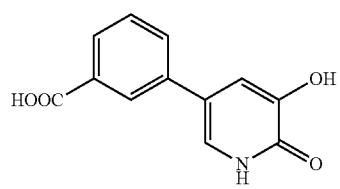 [SMILES: O=C(O)c1cccc(-c2c[nH]c(=O)c(O)c2)c1]

3-(5-Hydroxy-6-oxo-1,6-dihydropyridin-3-yl)benzoic acid

To a solution of 2,3-dimethoxy-5(3-benzoate)pyridine (110 mg, 0.4 mmol) in DCM (2.0 ml) under nitrogen, boron tribromide (1.5 ml of 1.0 M solution in CH$_2$Cl$_2$) was added. After addition was completed, the reaction mixture was stirred at room temperature overnight. The solvent was removed from the reaction mixture and the resulting solid was purified in ISCO using 10% MeOH in DCM to furnish the pure product (20 mg) yield: 53%. $^1$H NMR (300 MHz, DMSO-d$_6$) δ: 9.30 (s, 1H), 8.0 (s, 1H), 7.86-7.78 (m, 2H), 7.52 (m, 1H), 7.27 (s, 1H), 7.11 (d, 1H).

The requisite intermediate was prepared as follows.

a. Preparation of Compound

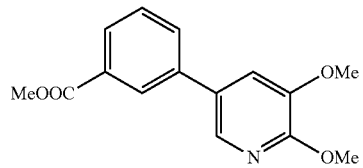

A mixture of 5-bromo-2,3-dimethoxypyridine (217 mg, 1.0 mmol), 3-carbomethoxyphenylboronic acid (270 mg, 1.5 mmol), Pd(PPh$_3$)$_4$ (138 mg, 0.12 mmol) and K$_2$CO$_3$ (276 mg, 2.0 mmol) in 1,4-dioxane (5.0 ml) and H$_2$O (1.5 ml) was degassed for 30 min. This mixture was heated to 100° C. and stirred for 16 h. The reaction mixture was cooled to room temperature and partitioned between NaHCO$_3$ and EtOAc (3×), and washed with NaCl (1×). The organic phase was dried over Na$_2$SO$_4$ and was concentrated. The resulting residue was purified by ISCO flash chromatography using 10% EtOAc in hexane to give 190 mg (79% yield) desired product. $^1$H NMR (300 MHz, CDCl$_3$) δ: 8.21 (s, 1H), 8.04-7.97 (m, 2H), 7.75 (d, J=9.0 Hz, 1H), 7.53 (d, J=7.8 Hz, 1H), 7.28 (s, 1H), 4.07 (s, 3H), 3.97 (s, 6H).

Example 37

Preparation of Compound

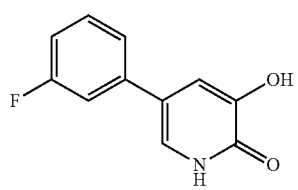 [SMILES: O=c1[nH]cc(-c2cccc(F)c2)cc1O]

5-(3-Fluorophenyl-3-hydroxypyridin-2(1H)-one

To a solution of 2,3-dimethoxy-5-(3-fluorophenyl)pyridine (40 mg, 0.17 mmol) in CH$_2$Cl$_2$ (3.0 ml) under nitrogen, was added boron tribromide (0.8 ml of a 1.0 M solution in CH$_2$Cl$_2$). After addition was completed, the reaction mixture was stirred for 16 h at room temperature. Dichloromethane was removed from the reaction mixture followed by addition of HCl (3N). The resulting solid was filtered. The solid was redissolved in CH$_2$Cl$_2$ and washed with NaHCO$_3$ and brine.

The organic phase was then dried and evaporated under reduced pressure to afford the crude product which was purified in ISCO using 5% MeOH in DCM to furnish the pure product (10 mg), yield: 28%. ¹H NMR (300 MHz, DMSO-d₆) δ: 9.29 (s, 1H), 7.43-7.34 (m, 4H), 7.15 (m, 2H), 5.78 (s, 1H).

The requisite intermediate was prepared as follows.

a. Preparation of Compound

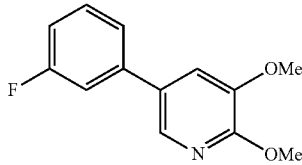 [SMILES: COc1cc(-c2cccc(F)c2)cnc1OC]

A mixture of 2,3-dimethoxypyridine (120 mg, 0.55 mmol), 3-fluorophenylboronic acid (115 mg, 0.83 mmol), Pd(PPh₃)₄ (92 mg, 0.08 mmol) and K₂CO₃ (151 mg, 1.1 mmol) in 1,4-dioxane (3.0 ml) and H₂O (1.0 ml) was degassed for 30 min. This mixture was heated to 100° C. and stirred for 16 h. The reaction mixture was cooled to room temperature and partitioned between NaHCO₃ and EtOAc (3×), and washed with NaCl (1×). The organic phase was dried over Na₂SO₄ and was concentrated. The resulting residue was purified by ISCO flash chromatography using 20% EtOAc in hexane to give 110 mg (83%) of the desired product. ¹H NMR (300 MHz, CDCl₃) δ: 7.96 (s, 1H), 7.47 (m, 1H), 7.35-7.30 (m, 1H), 7.27-7.24 (m, 2H), 7.10-7.04 (m, 1H), 4.09 (s, 3H), 3.97 (s, 3H).

Example 38

Preparation of Compound

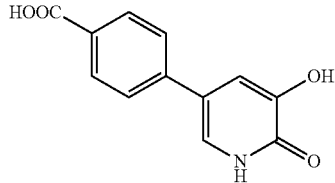 [SMILES: O=C(O)c1ccc(-c2c[nH]c(=O)c(O)c2)cc1]

4-(5-Hydroxy-6-oxo-1,6-dihydropyridin-3-yl)benzoic acid

To a solution of 2,3-dimethoxy-5(4-benzoate)pyridine (80 mg, 0.29 mmol) in DCM (3.0 ml) and toluene (3.0 ml) under nitrogen, boron tribromide (1.8 ml of 1.0 M solution in CH₂Cl₂) was added. After addition was completed, the reaction mixture was refluxed for 16 h. The solvent was removed from the reaction mixture and the resulting solid was purified in ISCO using 10% MeOH in DCM with 1% acetic acid to furnish the pure product (15 mg) yield: 21%. ¹H NMR (300 MHz, DMSO-d₆) δ: 10.65 (bs, 1H), 8.10 (s, 1H), 8.00 (m, 2H), 7.84 (s, 1H), 7.56 (d, J=7.8 Hz, 1H), 7.45 (d, J=8.1 Hz, 1H).

The requisite intermediate was prepared as follows a. Preparation of Compound

A mixture of 5-bromo-2,3-dimethoxypyridine (217 mg, 1.0 mmol), 4-carbomethoxyphenylboronic acid (270 mg, 1.5 mmol), Pd(PPh₃)₄ (138 mg, 0.12 mmol) and K₂CO₃ (276 mg, 2.0 mmol) in 1,4-dioxane (5.0 ml) and H₂O (1.5 ml) was degassed for 30 min. This mixture was heated to 100° C. and stirred for 16 h. The reaction mixture was cooled to room temperature and partitioned between NaHCO₃ and EtOAc (3×), and washed with NaCl (1×). The organic phase was dried over Na₂SO₄ and was concentrated. The resulting residue was purified by ISCO flash chromatography using 10% EtOAc in hexane to give 136 mg (50% yield) desired product. ¹H NMR (300 MHz, CDCl₃) &: 8.12 (d, 2H), 8.0 (d, 1H), 7.6 (d, 2H), 4.08 (s, 3H), 3.96 (s, 3H), 3.95 (s, 3H).

Example 39

Preparation of Compound

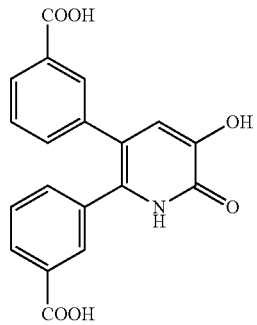 [SMILES: O=C(O)c1cccc(-c2cc(O)c(=O)[nH]c2-c2cccc(C(=O)O)c2)c1]

3,3'-(5-Hydroxy-6-oxo-1,6-dihydropyridine-2,3-diyl) dibenzoic acid

To a solution of 2,3-dimethoxy-5,6-(3-methylbenzoate) pyridine (96 mg, 0.236 mmol) in DCM (3.0 ml) and toluene (3.0 ml) under nitrogen, boron tribromide (1.5 ml of 1.0 M solution in CH₂Cl₂) was added. After addition was completed, the reaction mixture was stirred at 80° C. overnight. The solvent was removed from the reaction mixture and the resulting solid was purified in ISCO using 10% MeOH in DCM with 1% acetic acid to furnish the pure product (35 mg), yield: 42%. ¹H NMR (300 MHz, DMSO-d₆) δ: 7.83

(m, 1H), 7.73 (m, 2H), 7.59 (m, 1H), 7.4-7.24 (m, 4H), 6.87 (s, 1H).

The requisite intermediate was prepared as follows.

a. Preparation of Compound

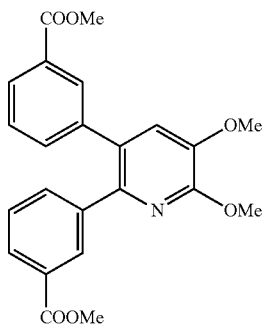 [SMILES: COC(=O)c1cccc(-c2cc(OC)c(OC)nc2-c2cccc(C(=O)OC)c2)c1]

A mixture of 5,6-dibromo-2,3-dimethoxypyridine (296 mg, 1.0 mmol), 3-carbomethoxyphenylboronic acid (270 mg, 1.5 mmol), Pd(PPh$_3$)$_4$ (173 mg, 0.15 mmol) and K$_2$CO$_3$ (276 mg, 2.0 mmol) in 1,4-dioxane (3.0 ml) and H$_2$O (1.0 ml) was degassed for 30 min. This mixture was heated to 100° C. and stirred for 16 h. The reaction mixture was cooled to room temperature and partitioned between NaHCO$_3$ and EtOAc (3×), and washed with NaCl (1×). The organic phase was dried over Na$_2$SO$_4$ and was concentrated. The resulting residue was purified by ISCO flash chromatography using 20% EtOAc in hexane to give 106 mg (26%) of the desired product. $^1$H NMR (300 MHz, CDCl$_3$) δ: 8.13 (s, 1H), 7.99 (s, 1H), 7.94 (d, J=7.2 Hz, 1H), 7.88 (d, J=7.8 Hz, 1H), 7.41 (d, J=7.2 Hz, 1H), 7.31-7.20 (m, 3H), 7.10 (s, 1H), 4.13 (s, 3H), 3.96 (s, 3H), 3.91 (s, 3H), 3.86 (s, 3H).

Example 40

Preparation of Compound

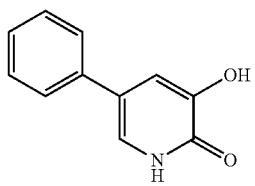 [SMILES: O=c1[nH]cc(-c2ccccc2)cc1O]

5-Phenyl-3-hydroxypyridin-2(1H)-one

To a solution of 2,3-dimethoxy-5-phenylpyridine (100 mg, 0.465 mmol) in CH$_2$Cl$_2$ (3.0 ml) under nitrogen, boron tribromide was added (1.0 ml of 1.0 M solution in CH$_2$Cl$_2$). After addition was completed, the reaction mixture was stirred for 16 h at room temperature. Dichloromethane was removed and the reaction mixture was diluted with ethyl acetate. The solution was washed with NaHCO$_3$ and brine. The organic phase was then dried and evaporated under reduced pressure to afford the crude product which was purified in ISCO using 10% MeOH in DCM to furnish the pure product (21 mg) as white solid, yield: 24%. mp 175-177° C.; $^1$H NMR (300 MHz, DMSO-d$_6$) δ: 9.33 (bs, 1H), 7.62-7.38 (m, 5H), 7.30 (s, 1H), 7.20 (s, 1H). $^{13}$C NMR (75 MHz, DMSO d$_6$) δ: 172.5, 158.3, 147.9, 137.3, 129.6, 126.0, 121.9, 115.6, 107.7. HRMS Calcd for C$_1$H$_9$NO$_2$ (M+H)$^+$ 188.0706. Found 188.0708.

The requisite intermediate was prepared as follows a. Preparation of Compound

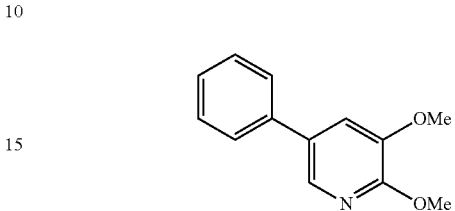

A mixture of 5-bromo-2,3-dimethoxypyridine (100 mg, 0.46 mmol), phenylboronic acid (84 mg, 0.69 mmol), Pd(PPh$_3$)$_4$ (58 mg, 0.05 mmol) and K$_2$CO$_3$ (125 mg, 0.92 mmol) in 1,4-dioxane (3.0 ml) and H$_2$O (1.0 ml) was degassed for 30 min. This mixture was heated to 100° C. and stirred for 16 h. The reaction mixture was cooled to room temperature and partitioned between NaHCO$_3$ and EtOAc (3×), and washed with NaCl (1×). The organic phase was dried over Na$_2$SO$_4$ and was concentrated. The resulting residue was purified by ISCO flash chromatography using DCM to give 100 mg (99.9%) desired product. $^1$H NMR (300 MHz, CDCl$_3$) δ: 7.97 (s, 1H), 7.53-7.36 (m, 5H), 7.24 (s, 1H), 4.06 (s, 3H), 3.92 (s, 3H). $^{13}$C NMR (75 MHz, CDCl$_3$) δ: 176.1, 153.8, 144.0, 138.0, 134.9, 130.8, 129.6, 128.9, 127.4, 126.8, 116.4, 56.2, 54.2.

Example 41

Preparation of Compound

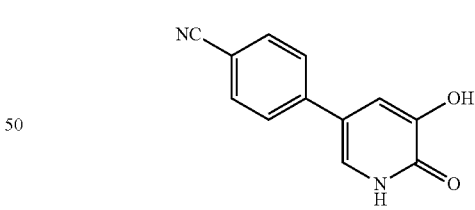

5-(4-Cyanophenyl-3-hydroxypyridin-2(1H)-one

To a solution of 2,3-dimethoxy-5(4-cyanophenyl)pyridine (100 mg, 0.417 mmol) in toluene (3.0 ml) under nitrogen, boron tribromide (1.2 ml of 1.0 M solution in CH$_2$Cl$_2$) was added. After addition was completed, the reaction mixture was heated to 100° C. in a sealed tube for 2 h and then at room temperature overnight. The solvent was removed from the reaction mixture and the resulting solid was purified in ISCO using 10% MeOH in DCM to furnish the pure product (86 mg) yield: 60%. $^1$H NMR (300 MHz, Acetone d$_6$) δ:

7.67 (s, 4H), 7.36 (s, 1H), 7.10 (s, 1H). HRMS Calcd for C$_{12}$H$_8$N$_2$O$_2$ (M+H)$^+$ 212.0580. Found 212.0578.

The requisite intermediate was prepared as follows a. Preparation of Compound 5

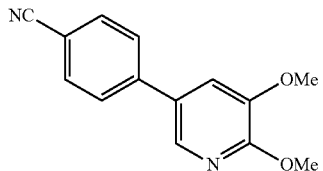 [SMILES: COc1cc(-c2ccc(C#N)cc2)cnc1OC]

A mixture of 5-bromo-2,3-dimethoxypyridine (570 mg, 2.63 mmol), 4-cyanophenylboronic acid (578 mg, 3.94 mmol), Pd(PPh$_3$)$_4$ (311 mg, 0.27 mmol) and K$_2$CO$_3$ (717 mg, 5.2 mmol) in 1,4-dioxane (6.0 ml) and H$_2$O (1.5 ml) was degassed for 30 min. This mixture was heated to 100° C. and stirred for 16 h. The reaction mixture was cooled to room temperature and partitioned between NaHCO$_3$ and EtOAc (3×), and washed with NaCl (1×). The organic phase was dried over Na$_2$SO$_4$ and was concentrated. The resulting residue was purified by ISCO flash chromatography using 20% EtOAc in hexane to give 495 mg (78% yield) desired product. $^1$H NMR (300 MHz, CDCl$_3$) δ: 7.74 (s, 1H), 7.51 (d, J=8.4 Hz, 2H), 7.41 (d, J=8.4 Hz, 2H), 7.0 (s, 1H), 3.84 (s, 3H), 3.73 (s, 3H). $^{13}$C NMR (75 MHz, CDCl$_3$) δ: 176.2, 154.7, 144.3, 142.6, 135.4, 132.7, 128.7, 127.3, 118.8, 115.7, 110.9, 55.8, 54.0.

Example 42

Preparation of Compound

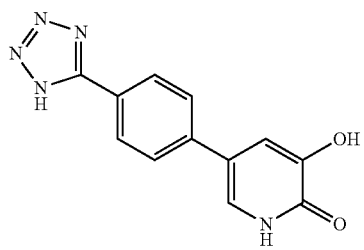 [SMILES: O=c1[nH]cc(-c2ccc(-c3nnn[nH]3)cc2)cc1O]

5-[4-(1H-Tetrazol-5-yl)phenyl]-3-hydroxypyridin-2(1H)-one

To a sealed tube equipped with a small stirring bar was added 4-(5,6-dihydroxypyridin-3-yl)benzonitrile (86 mg, 0.40 mmol), DMF (3.0 ml), NaN$_3$ (104 mg, 1.6 mmol) followed by AcOH (1.0 ml). The resulting mixture was heated to 120° C. overnight. After the completion of the reaction, the solvent was removed under vacuum. Addition of 1N HCl and stirring produced a solid which was filtered to give the pure product (35 mg, 34% yield). $^1$H NMR (300 MHz, DMSO-d$_6$) δ: 7.96 (m, 3H), 7.53 (d, J=9.0 Hz, 2H), 7.22 (s, 1H), 7.16 (s, 1H). HRMS Calcd for C$_{12}$H$_9$N$_5$O$_2$ (M+H)$^+$ 256.0929. Found 256.0827.

Example 43

Preparation of Compound

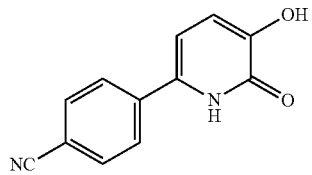 [SMILES: N#Cc1ccc(-c2ccc(O)c(=O)[nH]2)cc1]

6-(4-Cyanophenyl-3-hydroxypyridin-2(1H)-one

To a solution of 2-ethoxy-3-methoxy-6-(4-cyanophenyl)pyridine (150 mg, 0.59 mmol) in CH$_2$Cl$_2$ (5.0 ml) under nitrogen, was added boron tribromide (2.0 ml, 1.0 M solution in CH$_2$Cl$_2$). After addition was completed, the reaction mixture was stirred for 16 h at room temperature. Dichloromethane was removed from the reaction mixture followed by addition of HCl (3N). The resulting solid was filtered. The solid was redissolved in CH$_2$Cl$_2$ and washed with NaHCO$_3$ and brine. The organic phase was then dried and evaporated under reduced pressure to afford the crude product which was purified in ISCO using 10% MeOH in DCM to furnish the pure product (90 mg) as tan solid, yield: 72%. mp 161-163° C.; $^1$H NMR (300 MHz, DMSO-d$_6$) δ: 7.88 (s, 4H), 6.85 (d, J=7.5 Hz, 1H), 6.68 (d, J=7.5 Hz, 1H). $^{13}$C NMR (75 MHz, DMSO-d$_6$) δ: 172.5, 159.1, 148.0, 138.8, 134.6, 133.3, 127.3, 119.4, 116.9, 111.1, 107.6. HRMS Calcd for C$_{12}$H$_9$N$_2$O$_2$ (M+H)$^+$ 213.0659. Found 213.0651.

The requisite intermediate was prepared as follows.

a. Preparation of Compound

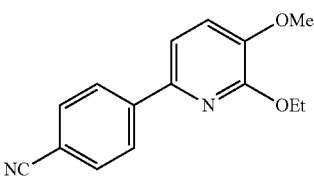

A mixture of 6-iodo-2-ethoxy-3-methoxypyridine (150 mg, 0.894 mmol), 4-cyanophenylboronic acid (197 mg, 1.34 mmol), Pd(PPh$_3$)$_4$ (155 mg, 0.136 mmol) and K$_2$CO$_3$ (276 mg, 2.0 mmol) in 1,4-dioxane (3.0 ml) and H$_2$O (1.0 ml) was degassed for 30 min. This mixture was heated to 100° C. and stirred for 16 h. The reaction mixture was cooled to room temperature and partitioned between NaHCO$_3$ and EtOAc (3×), and washed with NaCl (1×). The organic phase was dried over Na$_2$SO$_4$ and was concentrated. The resulting residue was purified by ISCO flash chromatography using 20% EtOAc in hexane to give 185 mg (82% yield) desired product. $^1$H NMR (300 MHz, CDCl$_3$) δ: 8.07 (d, J=8.4 Hz, 2H), 7.70 (d, J=8.1 Hz, 2H), 7.37 (d, J=8.4 Hz, 1H), 7.12 (d, J=8.1 Hz, 1H), 4.59 (qt, 2H), 3.93 (s, 3H), 1.51 (t, 3H). $^{13}$C NMR (75 MHz, CDCl$_3$) δ: 172.2, 153.5, 144.5, 143.0, 142.5, 132.4, 126.3, 119.1, 117.5, 113.7, 110.9, 62.1, 55.9, 14.6.

Example 44

Preparation of Compound

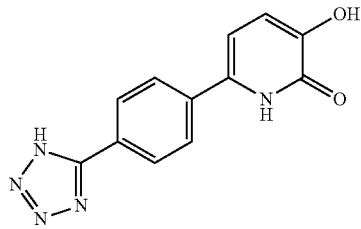 [SMILES: O=c1[nH]c(-c2ccc(-c3nnn[nH]3)cc2)ccc1O]

6-[4-(1H-tetrazol-5-yl)phenyl]-3-hydroxypyridin-2(1H)-one

To a sealed tube equipped with a small stirring bar was added 6-(4-cyanophenyl-3-hydroxypyridin-2(1H)-one (50 mg, 0.235 mmol), DMF (2.0 ml), NaN$_3$ (61 mg, 0.94 mmol) followed by AcOH (1.0 ml). The resulting mixture was heated to 120° C. overnight. After the completion of the reaction, the solvent was removed under vacuum. Addition of 1N HCl and stirring produced a solid which was filtered to give the pure product (51 mg, 85% yield). $^1$H NMR (300 MHz, DMSO-d$_6$) δ: 8.07 (d, 2H), 7.83 (d, J=8.1 Hz, 2H), 7.76 (d, J=8.4 Hz, 1H), 6.84 (d, J=7.5 Hz, 1H), 6.59 (d, J=7.5 Hz, 1H). $^{13}$C NMR (75 MHz, DMSO-d$_6$) δ: 172.5, 159.4, 135.5, 127.6, 127.2, 114.3, 107.6. HRMS Calcd for C$_{12}$H$_9$N$_5$O$_2$ (M+H)$^+$ 256.0829. Found 256.0820.

Example 45

Preparation of Compound

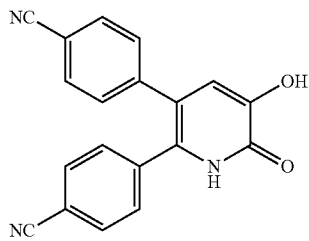 [SMILES: N#Cc1ccc(-c2cc(O)c(=O)[nH]c2-c2ccc(C#N)cc2)cc1]

5,6-bis(4-Cyanophenyl)-3-hydroxypyridin-2(1H)-one

To a solution of 2,3-dimethoxy-5,6-bis(4-cyanophenyl)pyridine (50 mg, 0.146 mmol) in CH$_2$Cl$_2$ (3.0 ml) under nitrogen, was added boron tribromide (1.0 M solution in CH$_2$Cl$_2$) (1.5 ml). After addition was completed, the reaction mixture was stirred for 16 h at room temperature. Dichloromethane was removed from the reaction mixture followed by addition of HCl (3N). The resulting solid was filtered, which was redissolved in CH$_2$Cl$_2$ and washed with NaHCO$_3$ and brine, dried using anhydrous sodium sulfate and evaporated under reduced pressure to afford a solid (15 mg), yield: 33%. mp 159-162° C.; 1H NMR (300 MHz, MeOD-d$_4$) δ: 7.62 (m 4H), 7.3 (m, 4H), 7.03 (s, 1H). HRMS Calcd for C$_{19}$H$_{11}$N$_3$O$_2$ (M+H)$^+$ 314.0924. Found 314.0920. The requisite intermediate was prepared as follows.

a. Preparation of Compound

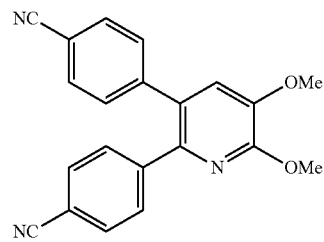 [SMILES: COc1cc(-c2ccc(C#N)cc2)c(-c2ccc(C#N)cc2)nc1OC]

The mixture of 5,6-dibromo-2,3-dimethoxypyridine (100 mg, 0.338 mmol), 4-cyanophenylboronic acid (102 mg, 0.7 mmol), Pd(PPh$_3$)$_4$ (58 mg, 0.05 mmol) and K$_2$CO$_3$ (136 mg, 1.0 mmol) in 1,4-dioxane (3.0 ml) and H$_2$O (1.0 ml) was degassed for 30 min. This mixture was heated to 100° C. and stirred for 16 h. The reaction mixture was cooled to room temperature and partitioned between NaHCO$_3$ and EtOAc (3×), and washed with NaCl (1×). The organic phase was dried over Na$_2$SO$_4$ and was concentrated. The resulting residue was purified by ISCO flash chromatography using 30% EtOAc in hexane to give 56 mg of the desired product, yield: 49%. $^1$H NMR (300 MHz, CDCl$_3$) δ: 7.56 (d, J=8.1 Hz, 2H), 7.47 (d, J=9.0 Hz, 2H), 7.36 (d, J=8.4 Hz, 2H), 7.25 (d, J=8.1 Hz, 2H), 7.0 (s, 1H), 4.05 (s, 3H), 3.91 (s, 3H). $^{13}$C NMR (75 MHz, CDCl$_3$) δ: 172.3, 153.7, 144.3, 144.0, 143.6, 142.0, 132.4, 131.7, 130.5, 130.4, 128.1, 119.6, 118.7, 118.5, 111.2, 111.1, 58.2, 56.2.

Example 46

Preparation of Compound

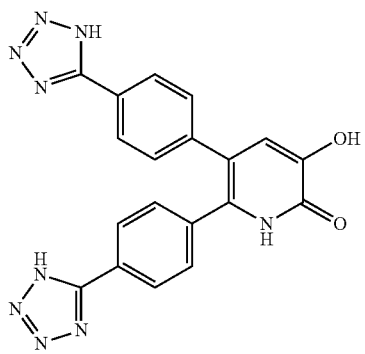 [SMILES: O=c1[nH]c(-c2ccc(-c3nnn[nH]3)cc2)c(-c2ccc(-c3nnn[nH]3)cc2)cc1O]

5,6-bis[4-(1H-Tetrazol-5-yl)phenyl]-3-hydroxypyridin-2(1H)-one

To a sealed tube equipped with a small stirring bar was added 5,6-bis(4-cyanophenyl)-3-hydroxypyridin-2(1H)-one (100 mg, 0.319 mmol), DMF (2.0 ml), NaN$_3$ (61 mg, 0.94 mmol) followed by AcOH (1.0 ml). The resulting mixture was heated to 120° C. overnight. After completion of the reaction, the solvent was removed under vacuum. Addition of 1N HCl and stirring produced a solid which was filtered to give the pure product (45 mg, 35% yield). mp 180-182° C.; ¹H NMR (300 MHz, DMSO-d₆) δ: 7.96 (bs, 2H), 7.85-7.77 (m, 4H), 7.18 (d, J=8.4 Hz, 2H), 7.07 (d, J=8.4 Hz, 2H), 6.84 (s, 1H). HRMS Calcd for $C_{19}H_{13}N_9O_2$ (M+H)⁺ 400.1265. Found 400.1262.

Example 47

Preparation of Compound

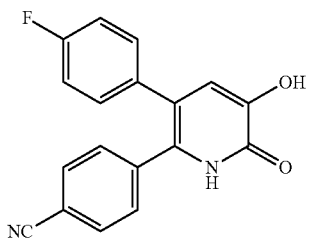 [SMILES: N#Cc1ccc(-c2[nH]c(=O)c(O)cc2-c2ccc(F)cc2)cc1]

5-(4-Fluorophenyl)-6-(4-cyanophenyl)-3-hydroxy-pyridin-2(1H)-one

To a solution of 5-(4-fluorophenyl)-6-(4-cyanophenyl)-2,3-dimethoxypyridine (240 mg, 0.72 mmol) in CH₂Cl₂ (3.0 ml) under nitrogen, was added boron tribromide (2.0 ml of a 1.0 M solution in CH₂Cl₂). After addition was completed, the reaction mixture was stirred for 16 h at room temperature. Dichloromethane was removed from the reaction mixture followed by addition of HCl (3N). The resulting solid was filtered. The solid was redissolved in CH₂Cl₂ and washed with NaHCO₃ and brine. The organic phase was then dried and evaporated under reduced pressure to afford the crude product which was purified in ISCO using 5% MeOH in DCM to furnish the pure product (183 mg) as off-white solid, yield: 83%. mp 255-258° C.; ¹H NMR (300 MHz, DMSO-d₆) δ: ¹H NMR (300 MHz, DMSO-d₆) δ: 7.75 (d, J=8.1 Hz, 2H), 7.33 (d, J=8.4 Hz, 2H), 7.07 (d, J=7.2 Hz, 4H), 6.82 (s, 1H). ¹³C NMR (75 MHz, DMSO-d₆) δ: 172.5, 147.0, 132.7, 132.5, 132.2, 132.1, 131.6, 119.2, 116.1, 115.7, 107.6. HRMS Calcd for $C_{18}H_{11}FN_2O_2$ (M+H)⁺ 307.0877. Found 307.0844.

The requisite intermediates were prepared as follows.

a. Preparation of Compound

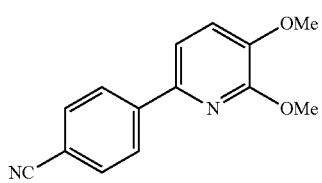 [SMILES: COc1ccc(-c2ccc(C#N)cc2)nc1OC]

A mixture of 6-bromo-2,3-dimethoxypyridine (434 mg, 2.0 mmol), 4-cyanophenylboronic acid (440 mg, 3.0 mmol), Pd(PPh₃)₄ (346 mg, 0.3 mmol) and K₂CO₃ (552 mg, 4.0 mmol) in 1,4-dioxane (3 ml) and H₂O (1.0 ml) was degassed for 30 min. This mixture was heated to 100° C. and stirred for 16 h. The reaction mixture was cooled to room temperature and partitioned between NaHCO₃ and EtOAc (3×), and washed with NaCl (1×). The organic phase was dried over Na₂SO₄ and was concentrated. The resulting residue was purified by ISCO flash chromatography using 25% EtOAc in hexane to give 200 mg desired product. ¹H NMR (300 MHz, CDCl₃) δ: 8.04 (d, J=8.7 Hz, 2H), 7.6 (d, J=8.4 Hz, 2H), 7.36 (d, J=8.1 Hz, 1H), 7.09 (d, J=8.1 Hz, 1H), 4.09 (s, 3H), 3.90 (s, 3H).

b. Preparation of Compound

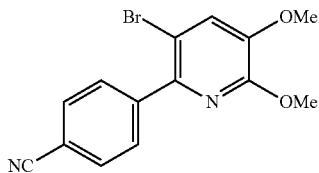 [SMILES: COc1cc(Br)c(-c2ccc(C#N)cc2)nc1OC]

To a mixture of 2,3-dimethoxy-6-(4-cyanophenyl)pyridine (210 mg, 0.875 mmol) in acetic acid (3.0 ml) was added sodium acetate (217 mg, 1.6 mmol). The reaction mixture was cooled to 0° C. and Br₂ (0.045 ml) in acetic acid (1.0 ml) was added dropwise. The reaction mixture was stirred at room temperature for 12 h. To this mixture 25% NaOH was added at 0° C. until pH 6 and then extracted with DCM three times. Organic layer wad dried, concentrated under reduced pressure and purified by ISCO using 20% EtOAC in hexane to afford pure product 360 mg (91% yield). ¹H NMR (300 MHz, CDCl₃) δ: 7.51 (d, J=8.7 Hz, 2H), 7.55 (d, J=8.4 Hz, 2H), 6.97 (s, 1H), 4.07 (s, 3H), 3.89 (s, 3H).

c. Preparation of Compound

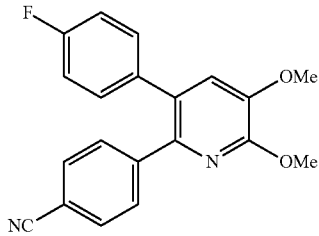 [SMILES: COc1cc(-c2ccc(F)cc2)c(-c2ccc(C#N)cc2)nc1OC]

A mixture of 5-bromo-6-(4-cyanophenyl)-2,3-dimethoxypyridine (360 mg, 1.13 mmol), 4-fluorophenylboronic acid (237 mg, 1.69 mmol), Pd(PPh₃)₄ (173 mg, 0.15 mmol) and K₂CO₃ (307 mg, 2.26 mmol) in 1,4-dioxane (3 ml) and H₂O (1.5 ml) was degassed for 30 min. This mixture was heated to 100° C. and stirred for 16 h. The reaction mixture was cooled to room temperature and partitioned between NaHCO₃ and EtOAc (3×), and washed with NaCl (1×). The organic phase was dried over Na₂SO₄ and was concentrated. The resulting residue was purified by ISCO flash chromatography using 25% EtOAc in hexane to give 340 mg (90% yield) of the desired product. ¹H NMR (300 MHz, CDCl₃) δ: 7.49-7.40 (m, 4H), 7.13-7.09 (m, 2H), 7.02-6.95 (m, 3H), 4.07 (s, 3H), 3.92 (s, 3H). ¹³C NMR (75 MHz, CDCl₃) δ: 163.8, 160.5, 153.1, 144.17, 143.76, 141.56, 135.47, 135.42, 132.86, 131.54, 131.31, 131.20, 130.50, 129.05, 127.94, 120.16, 118.96, 115.96, 115.57, 110.58, 56.01, 53.88.

Example 48

Preparation of Compound

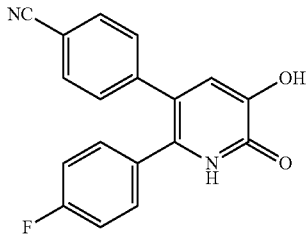

5-(4-Cyanophenyl)-6-(4-fluorophenyl)-3-hydroxy-pyridin-2(1H)-one

To a solution of 5-(4-cyanophenyl)-6-(4-fluorophenyl)-2,3-dimethoxypyridine (150 mg, 0.45 mmol) in $CH_2Cl_2$ (4.0 ml) under nitrogen, was added boron tribromide (2.0 ml of a 1.0 M solution in $CH_2Cl_2$). After addition was completed, the reaction mixture was stirred for 20 h at room temperature. Dichloromethane was removed from the reaction mixture followed by addition of HCl (3N). The resulting solid was filtered. The solid was redissolved in $CH_2Cl_2$ and washed with $NaHCO_3$ and brine. The organic phase was then dried and evaporated under reduced pressure to afford the crude product which was purified in ISCO using 5% MeOH in DCM to furnish the pure product (85 mg) as white solid, yield: 62%. mp 255-257° C.; $^1$H NMR (300 MHz, DMSO-$d_6$) δ: 9.39 (bs, 1H), 7.60 (d, J=8.1 Hz, 2H), 7.14-7.03 (m, 6H), 6.77 (s, 1H). HRMS Calcd for $C_{18}H_{11}FN_2O_2$ (M+H)$^+$ 307.0877. Found 307.0870.

The requisite intermediates were prepared as follows.

a. Preparation of Compound

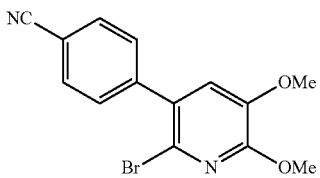 [SMILES: COc1cc(-c2ccc(C#N)cc2)c(Br)nc1OC]

To a solution of 2,3-dimethoxy-5-(4-cyanophenyl)pyridine (350 mg, 1.46 mmol) in acetic acid (8.0 ml) was added sodium acetate (402 mg, 2.9 mmol). The reaction mixture was cooled to 0° C. and $Br_2$ (238 mg) in acetic acid (1.0 ml) was added dropwise. The reaction mixture was stirred at room temperature for 16 h. To this mixture 25% NaOH was added at 0° C. until pH 6 and then extracted with dichloromethane three times. Organic layer wad dried, concentrated under reduced pressure and purified by ISCO using 100% DCM to afford pure product 310 mg (66% yield) as an oil. $^1$H NMR (300 MHz, CDCl$_3$) δ: 7.70 (d, J=8.1 Hz, 2H), 7.54 (d, J=8.1 Hz, 2H), 6.99 (s, 1H). $^{13}$C NMR (75 MHz, CDCl$_3$) δ: 172.5, 153.4, 143.9, 132.3, 130.7, 120.7, 118.8, 111.9, 56.5, 54.4.

b. Preparation of Compound

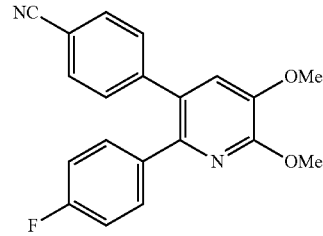 [SMILES: COc1cc(-c2ccc(C#N)cc2)c(-c2ccc(F)cc2)nc1OC]

A mixture of 6-bromo-5-(4-cyanophenyl)-2,3-dimethoxypyridine (150 mg, 0.47 mmol), 4-fluorophenylboronic acid (99 mg, 0.70 mmol), Pd(PPh$_3$)$_4$ (70 mg, 0.06 mmol) and K$_2$CO$_3$ (129 mg, 0.94 mmol) in 1,4-dioxane (3.0 ml) and H$_2$O (1.0 ml) was degassed for 30 min. This mixture was heated to 100° C. and stirred for 16 h. The reaction mixture was cooled to room temperature and partitioned between NaHCO$_3$ and EtOAc (3×), and washed with NaCl (1×). The organic phase was dried over Na$_2$SO$_4$ and was concentrated. The resulting residue was purified by ISCO flash chromatography using 25% EtOAc in hexane to give 150 mg (95% yield) desired product. $^1$H NMR (300 MHz, CDCl$_3$) δ: 7.51 (m, 2H), 7.35-7.33 (m, 2H), 7.27-7.22 (m, 2H), 6.99 (s, 1H), 6.89 (t, J=8.7 Hz, 2H), 4.08 (s, 3H), 3.92 (s, 3H).

Example 49

Preparation of Compound

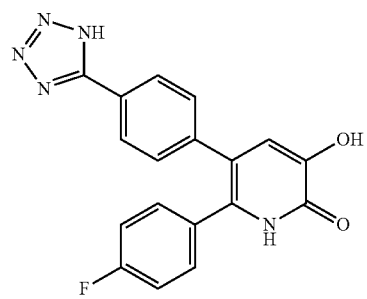 [SMILES: O=c1[nH]c(-c2ccc(F)cc2)c(-c2ccc(-c3nnn[nH]3)cc2)cc1O]

5-[4-(1H-Tetrazol-5-yl)phenyl]-6-(4-fluorophenyl)-3-hydroxypyridin-2(1H)-one

To a sealed tube equipped with a small stirring bar was added 5-(4-cyanophenyl)-6-(4-fluorophenyl)-3-hydroxy-pyridin-2(1H)-one (45 mg, 0.141 mmol), DMF (2.0 ml), NaN$_3$ (38 mg, 0.56 mmol) followed by AcOH (0.1 ml). The resulting mixture was heated to 120° C. for 4 h. After the completion of the reaction, the solvent was removed under reduced pressure. Addition of 3N HCl and stirring produced a solid which was filtered to give the pure product (15 mg, 31% yield). mp 185-188° C.; $^1$H NMR (300 MHz, DMSO-$d_6$) δ: 9.4 (bs, 1H), 7.83 (d, J=8.1 Hz, 2H), 7.20 (d, J=7.8 Hz, 4H), 7.10 (m, 2H), 6.86 (s, 1H). HRMS Calcd for $C_{18}H_{12}FN_5O_2$ (M+H)$^+$ 350.1048. Found 350.1057.

Example 50

Preparation of Compound

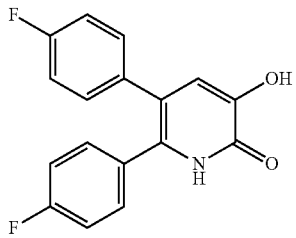 [SMILES: O=c1[nH]c(-c2ccc(F)cc2)c(-c2ccc(F)cc2)cc1O]

5,6-bis(4-Fluorophenyl)-3-hydroxypyridin-2(1H)-one

To a solution of 2,3-dimethoxy-5,6-bis(4-fluorophenyl)pyridine (100 mg, 0.3 mmol) in $CH_2Cl_2$ (3.0 ml) under nitrogen, was added boron tribromide (1.0 M solution in $CH_2Cl_2$) (1.5 ml). After addition was completed, the reaction mixture was stirred for 16 h at room temperature. Dichloromethane was removed from the reaction mixture followed by addition of HCl (3N). The resulting solid was filtered, which was redissolved in $CH_2Cl_2$ and washed with $NaHCO_3$ and brine, dried using anhydrous sodium sulfate and evaporated under reduced pressure to afford a solid (80 mg), yield: 87%. mp 152-157° C.; $^1H$ NMR (300 MHz, DMSO-$d_6$) δ: 7.66 (m, 2H), 7.6 (m, 2H), 7.46 (m, 2H), 7.20 (d, J=6.0 Hz, 2H), 7.08 (m, 1H), 6.7 (d, 1H), 6.28 (d, 1H). HRMS Calcd for $C_{17}H_{11}F_2NO_2$ $(M+H)^+$ 300.0831. Found 300.0830.

The requisite intermediate was prepared as follows a. Preparation of Compound

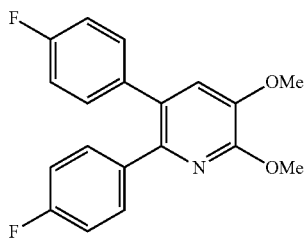 [SMILES: COc1cc(-c2ccc(F)cc2)c(-c2ccc(F)cc2)nc1OC]

The mixture of 5,6-dibromo-2,3-dimethoxypyridine (260 mg, 0.87 mmol), 4-fluorophenylboronic acid (367 mg, 3.0 mmol), $Pd(PPh_3)_4$ (303 mg, 0.26 mmol) and $K_2CO_3$ (414 mg, 3.0 mmol) in 1,4-dioxane (4.0 ml) and $H_2O$ (1.0 ml) was degassed for 30 min. This mixture was heated to 100° C. and stirred for 16 h. The reaction mixture was cooled to room temperature and partitioned between $NaHCO_3$ and EtOAc (3×), and washed with NaCl (1×). The organic phase was dried over $Na_2SO_4$ and was concentrated. The resulting residue was purified by ISCO flash chromatography using 10% EtOAc in hexane to give 210 mg of the desired product, yield: 73%. $^1H$ NMR (300 MHz, $CDCl_3$) δ: 7.35 (m, 2H), 7.20 (m, 2H), 7.20 (m, 2H), 7.17 (m, 2H), 7.04-6.98 (m, 4H), 4.18 (s, 3H), 3.01 (s, 3H). LC/MS: 328.205 (M+H).

Example 51

Preparation of Compound

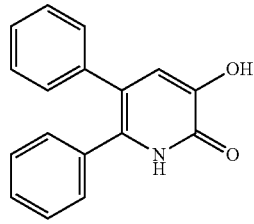 [SMILES: O=c1[nH]c(-c2ccccc2)c(-c2ccccc2)cc1O]

5,6-Diphenyl-3-hydroxypyridin-2(1H)-one

To a solution of 2,3-dimethoxy-5,6-diphenylpyridine (130 mg, 0.45 mmol) in $CH_2Cl_2$ (6.0 ml) under nitrogen, was added boron tribromide (2.0 ml of a 1.0 M solution in $CH_2Cl_2$). After addition was completed, the reaction mixture was stirred for 16 h at room temperature. Dichloromethane was removed from the reaction mixture followed by addition of HCl (3N). The resulting solid was filtered. The solid was redissolved in $CH_2Cl_2$ and washed with $NaHCO_3$ and brine. The organic phase was then dried and evaporated under reduced pressure to afford a solid (60 mg), yield: 55%. $^1H$ NMR (300 MHz, DMSO-$d_6$) δ: 11.89, 9.31, 7.58 (m, 6H), 7.23 (t, 1H), 7.15 (m, 1H), 7.07 (t, 1H), 6.7 (d, J=7.2 Hz, 1H). $^{13}C$ NMR (75 MHz, DMSO-$d_6$) δ: 172.5, 158.7, 146.9, 139.2, 134.7, 130.6, 130.1, 128.8, 128.7, 127.1, 119.3, 107.7. HRMS Calcd for $C_{17}H_{13}NO_2$ $(M+H)^+$ 264.1019. Found 264.1020. mp 249-255° C.

The requisite intermediate was prepared as follows a. Preparation of Compound

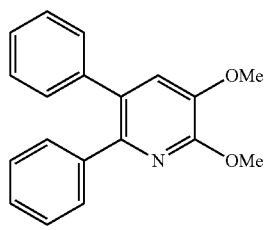 [SMILES: COc1cc(-c2ccccc2)c(-c2ccccc2)nc1OC]

A mixture of 5,6-dibromo-2,3-dimethoxypyridine (150 mg, 0.5 mmol, phenylboronic acid (242 mg, 2.0 mmol), $Pd(PPh_3)_4$ (231 mg, 0.2 mmol) and $K_2CO_3$ (276 mg, 2.0 mmol) in 1,4-dioxane (5.0 ml) and $H_2O$ (1.5 ml) was degassed for 30 min. This mixture was heated to 100° C. and stirred for 16 h. The reaction mixture was cooled to room temperature and partitioned between $NaHCO_3$ and EtOAc (3×), and washed with NaCl (1×). The organic phase was dried over $Na_2SO_4$ and was concentrated. The resulting residue was purified by ISCO flash chromatography using 10% EtOAc in hexane to give 130 mg of the desired product, yield: 89%. $^1H$ NMR (300 MHz, $CDCl_3$) δ: 7.4 (m, 2H), 7.29 (m, 3H), 7.24-7.21 (m, 5H), 7.12 (s, 1H), 4.15 (s, 3H), 3.96 (s, 3H). LC/MS: 292.23 (M+H).

Example 52

Preparation of Compound

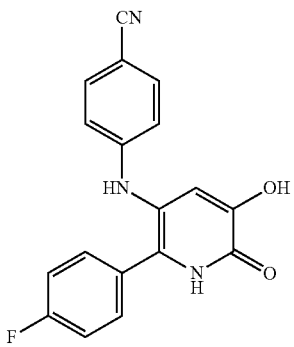 [SMILES: N#Cc1ccc(Nc2cc(O)c(=O)[nH]c2-c2ccc(F)cc2)cc1]

4-((2-(4-Fluorophenyl)-5-hydroxy-6-oxo-1,6-dihydropyridin-3-yl)amino)benzonitrile To a solution of 4-((2-(4-flurophenyl)-5,6-dimethoxypyridin-3-yl)amino)benzonitrile (35 mg, 0.1 mmol) in $CH_2Cl_2$ (3.0 ml) under nitrogen, was added boron tribromide (0.5 ml of a 1.0 M solution in $CH_2Cl_2$). After addition was completed, the reaction mixture was stirred for 16 h at room temperature. Dichloromethane was removed from the reaction mixture followed by addition of HCl (3N). The resulting solid was filtered. The solid was redissolved in $CH_2Cl_2$ and washed with $NaHCO_3$ and brine. The organic phase was then dried and evaporated under reduced pressure to afford a solid in 55% yield. $^1H$ NMR (300 MHz, $CDCl_3$) δ: 7.47 (d, J=8.1 Hz, 1H), 7.38 (m, 2H), 7.05 (m, 2H), 6.88 (m, 2H), 6.67 (d, J=8.4 Hz, 1H), 6.30 (d, J=7.2 Hz, 1H), 5.44 (bs, 1H).

The requisite intermediate was prepared as follows a. Preparation of Compound

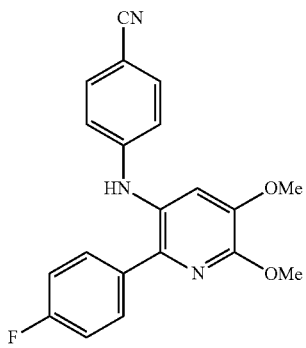 [SMILES: COc1cc(Nc2ccc(C#N)cc2)c(-c2ccc(F)cc2)nc1OC]

A mixture of 5-bromo-6-(4-fluorophenyl)-2,3-dimethoxypyridine (185 mg, 0.59 mmol, 4-cyanoaniline (104 mg, 0.88 mmol), $Pd_2(dba)_3$ (46 mg, 0.05 mmol), 1,3-bis(2,6-diisopropylphenyl)imidazolium chloride (21 mg, 0.05 mmol) and KO$^t$Bu (98 mg, 0.88 mmol) in 1,4-dioxane (4.0 ml) was degassed for 30 min. This mixture was heated to 105° C. and stirred for 16 h. The reaction mixture was cooled to room temperature and partitioned between $NaHCO_3$ and EtOAc (3×), and washed with NaCl (1×). The organic phase was dried over $Na_2SO_4$ and was concentrated. The resulting residue was purified by ISCO flash chromatography using 25% EtOAc in hexane to give 35 mg of the desired product, yield: 17%. $^1H$ NMR (300 MHz, $CDCl_3$) δ: 7.58-7.52 (m, 2H), 7.29-7.11 (m, 6H), 6.8-6.77 (m, 1H), 4.16 (s, 3H), 3.95 (s, 3H).

Example 53

Preparation of Compound

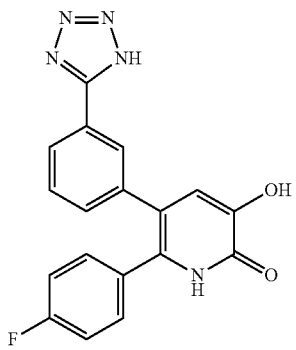 [SMILES: O=c1[nH]c(-c2ccc(F)cc2)c(-c2cccc(-c3nnn[nH]3)c2)cc1O]

5-(3-(1H-Tetrazol-5-yl)phenyl)-6-(4-fluorophenyl)-3-hydroxypyridin-2(1H)-one

To a sealed tube equipped with a small stirring bar was added 5-(3-cyanophenyl)-6-(4-fluorophenyl)-3-hydroxypyridin-2(1H)-one (48 mg, 0.141 mmol), DMF (2.0 ml), $NaN_3$ (41 mg, 0.628 mmol) followed by AcOH (1.0 ml). The resulting mixture was heated to 120° C. for 4 h. After the completion of the reaction, the solvent was removed under reduced pressure. Addition of 3N HCl and stirring produced a solid which was filtered to give the pure product (35 mg, 63% yield). $^1H$ NMR (300 MHz, DMSO-$d_6$) δ: 9.45 (bs, 1H), 7.92-7.81 (m, 2H), 7.36 (t, 1H), 7.20 (m, 2H), 7.07 (m, 2H), 6.88 (s, 1H).

Example 54

Preparation of Compound

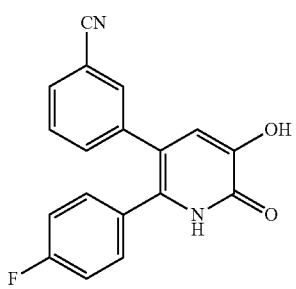 [SMILES: N#Cc1cccc(-c2cc(O)c(=O)[nH]c2-c2ccc(F)cc2)c1]

3-(2-(4-Fluorophenyl)-5-hydroxy-6-oxo-1,6-dihydropyridin-3-yl)benzonitrile

To a solution of 5-(3-cyanophenyl)-6-(4-fluorophenyl)-2,3-dimethoxypyridine (114 mg, 0.34 mmol) in $CH_2Cl_2$ (2.0 ml) under nitrogen, was added boron tribromide (1.5 ml of a 1.0 M solution in CH$_2$Cl$_2$). After addition was completed, the reaction mixture was stirred for 20 h at room temperature. Dichloromethane was removed from the reaction mixture followed by addition of HCl (3N). The resulting solid was filtered. The solid was redissolved in CH$_2$Cl$_2$ and washed with NaHCO$_3$ and brine. The organic phase was then dried and evaporated under reduced pressure to afford the crude product which was purified in ISCO using 5% MeOH in DCM to furnish the pure product (95 mg) as white solid, yield: 91%. $^1$H NMR (300 MHz, DMSO-d$_6$) δ: 7.57 (s, 1H), 7.47 (s, 1H), 7.40 (m, 2H), 7.25 (m, 2H), 7.08 (m, 3H).

The requisite intermediate was prepared as follows a. Preparation of Compound

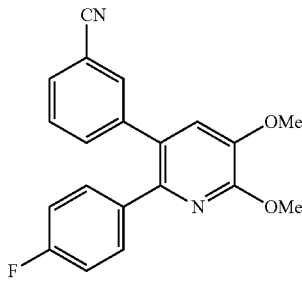 [SMILES: COc1cc(-c2cccc(C#N)c2)c(-c2ccc(F)cc2)nc1OC]

A mixture of 6-bromo-5-(3-cyanophenyl)-2,3-dimethoxypyridine (150 mg, 0.47 mmol), 4-fluorophenylboronic acid (99 mg, 0.70 mmol), Pd(PPh$_3$)$_4$ (70 mg, 0.06 mmol) and K$_2$CO$_3$ (129 mg, 0.94 mmol) in 1,4-dioxane (3.0 ml) and H$_2$O (1.0 ml) was degassed for 30 min. This mixture was heated to 100° C. and stirred for 16 h. The reaction mixture was cooled to room temperature and partitioned between NaHCO$_3$ and EtOAc (3×), and washed with NaCl (1×). The organic phase was dried over Na$_2$SO$_4$ and was concentrated. The resulting residue was purified by ISCO flash chromatography using 25% EtOAc in hexane to give 114 mg (74% yield) desired product. LC/MS: 335 (M+H).

Example 55

Preparation of Compound

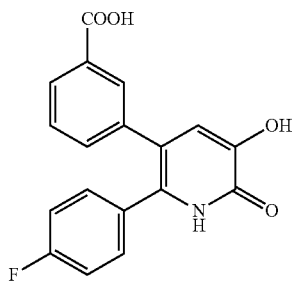 [SMILES: O=C(O)c1cccc(-c2cc(O)c(=O)[nH]c2-c2ccc(F)cc2)c1]

3-(2-(4-Fluorophenyl)-5-hydroxy-6-oxo-1,6-dihydropyridin-3-yl)benzoic acid

To a solution of 5(3-benzoate)-6-(4-fluorophenyl)-2,3-dimethoxypyridine (90 mg, 0.245 mmol) in DCM (3.0 ml) under nitrogen, boron tribromide (1.5 ml of 1.0 M solution in CH$_2$Cl$_2$) was added. After addition was completed, the reaction mixture was refluxed for 16 h. The solvent was removed from the reaction mixture and the resulting solid was purified in ISCO using 10% MeOH in DCM with 1% acetic acid to furnish the pure product (45 mg) yield: 56%. $^1$H NMR (300 MHz, DMSO-d$_6$) δ: 7.74 (d, J=7.2 Hz, 1H), 7.60 (s, 1H), 7.33 (t, 1H), 7.26-7.08 (m, 5H), 6.85 (s, 1H).

The requisite intermediates were prepared as follows a. Preparation of Compound

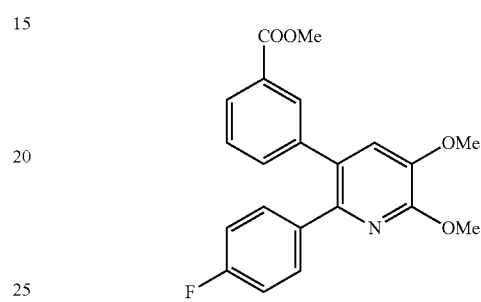

A mixture of 6-bromo-5-(3-benzoate)-2,3-dimethoxypyridine (100 mg, 0.28 mmol), 4-fluorophenylboronic acid (60 mg, 0.43 mmol), Pd(PPh$_3$)$_4$ (46 mg, 0.04 mmol) and K$_2$CO$_3$ (77 mg, 0.56 mmol) in 1,4-dioxane (3.0 ml) and H$_2$O (1.0 ml) was degassed for 30 min. This mixture was heated to 100° C. and stirred for 16 h. The reaction mixture was cooled to room temperature and partitioned between NaHCO$_3$ and EtOAc (3×), and washed with NaCl (1×). The organic phase was dried over Na$_2$SO$_4$ and was concentrated. The resulting residue was purified by ISCO flash chromatography using 15% EtOAc in hexane to give 96 mg (92% yield) desired product. $^1$H NMR (300 MHz, CDCl$_3$) δ: 8.15-8.09 (m, 2H), 7.50-7.41 (m, 3H), 7.08-7.02 (m, 3H), 6.96-6.91 (m, 1H), 4.27 (s, 3H), 4.11 (s, 3H), 4.09 (s, 3H).

b. Preparation of Compound

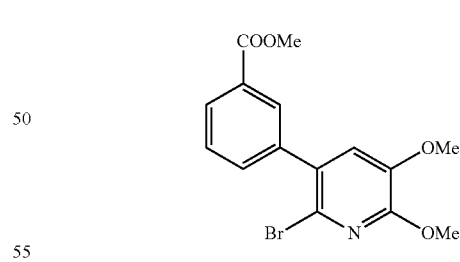

To a solution of 2,3-dimethoxy-5-(3-carbomethoxyphenyl)pyridine (500 mg, 1.83 mmol) in acetic acid (4.5 ml) was added sodium acetate (746 mg, 5.5 mmol). The reaction mixture was cooled to 0° C. and Br$_2$ (0.1 ml) in acetic acid (1.0 ml) was added dropwise. The reaction mixture was stirred at room temperature for 6 h. To this mixture 25% NaOH was added at 0° C. until pH 6 and then extracted with dichloromethane three times. Organic layer wad dried, concentrated under reduced pressure and purified by ISCO using 100% DCM to afford pure product 210 mg, yield: 32%.

c. Preparation of Compound

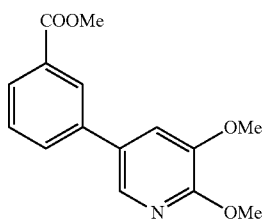 [SMILES: COC(=O)c1cccc(-c2cnc(OC)c(OC)c2)c1]

A mixture of 5-bromo-2,3-dimethoxypyridine (520 mg, 2.39 mmol), 3-carbomethoxyphenylboronic acid (560 mg, 3.12 mmol), Pd(PPh$_3$)$_4$ (346 mg, 0.3 mmol) and K$_2$CO$_3$ (657 mg, 4.76 mmol) in 1,4-dioxane (5.0 ml) and H$_2$O (1.5 ml) was degassed for 30 min. This mixture was heated to 100° C. and stirred for 16 h. The reaction mixture was cooled to room temperature and partitioned between NaHCO$_3$ and EtOAc (3×), and washed with NaCl (1×). The organic phase was dried over Na$_2$SO$_4$ and was concentrated. The resulting residue was purified by ISCO flash chromatography using DCM to give 540 mg (83% yield) desired product. $^1$H NMR (300 MHz, CDCl$_3$) δ: 8.21 (s, 1H), 8.02 (d, J=7.8 Hz, 1H), 7.97 (d, J=1.8 Hz, 1H), 7.73 (d, J=6.6 Hz, 1H), 7.52 (t, 1H), 7.27 (d, J=1, 2 Hz, 1H), 4.07 (s, 3H), 3.96 (s, 3H), 3.95 (s, 3H).

Example 56

Preparation of Compound

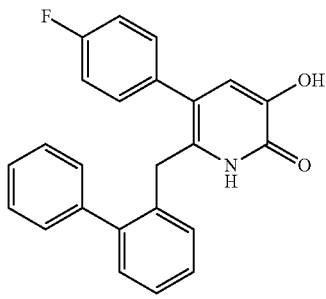 [SMILES: O=c1[nH]c(Cc2ccccc2-c2ccccc2)c(-c2ccc(F)cc2)cc1O]

To a solution of 2-([1,1'-biphenyl]-3-yl)-3-(4-fluorophenyl)-5,6-dimethoxypyridine (182 mg, 0.46 mmol) in DCM (3.0 ml) under nitrogen, boron tribromide (1.5 ml of 1.0 M solution in CH$_2$Cl$_2$) was added. After addition was completed, the reaction mixture was stirred at room temperature overnight. The solvent was removed from the reaction mixture and it was redissolved in DCM. The organic layer was washed with water, sodium bicarbonate followed by brine. After drying with sodium sulfate, the solvent was removed under vacuum and the resulting residue was purified in ISCO using 100% ethyl acetate to furnish the pure product (45 mg), yield: 27%.

The requisite intermediates were prepared as follows a. Preparation of Compound

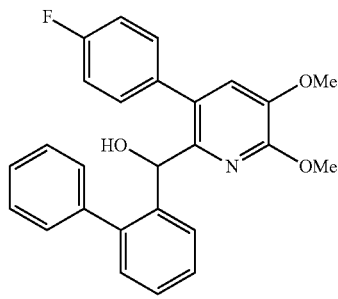 [SMILES: COc1cc(-c2ccc(F)cc2)c(C(O)c2ccccc2-c2ccccc2)nc1OC]

To a solution of 6-bromo-5-(4-fluorophenyl)-2,3-dimethoxypyridine (300 mg, 0.96 mmol) in THF (10 ml) was added n-BuLi (0.96 ml, 1.6 M in hexane) drop-wise at −78° C. The reaction mixture was stirred for 30 minutes at this temperature after which [1,1'-biphenyl]-3-carbaldehyde (262 mg, 1.44 mmol) in THF (2.0 ml) was added. The reaction mixture was further stirred for 30 minutes after which it was poured into ice-water (8.0 ml). Extraction with ethyl acetate, the organic layers were dried, evaporated and the crude product is further purified by ISCO using 25% ethyl acetate in hexane to afford the pure product (306 mg), yield: 76%.

b. Preparation of Compound

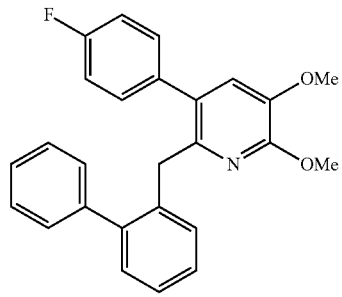 [SMILES: COc1cc(-c2ccc(F)cc2)c(Cc2ccccc2-c2ccccc2)nc1OC]

To a solution of [1,1'-biphenyl]-2-yl(3-(4-flurorphenyl)-5,6-dimethoxypyridin-2-yl)methanol (323 mg, 0.56 mmol) in DCE (8.0 ml) was added TFA (1.0 ml) and Et$_3$SiH (130 mg, 1.12 mmol) at 0° C. under N$_2$. The reaction mixture was heated at 80° C. for 3 h after which the solvents are removed and the residue was dissolved in ethyl acetate. The organic layer after washed with NaHCO$_3$ and brine was dried, evaporated and the crude product was purified by ISCO using 30% EtOAc in hexane to afford the pure product (186 mg), yield: 83%.

Example 57

Preparation of Compound

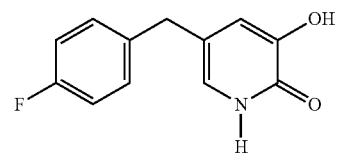 [SMILES: O=c1[nH]cc(Cc2ccc(F)cc2)cc1O]

5-(4-Fluorobenzyl)-3-hydroxypyridin-2(1H)-one

To a solution of 5-(4-fluorobenzyl)2,3-dimethoxypyridine (25 mg, 0.1 mmol) in CH$_2$Cl$_2$ (3.0 ml) under nitrogen, was added boron tribromide (1.0 M solution in CH$_2$Cl$_2$) (0.3 ml). After addition was completed, the reaction mixture was stirred for 16 h at room temperature. The solvent was removed from the reaction mixture and the residue was redissolved in CH$_2$Cl$_2$. The organic layer was washed with NaHCO$_3$ and brine, dried using anhydrous sodium sulfate and evaporated under reduced pressure to afford a crude solid which was further purified using 10% MeOH in DCM to afford the desired product (12 mg), yield: 54%. ¹H NMR (300 MHz, MeOD-d₄) δ: 7.11 (m, 2H), 6.92 (m, 2H), 6.63 (d, J=9.9 Hz, 2H), 3.60 (s, 2H).

The requisite intermediates were prepared as follows a. Preparation of Compound

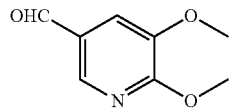

To a solution of 5-bromo-2,3-dimethoxypyridine (217 mg, 1.0 mmol) in THF (6.0 ml) was added at −78° C. under argon a solution of n-BuLi (2 ml, 1.6 M solution in hexane). After stirring for 1 h at this temperature anhydrous DMF (0.4 ml) was added and the reaction was stirred for an additional 30 min. The reaction was quenched by the addition of Sat. NH₄Cl and was extracted with ethyl acetate three times. Combined organic layers were dried in sodium sulfate and after the removal of the solvent the crude product was purified by ISCO using 20% EtOAc in hexane to afford the pure product (52 mg), yield: 31%. ¹H NMR (300 MHz, CDCl₃) δ: 9.94 (s, 1H), 8.21 (s, 1H), 7.48 (s, 1H), 4.12 (s, 3H), 3.94 (s, 3H).

b. Preparation of Compound

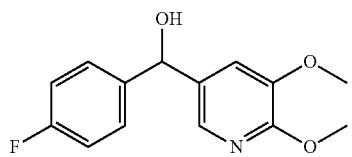 [SMILES: COc1cc(C(O)c2ccc(F)cc2)cnc1OC]

A solution of 4-fluorophenyl magnesium bromide (3 ml, 1.0 M in THF) was added to a solution of 5-formyl-2,3-dimethoxypyridine (220 mg, 1.32 mmol) in Et₂O (30 ml) keeping the internal temperature at −40° C. for 1 h. The reaction was allowed to warm to 0° C. and was quenched with the addition of sat. NH₄Cl. The mixture was extracted with ether and the combined organic layers were washed with water and brine to afford the pure product (330 mg), yield: 95%. ¹H NMR (300 MHz, CDCl₃) δ: 7.52 (s, 1H), 7.27-7.22 (m, 2H), 6.98-6.92 (m, 3H), 5.66 (s, 1H), 3.91 (s, 3H), 3.73 (s, 3H).

c. Preparation of

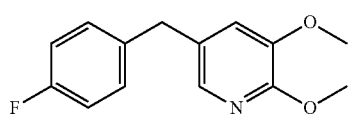 [SMILES: COc1cc(Cc2ccc(F)cc2)cnc1OC]

To a solution of (5,6-dimethoxypyridin-3-yl)(4-fluorophenyl)methanol (75 mg, 0.28 mmol) in DCM (5.0 ml) was added TFA (2 drops) and Et₃SiH (66 mg) at 0° C. under N₂. The reaction mixture was stirred at room temperature for 18 h after which the solvents are removed and the residue was redissolved in DCM. The combined organic layers after washed with NaHCO₃ and brine was dried, evaporated and the crude product was purified by ISCO using 20% EtOAc in hexane to afford the pure product (40 mg), yield: 58%. NMR (300 MHz, CDCl₃) δ: 7.58 (s, 1H), 7.16-7.11 (m, 2H), 7.01-6.96 (m, 2H), 6.80 (s, 1H), 4.08 (s, 3H), 3.88 (s, 3H), 3.81 (s, 3H).

Example 58

Preparation of Compound

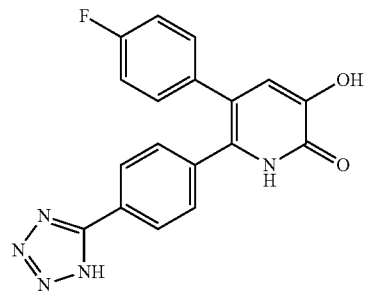 [SMILES: O=c1[nH]c(-c2ccc(-c3nnn[nH]3)cc2)c(-c2ccc(F)cc2)cc1O]

5-(4-Fluorophenyl)-6-[4-(1H-tetrazol-5-yl)phenyl]-3-hydroxypyridin-2(1H)-one

To a sealed tube equipped with a small stirring bar was added 5-(4-fluorophenyl)-6-(4-cyanophenyl)-3-hydroxypyridin-2(1H)-one (50 mg, 0.16 mmol), DMF (2.0 ml), NaN₃ (42 mg, 0.64 mmol) followed by AcOH (1.0 ml). The resulting mixture was heated to 120° C. overnight. After completion of the reaction, the solvent was removed under vacuum. Addition of 1N HCl and stirring produced a solid which was filtered to give the pure product (30 mg, 54% yield). ¹H NMR (300 MHz, DMSO-d₆) δ: 7.83 (d, J=8.1 Hz, 2H), 7.14 (d, J=8.1 Hz, 2H), 7.09-7.00 (m, 4H), 6.81 (s, 1H). HRMS Calcd for C₁₈H₁₂FN₅O₂ (M+H)⁺ 350.1048. Found 350.1058.

Example 59

Preparation of Compound

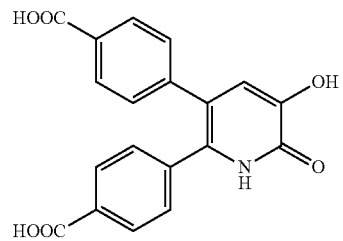 [SMILES: O=C(O)c1ccc(-c2cc(O)c(=O)[nH]c2-c2ccc(C(=O)O)cc2)cc1]

To a solution of bis-5,6-dimethyl benzoate-2,3-dimethoxypyridine (116 mg, 0.285 mmol) in DCM (3.0 ml) under nitrogen, boron tribromide (1.5 ml of 1.0 M solution in CH₂Cl₂) was added. After addition was completed, the reaction mixture was stirred for 16 h. The solvent was removed from the reaction mixture and the resulting solid was redissolved in ethyl acetate and the organic layer was washed with sodium bicarbonate. The aqueous layer was acidified to pH 1 and was extracted with ethyl acetate. The combined organic layers was dried and the solvent was removed to afford the pure product (68 mg), yield: 68%. NMR (300 MHz, DMSO-$d_6$) δ: 9.56 (bs, 1H), 7.83-7.76 (m, 3H), 7.28 (d, J=8.4 Hz, 2H), 7.16 (d, J=8.1 Hz, 2H), 6.88 (s, 1H).

The requisite intermediate was prepared as follows a. Preparation of Compound

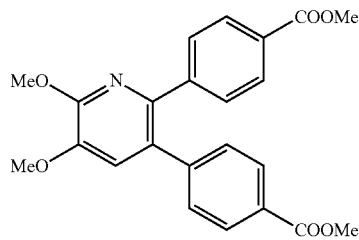 [SMILES: COC(=O)c1ccc(-c2cc(OC)c(OC)nc2-c2ccc(C(=O)OC)cc2)cc1]

4,4'-(5-hydroxy-6-oxo-1,6-dihydropyridine-2,3-diyl) dibenzoic acid

A mixture of 5,6-dibromo-2,3-dimethoxypyridine (400 mg, 1.8 mmol), 4-acetoxyphenylboronic acid (648 mg, 3.6 mmol), Pd(PPh$_3$)$_4$ (415 mg, 0.36 mmol) and K$_2$CO$_3$ (993 mg, 7.0 mmol) in 1,4-dioxane (6.0 ml) and H$_2$O (2.0 ml) was degassed for 30 min. This mixture was heated to 100° C. and stirred for 16 h. The reaction mixture was cooled to room temperature and partitioned between NaHCO$_3$ and EtOAc (3×), and washed with NaCl (1×). The organic phase was dried over Na$_2$SO$_4$ and was concentrated. The resulting residue was purified by ISCO flash chromatography using 15% EtOAc in hexane to give 120 mg (17% yield) desired product. LC/MS: 408.

Example 60

Protein Expression, Purification, and Crystallization

Pandemic 2009 H1N1 influenza A endonuclease (residues 1-204) was expressed in BL21 (RIL) cells (Stratagene). The BL21 cells were grown to an OD$_{600}$ of 0.8 and induced with 0.2 mM IPTG at 17 degrees Celsius for 17 hours. Cells were harvested by centrifugation and purified on Ni-NTA (Qiagen) according to the manufacturers recommendations. The dual hexa-His tag was then removed by 3C protease cleavage. S2C was further purified by size exclusion chromatography using HiLoad 26/60 Superdex 75 (GE Heathcare). The buffer used for size exclusion and the final buffer for storage of the protein was 100 mM NaCl and 20 mM Tris pH 8.0. The protein was concentrated to 10 mg/ml using a Ultrafree 10K (Millipore), aliquoted and stored at −80 degrees Celsius.

Crystals were formed by mixing in a 1:1 ratio endonuclease (5 mg/ml) with crystallization buffer containing 200 mM MES pH 6.7, 27% (w/v) PEG8000, 200 mM ammonium sulfate, 1 mM manganese chloride, 10 mM magnesium acetate, 10 mM taurine and 50 mM sodium fluoride. Trays were stored at 20 degrees Celsius and crystals formed within a few hours and grew to maximum size in one to two weeks.

Example 61

Compound Soaking, Data Collection, and Processing

Crystal structure and modeling studies were carried out for improving influenza A inhibition and specificity of the compounds derived from formula I (Bauman et al.; ACS Chem Bio. 2013; Epub Aug. 26, 2013). Most soaks of ligands were performed by taking crystals and by step-wise gradient shifting the surrounding crystallization solution to 1 mM manganese sulfate, 200 mM HEPES pH 7.7, 25% (w/v) PEG 8000, 50 mM ammonium sulfate, 5 mM magnesium acetate, and 10% (v/v) ethylene glycol. 80-100 mM L-arginine was included to improve solubility of the compounds. Crystals were then soaked with the ligand for 2-17 hours at 20 degrees Celsius before placing into liquid nitrogen for storage. X-ray diffraction data collection was performed at the Cornell High Energy Synchrotron Source (CHESS) F1 beamline and the National Synchrotron Light Source (NSLS) beamlines X25 and X29. The diffraction data were indexed, processed, scaled and merged using HKL2000 (Otwinowski et al., Meth Enzymol. 1997; 276: 307-26). Datasets containing bound fragments were further processed using CCP4 (Winn et al.; Acta Cryst. 2011; D67:235-42) and PHENIX (Afonine et al.; Acta Cryst. 2012; D68:352-67).

X-ray crystal structures of I and derivatives in complex with 2009 H1N1 influenza A endonuclease enzyme revealed a novel mode of chelation of the compounds to two metal ions ($Mg^{2+}$ or $Mn^{2+}$ at the positions M1 and M2) at the active site. Structures and subsequent modeling suggested possibilities of chemical substitutions at positions 4, 5 and 6.

A wide variety of substituents can be accommodated at the positions 5 and 6. Steric factors with influenza endonuclease appear to constrain the number of substituents that are well tolerated at the 4-position. The presence of a 6-phenyl substituent tends to significantly increase the accommodation of more varied substituents at the 5-position and to a lesser extent at the 4-position. Some of the predicted derivatives of I have been synthesized and tested for inhibition of influenza A endonuclease activity (Example 63). X-ray crystal structures of derivatives of I were determined in complex with 2009 H1N1 influenza A endonuclease enzyme for deriving effective 3D SAR that guided future synthesis cycles.

The ability of a compound to inhibit endonuclease activity can be evaluated using known assays or using the assay described in Example 62. The novel assay described in Example 62 represents part of the invention.

Example 62

Endonuclease Assay

The $PA_N$ domain has been shown to cleave ssRNA as well as ssDNA. To demonstrate the inhibition of endonuclease cleavage by $PA_N$, a high throughput assay was developed (U.S. patent application Ser. No. 13/554,709; Sagong et al.; ACS Med Chem Lett. 2013; 4(6): 547-550). A TaqMan-like oligonucleotide was used containing a 6-carboxy-fluorescein (FAM) fluorophore at the 5'-end followed by 19 nucleotides and a minor groove binding non-fluorescent quencher (MGBNFQ, Applied Biosystems) at the 3'-end. When excited by light at a wavelength of 488 nm, MGBNFQ quenches the fluorescence of FAM via fluorescence resonance energy transfer. If the endonuclease cleaves the oligonucleotide, the quencher is no longer coupled to the fluorophore, and therefore, FAM fluoresces. This assay can be performed in a high-throughput (e.g. 96 well plate) format. The assay can be used to evaluate the inhibitory characteristics of compounds that are found to bind $PA_N$ and to screen libraries of drug-like compounds. The assay uses the probe 6FAM-TGGCAATATCAGCTCCACA-MGB-NFQ The assay can be performed in a 40 µl reaction volume with 50 mM Tris pH 7.5, 50 mM NaCl, 1 mM $MgSO_4$, 0.05 mM $MnSO_4$, 1 mM DTT, 0.75 mM CHAPS, 50 nM probe, and 25 nM endonuclease.

The reaction mixture is set up as a master mix with the buffer, probe, and protein on ice. The inhibitor is then added to a maximum DMSO concentration of 2.5% (v/v) and serial dilutions are made on ice. Varioskan Fluorometer (Thermo Scientific), set to an excitation of 488 nm and emission of 518 nm, is used to measure the fluorescence of the samples at 37 degrees Celsius. Fluorescence is measured at various time points (5, 120, and 240 minutes) during the 37 degrees Celsius incubation. Activity/inhibition is calculated based on the change in fluorescence over time using Prism Graphpad non-linear regression analysis.

Data for representative compounds of formula I in the endonuclease inhibition assay described above is provided in the following table.

| Chemical Name | Structure | $IC_{50}$ (uM) using either 500 nM or 50 nM enzyme |
|---|---|---|
| 5-Chloro-3-hydroxypyridin-2(1H)-one | 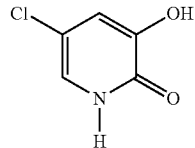 | 5.0 |
| 5-Bromo-3-hydroxypyridin-2(1H)-one | 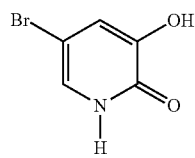 | 5.0 |
| 6-(4-Fluoro-phenyl)-3-hydroxypyridin-2(1H)-one | 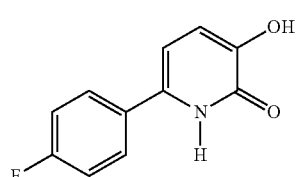 | 0.43 |
| 6-(4-(tert-Butyl)phenyl)-3-hydroxypyridin-2(1H)-one | 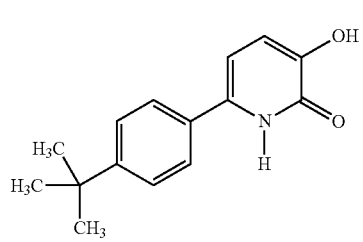 [SMILES: CC(C)(C)c1ccc(-c2ccc(O)c(=O)[nH]2)cc1] | 1.6 |
| 3-Hydroxy-6-(4-(trifluoromethyl)phenyl)pyridin-2(1H)-one | 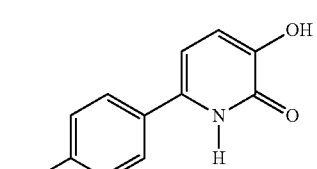 | 0.4 |
| 3-Hydroxy-6-phenylpyridin-2(1H)-one | 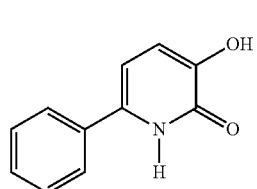 | 0.38 |

-continued
| Chemical Name | Structure | IC$_{50}$ (uM) using either 500 nM or 50 nM enzyme |
|---|---|---|
| 3-Hydroxy-6-(4-methoxyphenyl)pyridin-2(1H)-one | 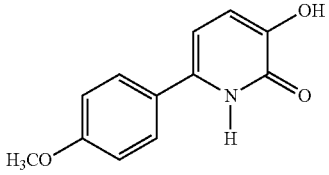 [SMILES: COc1ccc(-c2ccc(O)c(=O)[nH]2)cc1] | 1.2 |
| 6-(3-Fluorophenyl)-3-hydroxypyridin-2(1H)-one | 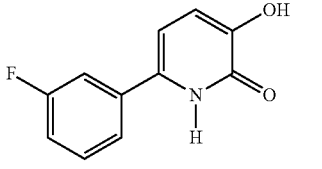 [SMILES: O=c1[nH]c(-c2cccc(F)c2)ccc1O] | 0.53 |
| 6-(3-Methoxyphenyl)-3-hydroxypyridin-2(1H)one | 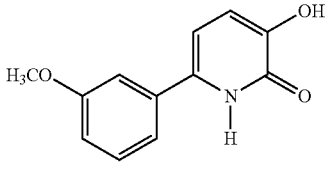 [SMILES: COc1cccc(-c2ccc(O)c(=O)[nH]2)c1] | 0.54 |
| 6-(Cyclohex-1-en-1-yl)-3-hydroxypyridin-2(1H)-one | 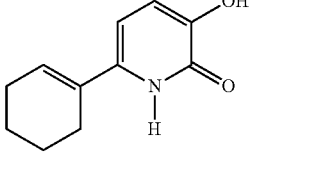 | 0.75 |
| 6-(3,4-Dihydroxyphenyl)-3-hydroxypyridin-2(1H)-one | 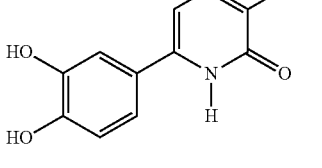 | 0.60 |
| 6-Cyclohexyl-3-hydroxypyridin-2(1H)-one | 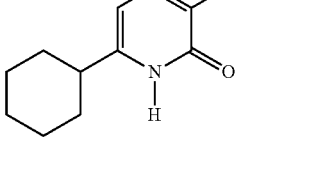 | 2.5 |
| 5,6-bis(4-Fluorophenyl)-3-hydroxypyridin-2(1H)-one | 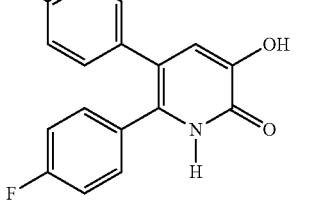 | 0.041 |

-continued
| Chemical Name | Structure | IC$_{50}$ (uM) using either 500 nM or 50 nM enzyme |
|---|---|---|
| 5,6-bis(3-Fluorophenyl)-3-hydroxypyridin-2(1H)-one | 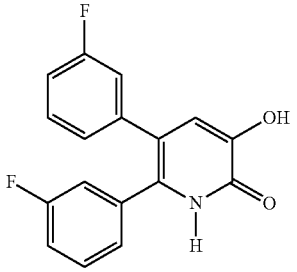 [SMILES: O=c1[nH]c(-c2cccc(F)c2)c(-c2cccc(F)c2)cc1O] | 0.044 |
| 5,6-bis(phenyl)-3-hydroxypyridin-2(1H)-one | 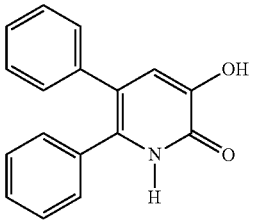 [SMILES: O=c1[nH]c(-c2ccccc2)c(-c2ccccc2)cc1O] | 0.047 |
| 3-Hydroxy-5,6-bis(4-nitrophenyl)pyridin-2(1H)-one | 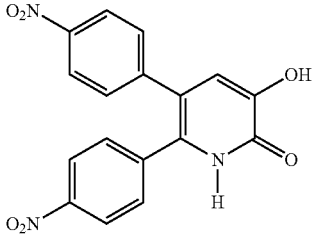 [SMILES: O=c1[nH]c(-c2ccc([N+](=O)[O-])cc2)c(-c2ccc([N+](=O)[O-])cc2)cc1O] | 0.72 |
| 4,4'-(6-Oxo-1,6-dihydropyridine-2,3-diyl)-dibenzamide | 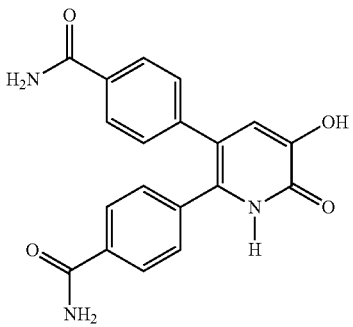 [SMILES: NC(=O)c1ccc(-c2cc(O)c(=O)[nH]c2-c2ccc(C(N)=O)cc2)cc1] | 0.23 |
| 3,3'-(6-Oxo-1,6-dihydropyridine-2,3-diyl)-dibenzamide | 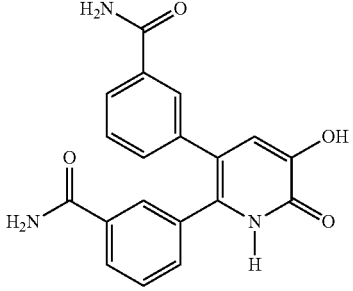 [SMILES: NC(=O)c1cccc(-c2cc(O)c(=O)[nH]c2-c2cccc(C(N)=O)c2)c1] | 0.11 |

-continued

| Chemical Name | Structure | IC$_{50}$ (uM) using either 500 nM or 50 nM enzyme |
|---|---|---|
| 5,6-Dibromo-3-hydroxypyridin-2(1H)-one | 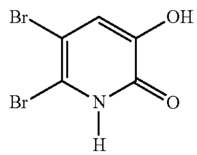 | 1.5 |
| 6-Bromo-5-(4-fluorophenyl)-3-hydroxypyridin-2(1H)-one and 5-Bromo-4-(4-fluorophenyl)-3-hydroxypyridin-2(1H)-one | | 0.187 |
| 6-Bromo-5-(3-fluorophenyl)-3-hydroxypyridin-2(1H)-one and 6-Bromo-5-(3-fluorophenyl)-3-hydroxypyridin-2(1H)-one | | 0.36 |
| 5-(4-Fluorophenyl)-3-hydroxypyridin-2(1H)-one | 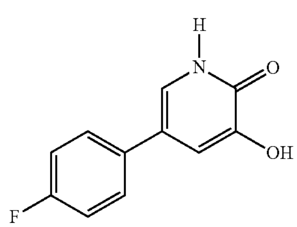 [SMILES: O=c1[nH]cc(-c2ccc(F)cc2)cc1O] | 0.73 |
| 6-Bromo-5-(4-fluorophenyl)-3-hydroxypyridin-2(1H)-one | 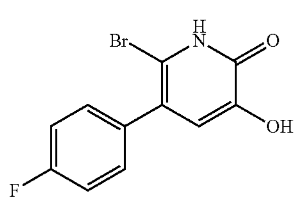 [SMILES: O=c1[nH]c(Br)c(-c2ccc(F)cc2)cc1O] | 4.2 |
| 5-Bromo-6-(3-fluorophenyl)-3-hydroxypyridin-2(1H)-one | 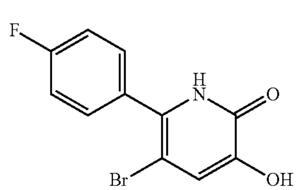 [SMILES: O=c1[nH]c(-c2ccc(F)cc2)c(Br)cc1O] | 0.15 |

-continued

| Chemical Name | Structure | IC$_{50}$ (uM) using either 500 nM or 50 nM enzyme |
|---|---|---|
| 6-(4-Fluorophenyl)-5-hydroxypyrimidin-4(3H)-one | 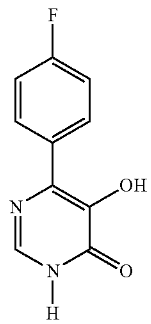 [SMILES: O=c1[nH]cnc(-c2ccc(F)cc2)c1O] | 193 |
| 2-(4-Fluorophenyl)-5-hydroxypyrimidin-4(3H)-one | 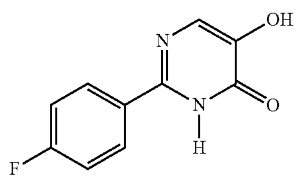 [SMILES: O=c1[nH]c(-c2ccc(F)cc2)ncc1O] | 0.58 |
| 4-(5-Hydroxy-6-oxo-1,6-dihydropyrimidin-2-yl)benzonitrile | 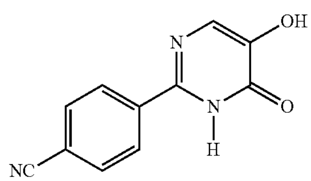 [SMILES: N#Cc1ccc(-c2ncc(O)c(=O)[nH]2)cc1] | 0.52 |
| 2-(4-(1H-Tetrazol-5-yl)phenyl)-5-hydroxypyrimidin-4(3H)-one | 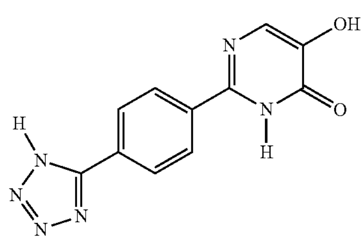 [SMILES: O=c1[nH]c(-c2ccc(-c3nnn[nH]3)cc2)ncc1O] | 0.15 |
| 3-(5-Hydroxy-6-oxo-1,6-dihydropyrimidin-2-yl)benzonitrile | 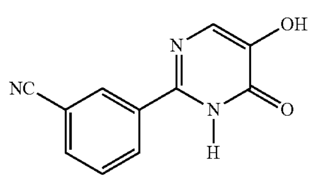 [SMILES: N#Cc1cccc(-c2ncc(O)c(=O)[nH]2)c1] | 0.25 |
| 2-(3-(1H-Tetrazol-5-yl)phenyl)-5-hydroxypyrimidin-4(3H)-one | 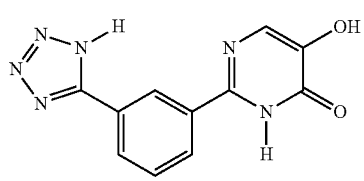 [SMILES: O=c1[nH]c(-c2cccc(-c3nnn[nH]3)c2)ncc1O] | 0.48 |

-continued

| Chemical Name | Structure | IC$_{50}$ (uM) using either 500 nM or 50 nM enzyme |
|---|---|---|
| 5-(4-Fluorophenyl)-4-hydroxypyridazin-3(2H)-one | 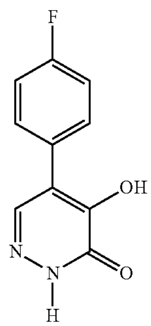 [SMILES: O=c1[nH]ncc(-c2ccc(F)cc2)c1O] | >200 |
| 6-(4-Fluorophenyl)-4-hydroxypyridazin-3(2H)-one | 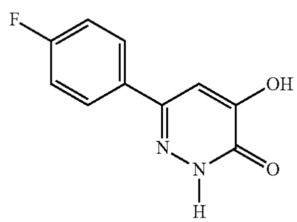 [SMILES: O=c1[nH]nc(-c2ccc(F)cc2)cc1O] | 6.0 |
| 4-(5-Hydroxy-6-oxo-1,6-dihydropyridazin-3-yl)benzonitrile | 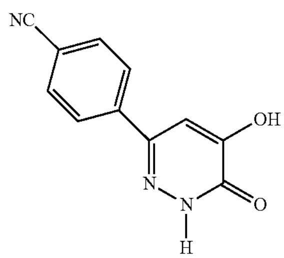 [SMILES: N#Cc1ccc(-c2cc(O)c(=O)[nH]n2)cc1] | 9.3 |
| 6-(4-(1H-Tetrazol-5-yl)phenyl)-4-hydroxypyridazin-3(2H)-one | 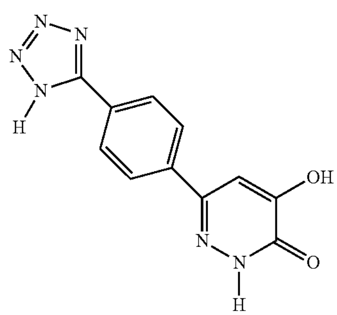 [SMILES: O=c1[nH]nc(-c2ccc(-c3nnn[nH]3)cc2)cc1O] | 3.0 |
| 5-Cyclohexyl-3-hydroxypyridin-2(1H)-one | 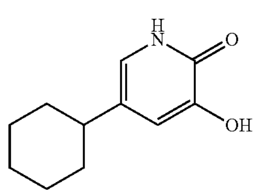 [SMILES: O=c1[nH]cc(C2CCCCC2)cc1O] | 2.1 |
| 5-[3-(1H-Tetrazol-5-yl)phenyl]-3-hydroxypyridin-2(1H)-one | 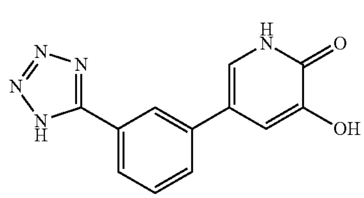 [SMILES: O=c1[nH]cc(-c2cccc(-c3nnn[nH]3)c2)cc1O] | 0.85 |

-continued

| Chemical Name | Structure | IC$_{50}$ (uM) using either 500 nM or 50 nM enzyme |
|---|---|---|
| 3-(5-Hydroxy-6-oxo-1,6-dihydropyridin-3-yl)benzoic acid | 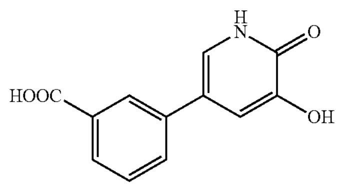 [SMILES: O=C(O)c1cccc(-c2c[nH]c(=O)c(O)c2)c1] | 1.79 |
| 5-(3-Fluorophenyl-3-hydroxypyridin-2(1H)-one | 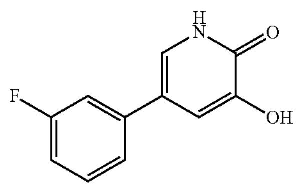 [SMILES: O=c1[nH]cc(-c2cccc(F)c2)cc1O] | 0.74 |
| 4-(5-Hydroxy-6-oxo-1,6-dihydropyridin-3-yl)benzoic acid | 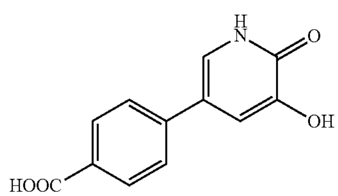 [SMILES: O=C(O)c1ccc(-c2c[nH]c(=O)c(O)c2)cc1] | 0.51 |
| 3,3'-(5-Hydroxy-6-oxo-1,6-dihydropyridine-2,3-diyl)dibenzoic acid | 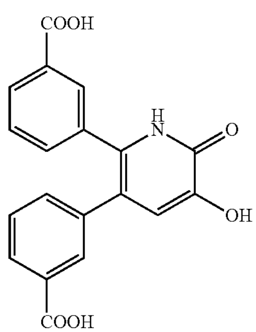 [SMILES: O=C(O)c1cccc(-c2cc(O)c(=O)[nH]c2-c2cccc(C(=O)O)c2)c1] | 0.70 |
| 5-Phenyl-3-hydroxypyridin-2(1H)-one | 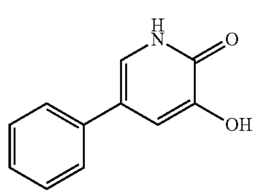 [SMILES: O=c1[nH]cc(-c2ccccc2)cc1O] | >10 |
| 5-(p-Cyanophenyl-3-hydroxypyridin-2(1H)-one | 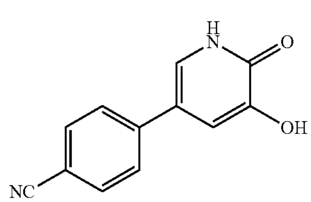 [SMILES: N#Cc1ccc(-c2c[nH]c(=O)c(O)c2)cc1] | 6.07 |

-continued

| Chemical Name | Structure | IC$_{50}$ (uM) using either 500 nM or 50 nM enzyme |
|---|---|---|
| 5-[4-(1H-Tetrazol-5-yl)phenyl]-3-hydroxypyridin-2(1H)-one | 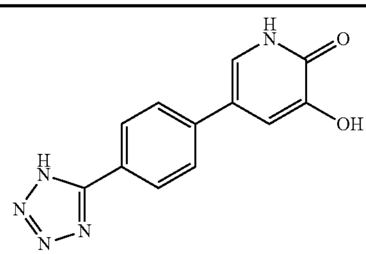 | 0.37 |
| 6-(4-Cyanophenyl-3-hydroxypyridin-2(1H)-one | 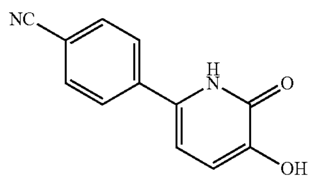 [SMILES: N#Cc1ccc(-c2ccc(O)c(=O)[nH]2)cc1] | 1.2 |
| 6-[4-(1H-tetrazol-5-yl)phenyl]-3-hydroxypyridin-2(1H)-one | 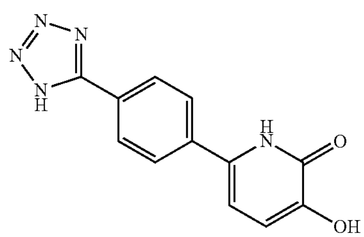 [SMILES: O=c1[nH]c(-c2ccc(-c3nnn[nH]3)cc2)ccc1O] | 0.85 |
| 5,6-bis(4-Cyanophenyl)-3-hydroxypyridin-2(1H)-one | 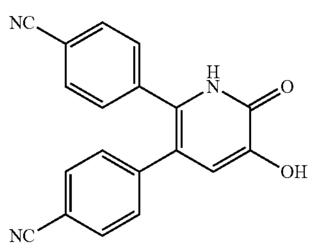 [SMILES: N#Cc1ccc(-c2cc(O)c(=O)[nH]c2-c2ccc(C#N)cc2)cc1] | 0.10 |
| 5,6-bis[4-(1H-Tetrazol-5-yl)phenyl]-3-hydroxypyridin-2(1H)-one | 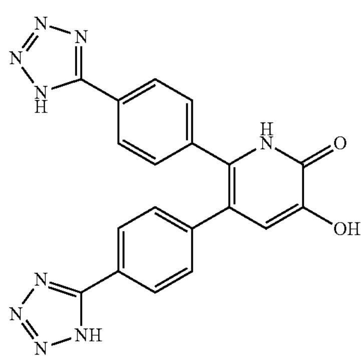 [SMILES: O=c1[nH]c(-c2ccc(-c3nnn[nH]3)cc2)c(-c2ccc(-c3nnn[nH]3)cc2)cc1O] | 0.29 |
| 5-(4-Fluorophenyl)-6-(4-cyanophenyl)-3-hydroxypyridin-2(1H)-one | 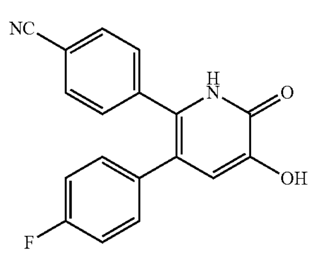 [SMILES: N#Cc1ccc(-c2[nH]c(=O)c(O)cc2-c2ccc(F)cc2)cc1] | 0.054 |

-continued

| Chemical Name | Structure | IC$_{50}$ (uM) using either 500 nM or 50 nM enzyme |
| --- | --- | --- |
| 5-(4-Cyanophenyl)-6-(4-fluorophenyl)-3-hydroxypyridin-2(1H)-one | 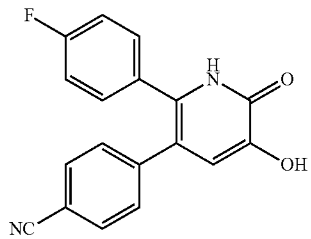 [SMILES: N#Cc1ccc(-c2cc(O)c(=O)[nH]c2-c2ccc(F)cc2)cc1] | 0.136 |
| 5-[4-(1H-Tetrazol-5-yl)phenyl]-6-(4-fluorophenyl)-3-hydroxypyridin-2(1H)-one | 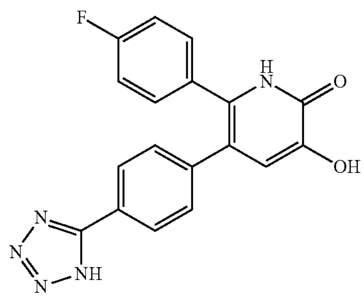 [SMILES: O=c1[nH]c(-c2ccc(F)cc2)c(-c2ccc(-c3nnn[nH]3)cc2)cc1O] | 0.011 |
| 5,6-bis(4-Fluorophenyl)-3-hydroxypyridin-2(1H)-one | 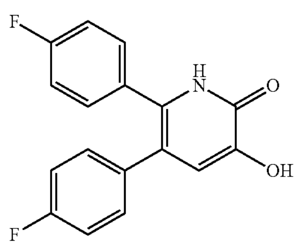 [SMILES: O=c1[nH]c(-c2ccc(F)cc2)c(-c2ccc(F)cc2)cc1O] | 0.176 |
| 5,6-Diphenyl-3-hydroxypyridin-2(1H)-one | 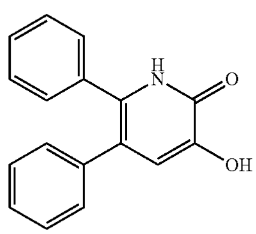 [SMILES: O=c1[nH]c(-c2ccccc2)c(-c2ccccc2)cc1O] | 0.12 |
| 4-((2-(4-Fluorophenyl)-5-hydroxy-6-oxo-1,6-dihydropyridin-3-yl)amino)benzonitrile | 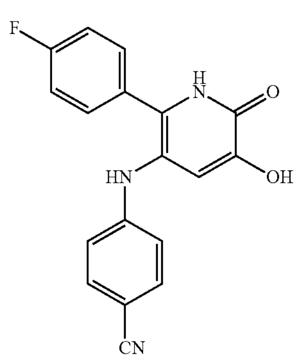 [SMILES: N#Cc1ccc(Nc2cc(O)c(=O)[nH]c2-c2ccc(F)cc2)cc1] | 1.0 |

-continued

| Chemical Name | Structure | IC$_{50}$ (uM) using either 500 nM or 50 nM enzyme |
|---|---|---|
| 5-(3-(1H-Tetrazol-5-yl)phenyl)-6-(4-fluorophenyl)-3-hydroxypyridin-2(1H)-one | 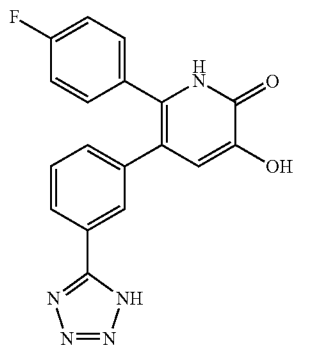 [SMILES: O=c1[nH]c(-c2ccc(F)cc2)c(-c2cccc(-c3nnn[nH]3)c2)cc1O] | 0.034 |
| 3-(2-(4-Fluorophenyl)-5-hydroxy-6-oxo-1,6-dihydropyridin-3-yl)benzonitrile | 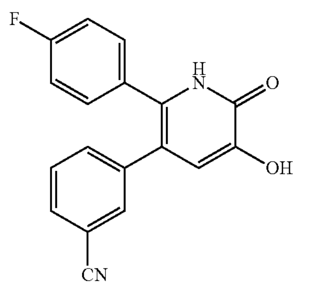 [SMILES: N#Cc1cccc(-c2cc(O)c(=O)[nH]c2-c2ccc(F)cc2)c1] | 0.049 |
| 3-(2-(4-Fluorophenyl)-5-hydroxy-6-oxo-1,6-dihydropyridin-3-yl)benzoic acid | 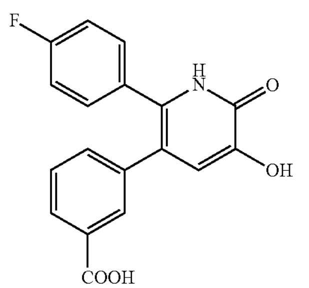 [SMILES: O=C(O)c1cccc(-c2cc(O)c(=O)[nH]c2-c2ccc(F)cc2)c1] | 0.035 |
| 6-([1,1'-Biphenyl]-4-ylmethyl)-5-(4-fluorophenyl)-3-hydroxypyridin-2(1H)-one | 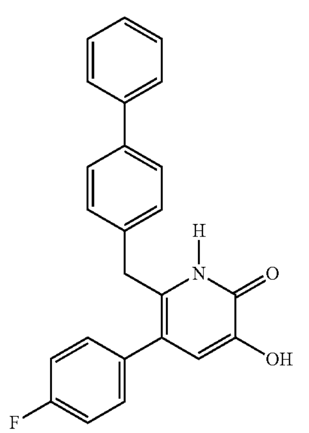 [SMILES: O=c1[nH]c(Cc2ccc(-c3ccccc3)cc2)c(-c2ccc(F)cc2)cc1O] | 0.12 |
| 5-(4-Fluorobenzyl)-3-hydroxypyridin-2(1H)-one | 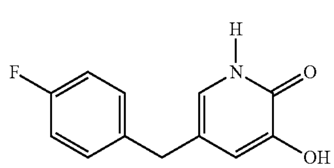 [SMILES: O=c1[nH]cc(Cc2ccc(F)cc2)cc1O] | 8.6 |

| Chemical Name | Structure | IC$_{50}$ (uM) using either 500 nM or 50 nM enzyme |
|---|---|---|
| 6-(4-(1H-Tetrazol-5-yl)phenyl)-5-(4-fluorophenyl)-3-hydroxypyridin-2(1H)-one | 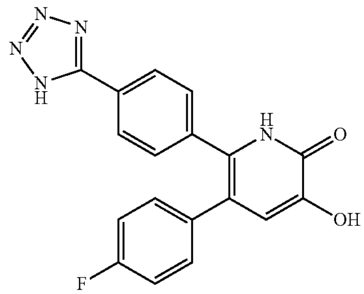 [SMILES: O=c1[nH]c(-c2ccc(-c3nnn[nH]3)cc2)c(-c2ccc(F)cc2)cc1O] | 0.018 |
| 4,4'-(5-hydroxy-6-oxo-1,6-dihydropyridine-2,3-diyl)dibenzoic acid | 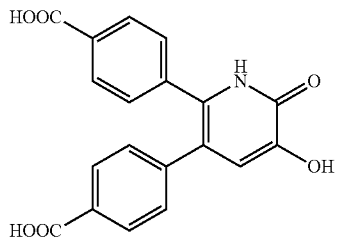 [SMILES: O=C(O)c1ccc(-c2cc(O)c(=O)[nH]c2-c2ccc(C(=O)O)cc2)cc1] | 0.90 |

The anti-influenza activity of a compound of the invention can be evaluated using the assay described in Example 63.

Example 63

Anti-Influenza Activity

Anti-influenza activity of the compounds can be tested as previously described (Bauman et al.; ACS Chem Bio. 2013; Epub 8/26/13).

Madin-Darby canine kidney (MDCK) cells were maintained in Dulbecco's modified Eagle's medium (DMEM) supplemented with 10% (v/v) fetal bovine serum (FBS), and 1% (w/v) penicillin, 100 units mL$^{-1}$; streptomycin, 100 µg mL$^{-1}$; L-glutamine, 2 mM (P-S-G) at 37° C. in a 5% CO$_2$ atmosphere. After viral infections, cells were maintained in DMEM containing 0.3% (w/v) bovine serum albumin (BSA), 1% (w/v) P-S-G, and 1.0 µg mL$^{-1}$ tosyl-sulfonyl phenylalanyl chloromethyl ketone (TPCK)-treated trypsin (Sigma).

Influenza A/Puerto Rico/8/1934 (H1N1; PR8)(Schickli et al.; Phil Tans R Soc B. 2001; 356:1965-1973) was prepared from infected MDCK cells as described previously (Martinez-Sobrido et al.; J Virol. 2010; 84:2157-2163). To determine inhibition of 7, confluent monolayers of MDCK cells (12-well plate format, 10$^6$ cells) were infected in triplicate for 1 hour at room temperature with PR8 at low multiplicity of infection (moi, 0.001). After infection, cells were incubated at 37° C. with 0.1% (v/v) DMSO in the absence or presence of 7 or oseltamivir. Virus titers in tissue culture supernatants at 24 hours post infection were determined by immunofocus assay (fluorescent forming units, FFU) in MDCK cells (Baker et al.; J Virol. 2013; 87:8591-8605). Briefly, triplicate wells of MDCK cells (96-well format, 4×10$^4$ cells) were infected with 10-fold serial dilutions of tissue culture supernatants. Ten hours post infection, presence of virus was detected by immunofluorescence with an influenza NP monoclonal antibody (HT103). Mean value and standard deviations were calculated using GraphPad Prism 6.0b software.

Cytotoxicity of compounds can be determined as described. Triplicate, 50% confluent monolayers of MDCK cells (96-well format, 2×10$^4$ cells) were incubated in media containing 0.1% (v/v) DMSO in the absence or presence of the indicated drugs for 24 hours. Cytotoxicity was then determined by CellTiter96 assay (Promega) by reading absorbance of formazan product at 570 nm (Vmax kinetic microplate reader, Molecular Devices).

Viral yield inhibition assay and cytotoxicity assay. Virus yield assay using MDCK cells and the A/Puerto Rico/8/1934 (H1N1) influenza strain was used to determine the antiviral activity of for 6-(4-fluorophenyl)-3-hydroxy-5-[4-(1H-1,2,3,4-tetrazol-5-yl)phenyl]-1H-pyridin-2-one; oseltamivir and 0.1% (v/v) DMSO (only) were used as the positive and negative controls. Cytotoxicity for 6-(4-fluorophenyl)-3-hydroxy-5-[4-(1H-1,2,3,4-tetrazol-5-yl)phenyl]-1H-pyridin-2-one (shown in grey) was determined from MDCK cells after 24 hours using the MTT assay. Results are shown in FIG. 1.

Example 64

Inhibition of HIV-1 Integrase

The two metal binding motif of these compounds allows for potential cross reactivity with other drug targets with two metal containing active sites. Compounds were tested for LEDGF independent integration (strand transfer) and 3' processing based on established protocols (Kessl et al.; J Biol Chem, 2012; 287:16801-16811).

The 3'-processing was assayed using blunt ended $^{32}$P-labled 21-mer synthetic double stranded U5 DNA. The strand transfer assay used $^{32}$P-labled recessed end 19-mer synthetic double stranded U5 DNA. 500 nM integrase was pre-incubated with compound for 30 minutes on ice in 50 mM MOPS (pH 7.2) buffer containing 2 mM β-mercaptoethanol, 50 mM NaCl and 10 mM MgCl$_2$. 50 nM DNA substrate was added to the reaction and incubated at 37° C. for 1 hour when the reactions were stopped with 50 mM EDTA. The reaction products are subjected to denaturing polyacrylamide gel electrophoresis and visualized using a Storm 860 Phosphorimager (Amersham Biosciencs). The IC$_{50}$s of representative compounds of formula (I) as detected with a LEDGF independent integration assay or a 3'-processing assay are shown in the following table.

| Structure | IC$_{50}$ (μM) Strand Transfer | IC$_{50}$ (μM) 3'-Process |
|---|---|---|
| (structure) | 6.0 ± 0.8 | 8.2 ± 2.5 |
| (structure) | 11.7 ± 1.5 | 20.8 ± 5.8 |
| (structure) | 15.7 ± 0.9 | 11.6 ± 1.6 |
| (structure) | 20.5 ± 1.3 | 22.2 ± 2.5 |
| (structure) | 23.7 ± 2.7 | 12.6 ± 3.2 |
| (structure) | 50.7 ± 2.9 | 7.4 ± 1.6 |

Example 65

Binding to HIV-1 RNase H

RT constructs RT52A (crystallization optimized mutant) were constructed, expressed, and purified as described previously. (Bauman et al. Nucl. Acids Res, 2008; 36: 5083-5092)). Prior to crystallization, RT52A (20 mg/ml) was incubated with rilpivirine (TMC278/Edurant) at 1:1.5 molar protein to drug ratio at room temperature (~23° C.) for 30 minutes. RT52A-rilpivirine crystals were produced in hanging drops at 4° C. with a 1:1 ratio of protein and well solution containing 11% PEG 8000, 4% PEG 400, 50 mM imidazole pH 6.6, 10 mM spermine, 15 mM MgSO$_4$, 100 mM ammonium sulfate, and 5 mM tris(2-carboxyethyl)-phosphine and an experimentally optimized concentration of microseeds from previously generated crystals (preseeding).

Figure 3:
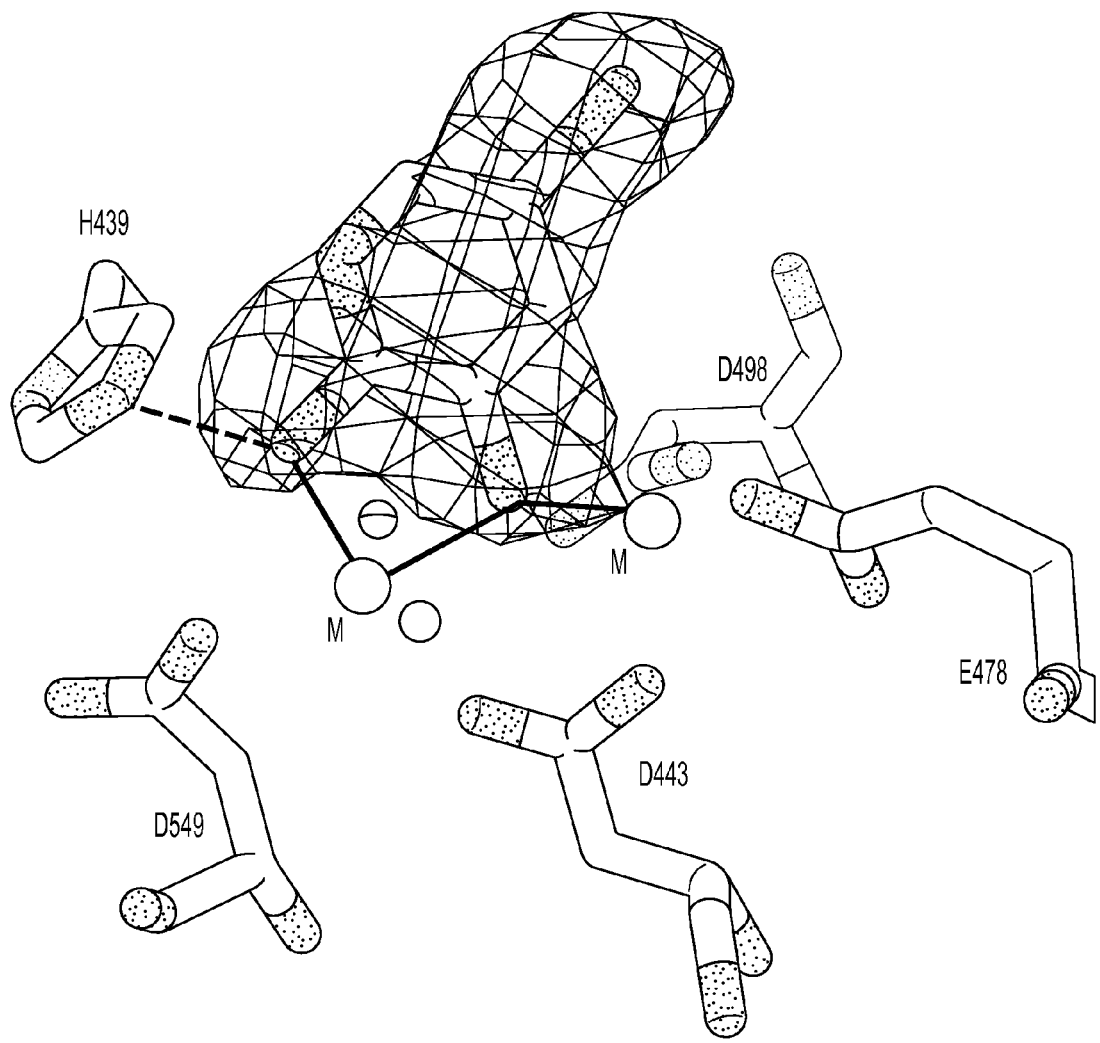
FIG. 3 illustrates the crystal structure of 5-bromopyridine-2,3-diol bound to the RNase H active site of HIV-1 from Example 65.

The compound/cryo soaking solutions were prepared with crystallization well solution with the addition of 80 mM L-arginine, 5% (v/v) ethylene glycol, 1 mM MnSO$_4$ and 20% (v/v) d$_6$-DMSO (containing 20 mM final concentration of 5-bromopyridine-2,3-diol). Crystals of RT52A-rilpivirine were harvested two weeks to four months after crystals formed. The crystals were placed in compound/cryo soaking drops for one to two minutes before flash cooling in liquid nitrogen. Data collection was performed at the Cornell High Energy Synchrotron Source (CHESS) F1 beamlin. The diffraction data were indexed, processed, scaled and merged using HKL2000I.[39] Initial datasets from crystals were collected to minimize the time of collection by increasing the oscillation range per image and decreasing exposure time. F$_o$-F$_o$ maps (as described previously) were immediately calculated using CNS and visualized with Coot.[41, 42] Datasets for crystals containing bound fragments were than recollected to improve maximum X-ray diffraction resolution. High-resolution datasets containing bound fragments were further refined using PHENIX and Coot.[40, 41] Crystal structure figures were made with MacPyMol (Schrödinger, New York, N.Y.). Results are shown in FIG. 3.

Example 66

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |

-continued

| (i) Tablet 1 | mg/tablet |
|---|---|
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula I:

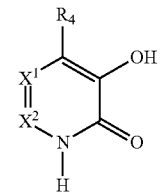

I wherein:
$X^1$ is $CR_5$; $X^2$ is $CR_6$;
$R_4$ is H, halo, cyano, nitro, $(C_2-C_6)$alkenyl, $(C_2-C_6)$alkynyl, $(C_1-C_6)$alkoxy, $(C_3-C_{12})$carbocycle, heteroaryl, heterocycle, —$NR^aR^b$, —$S(O)_nR^c$, —$S(O)_nNR^aR^b$, —$N(R^y)S(O)_nR^c$, —$COOR^c$, or —$CONR^aR^b$, wherein each $(C_2-C_6)$alkenyl, $(C_2-C_6)$alkynyl, $(C_1-C_6)$alkoxy, $(C_3-C_{12})$carbocycle of $R_4$ is optionally substituted with one or more groups independently selected from $R_m$; and wherein each heterocycle, and heteroaryl of $R_4$ is optionally substituted with one or more groups independently selected from $R_n$;

$R_5$ is H, halo, cyano, nitro, $(C_1-C_6)$alkyl, $(C_2-C_6)$alkenyl, $(C_2-C_6)$alkynyl, $(C_1-C_6)$alkoxy, $(C_3-C_{12})$carbocycle, aryl, heteroaryl, heterocycle, —$NR^aR^b$, —$S(O)_nR^c$, —$N(R^y)S(O)_nR^c$, —$S(O)_nNR^aR^b$, —$COOR^c$, or —$CONR^aR^b$, wherein each $(C_1-C_6)$alkyl, $(C_2-C_6)$alkenyl, $(C_2-C_6)$alkynyl, $(C_1-C_6)$alkoxy, $(C_3-C_{12})$carbocycle of $R_5$ is optionally substituted with one or more groups independently selected from $R_m$; and wherein each aryl, heterocycle, and heteroaryl of $R_5$ is optionally substituted with one or more groups independently selected from $R_n$;

$R_6$ is $(C_3-C_{12})$carbocycle, aryl, or heteroaryl, wherein $(C_3-C_{12})$carbocycle of $R_6$ is optionally substituted with one or more groups independently selected from $R_m$; and wherein each aryl and heteroaryl of $R_6$ is optionally substituted with one or more groups independently selected from $R_n$;

each $R^a$ and $R^b$ is independently selected from hydrogen, $(C_1-C_6)$alkyl, $(C_1-C_6)$alkanoyl, aryl$(C_1-C_6)$alkyl, heteroaryl$(C_1-C_6)$alkyl, $(C_3-C_{12})$carbocycle, aryl, and heteroaryl, wherein each $(C_1-C_6)$alkyl, $(C_1-C_6)$alkanoyl, and $(C_3-C_{12})$carbocycle of $R^a$ and $R^b$ is optionally substituted with one or more groups independently selected from $R_m$; and wherein each aryl and heteroaryl of $R^a$ and $R^b$ is optionally substituted with one or more groups independently selected from $R_n$;

each $R^c$ is independently selected from hydrogen, hydroxy, $(C_1-C_6)$alkyl, $(C_1-C_6)$alkanoyl, aryl$(C_1-C_6)$alkyl, heteroaryl$(C_1-C_6)$alkyl, $(C_3-C_{12})$carbocycle, aryl, and heteroaryl, wherein each $(C_1-C_6)$alkyl, $(C_1-C_6)$alkanoyl, and $(C_3-C_{12})$carbocycle of $R^c$ is optionally substituted with one or more groups independently selected from $R_m$; and wherein each aryl and heteroaryl of $R^c$ is optionally substituted with one or more groups independently selected from $R_n$;

each $R^e$ and $R^f$ is independently selected from hydrogen, $(C_1\text{-}C_6)$alkyl, $(C_1\text{-}C_6)$alkanoyl, aryl$(C_1\text{-}C_6)$alkyl, heteroaryl$(C_1\text{-}C_6)$alkyl, $(C_3\text{-}C_{12})$carbocycle, aryl, and heteroaryl; and each $R^g$ is independently selected from hydrogen, $(C_1\text{-}C_6)$alkyl, $(C_1\text{-}C_6)$alkanoyl, aryl$(C_1\text{-}C_6)$alkyl, heteroaryl$(C_1\text{-}C_6)$alkyl, $(C_3\text{-}C_{12})$carbocycle, aryl, and heteroaryl;

each $R_m$ is independently selected from cyano, halo, nitro, hydroxy, oxo, carboxy, aryl, heteroaryl, heterocycle, aryloxy, heteroaryloxy, heterocycleoxy, —S(O)$_n$R$^g$, —N(R$^y$)S(O)$_n$R$^g$, —S(O)$_n$NR$^e$R$^f$, —COOR$^g$, and —CONR$^e$R$^f$; wherein each heterocycle of $R_m$ is optionally substituted with one or more groups independently selected from $(C_1\text{-}C_6)$alkyl, $(C_2\text{-}C_6)$alkenyl, $(C_2\text{-}C_6)$alkynyl, $(C_1\text{-}C_6)$alkoxy, $(C_3\text{-}C_{12})$carbocycle, cyano, halo, nitro, hydroxy, oxo, carboxy, aryloxy, heteroaryloxy, heterocycleoxy, —NR$^e$R$^f$, —S(O)$_n$R$^g$, —N(R$^y$)S(O)$_n$R$^g$, —COOR$^g$, and —CONR$^e$R$^f$; and wherein each aryl and heteroaryl of $R_m$ is optionally substituted with one or more groups independently selected from $(C_1\text{-}C_6)$alkyl, $(C_2\text{-}C_6)$alkenyl, $(C_2\text{-}C_6)$alkynyl, $(C_1\text{-}C_6)$alkoxy, $(C_3\text{-}C_{12})$carbocycle, cyano, halo, nitro, hydroxy, carboxy, $R_{m1}$, aryloxy, heteroaryloxy, heterocycleoxy, —NR$^e$R$^f$, —S(O)$_n$R$^g$, —N(R$^y$)S(O)$_n$R$^g$, —S(O)—NR$^e$R$^f$, $(C_1\text{-}C_6)$alkoxy, —COOR$^g$, and —CONR$^e$R$^f$;

each $R_{m1}$ is independently selected from aryl and heteroaryl, wherein any aryl and heteroaryl of $R_{m1}$ is optionally substituted with one or more groups independently selected from $(C_1\text{-}C_6)$alkyl, $(C_2\text{-}C_6)$alkenyl, $(C_2\text{-}C_6)$alkynyl, $(C_1\text{-}C_6)$alkoxy, $(C_3\text{-}C_{12})$carbocycle, heterocycle, aryl, heteroaryl, cyano, halo, nitro, hydroxy, carboxy, —NR$^e$R$^f$, —S(O)$_n$R$^g$, —N(R$^y$)S(O)$_n$R$^g$, —S(O)$_n$NR$^e$R$^f$, $(C_1\text{-}C_6)$alkoxy, —COOR$^g$, and —CONR$^e$R$^f$;

each $R_n$ is independently selected from $(C_1\text{-}C_6)$alkyl, $(C_2\text{-}C_6)$alkenyl, $(C_2\text{-}C_6)$alkynyl, $(C_1\text{-}C_6)$alkoxy, $(C_3\text{-}C_{12})$carbocycle, heteroaryl, heterocycle, cyano, halo, nitro, hydroxy, carboxy, heteroaryloxy, heterocycleoxy, —NR$^e$R$^f$, —S(O)$_n$R$^g$, —N(R$^y$)S(O)$_n$R$^g$, —S(O)$_n$NR$^e$R$^f$, —COOR$^g$, and —CONR$^e$R$^f$; wherein each $(C_1\text{-}C_6)$alkyl, $(C_2\text{-}C_6)$alkenyl, $(C_2\text{-}C_6)$alkynyl, $(C_1\text{-}C_6)$alkoxy, heterocycle, and $(C_3\text{-}C_{12})$carbocycle of $R_n$ is optionally substituted with one or more groups independently selected from cyano, halo, nitro, hydroxy, carboxy, aryloxy, heteroaryloxy, heterocycleoxy, —NR$^e$R$^f$, —S(O)$_n$R$^g$, —N(R$^y$)S(O)$_n$R$^g$, —COOR$^g$, and —CONR$^e$R$^f$; wherein each aryl and heteroaryl of $R_n$ is optionally substituted with one or more groups independently selected from cyano, halo, nitro, hydroxy, oxo, carboxy, aryl, heteroaryl, aryloxy, heteroaryloxy, heterocycleoxy, —NR$^e$R$^f$, —S(O)$_n$R$^g$, —N(R$^y$)S(O)$_n$R$^g$, —COOR$^g$, —S(O)$_n$NR$^e$R$^f$, $(C_1\text{-}C_6)$alkoxy, and —CONR$^e$R$^f$;

each $R^y$ is independently selected from hydrogen and $(C_1\text{-}C_6)$alkyl; and n is 0, 1, or 2;

or a salt thereof.

2. The compound of claim 1 wherein $R_5$ is H, halo, $(C_1\text{-}C_6)$alkyl, $(C_3\text{-}C_{12})$carbocycle, —NR$^a$R$^b$, or aryl, wherein each $(C_1\text{-}C_6)$alkyl and $(C_3\text{-}C_{12})$carbocycle is optionally substituted with one or more groups independently selected from $R_m$; and wherein any aryl is optionally substituted with one or more groups independently selected from $R_n$.

3. The compound of claim 1 wherein $R_5$ is phenyl, benzyl, 2-pyridyl, 3-pyridyl, or 4-pyridyl wherein the phenyl or pyridyl is optionally substituted with one or more groups selected from the group consisting of —COOH, —CONR$^e$R$^f$, —SO$_3$H, —SO$_2$NHCH$_3$, OH, OCH$_3$, F, Cl, Br, CH$_3$; or wherein $R_5$ is methyl substituted with COOH, SO$_3$H, SO$_2$NHCH$_3$, OH, a CF$_3$ or a tetrazole.

4. The compound of claim 1 wherein $R_6$ is $(C_3\text{-}C_{12})$carbocycle or aryl, wherein $(C_3\text{-}C_{12})$carbocycle is optionally substituted with one or more groups independently selected from $R_m$; and wherein any aryl is optionally substituted with one or more groups independently selected from $R_n$.

5. The compound of claim 1 wherein $R_6$ is phenyl, 4-tert-butylphenyl, 4-trifluoromethylphenyl, 4-fluorophenyl, 3-methoxyphenyl, 3-fluorophenyl, cyclohex-1-en-1-yl, 3,4-dihydroxyphenyl, 4-cyclohexylphenyl, 4-nitrophenyl, 3-aminocarbonylphenyl, or 4-aminocarbonylphenyl.

6. The compound of claim 1 wherein $R_6$ is phenyl, which is optionally substituted with one or more substituents selected from the group consisting of F, Cl, Br, OCH$_3$, CH$_3$, and CONR$^e$R$^f$.

7. The compound of claim 1 wherein:

$R_5$ is $(C_1\text{-}C_3)$alkyl, aryl, heteroaryl, wherein each $(C_1\text{-}C_3)$ alkyl of $R_5$ is optionally substituted with one or more groups independently selected from $R_m$; and wherein each aryl and heteroaryl of $R_5$ is optionally substituted with one or more groups independently selected from $R_n$; and $R_6$ is $(C_3\text{-}C_8)$carbocycle, aryl, heteroaryl, wherein $(C_3\text{-}C_{12})$carbocycle of $R_6$ is optionally substituted with one or more groups independently selected from $R_m$; and wherein each aryl and heteroaryl of $R_6$ is optionally substituted with one or more groups independently selected from $R_n$.

8. The compound of claim 1 wherein:

$R_4$ is H;

$R_5$ is H, halo or aryl wherein each aryl of $R_5$ is optionally substituted with one or more groups independently selected from $R_n$;

$R_6$ is $(C_3\text{-}C_{12})$carbocycle or aryl, wherein each $(C_3\text{-}C_{12})$ carbocycle of $R_6$ is optionally substituted with one or more groups independently selected from $R_m$; and wherein each aryl of $R_6$ is optionally substituted with one or more groups independently selected from $R_n$.

9. The compound of claim 1 wherein:

$R_4$ is H;

$R_5$ is H, halo or phenyl wherein each phenyl of $R_5$ is optionally substituted with one or more groups independently selected from $R_n$;

$R_6$ is $(C_6)$carbocycle or phenyl, wherein each $(C_6)$carbocycle of $R_6$ is optionally substituted with one or more groups independently selected from $R_m$; and wherein each phenyl of $R_6$ is optionally substituted with one or more groups independently selected from $R_n$.

10. A compound which is:

-continued
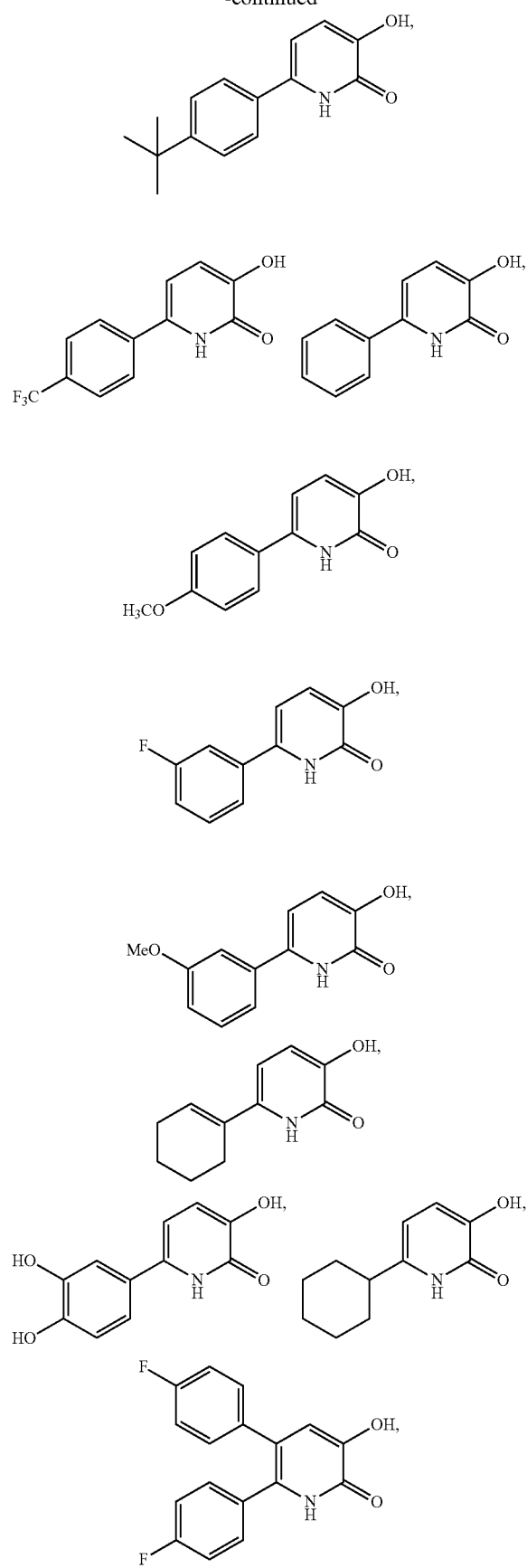
-continued
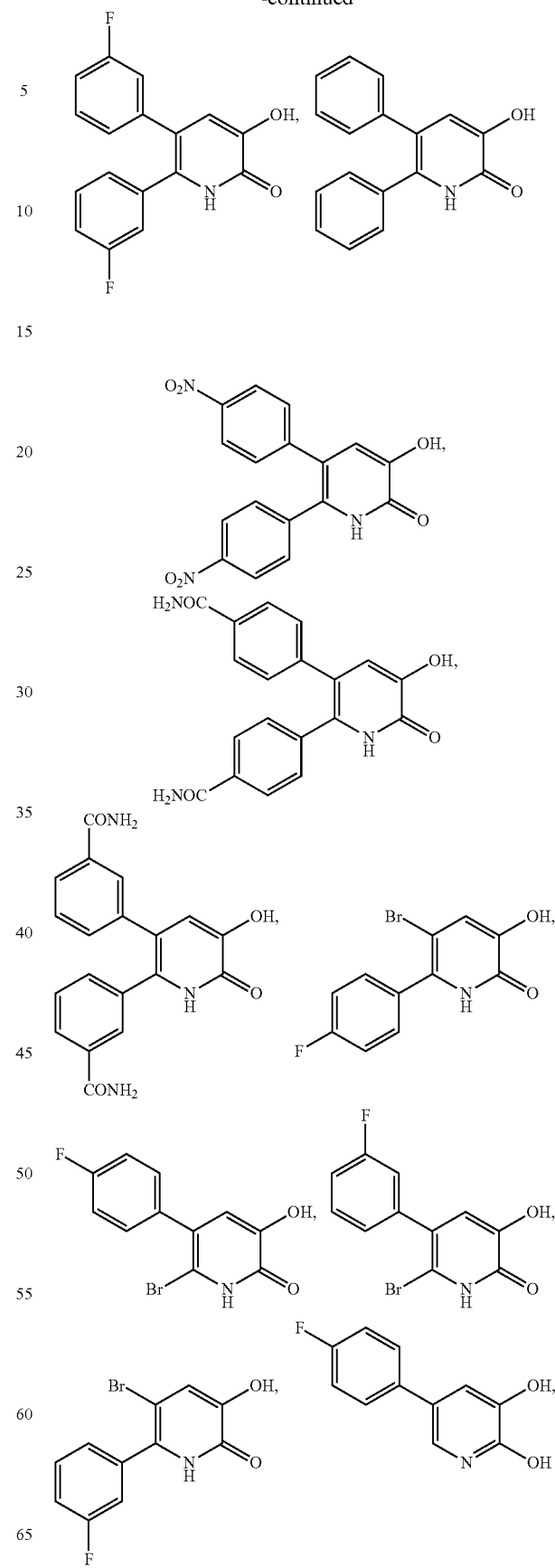

-continued
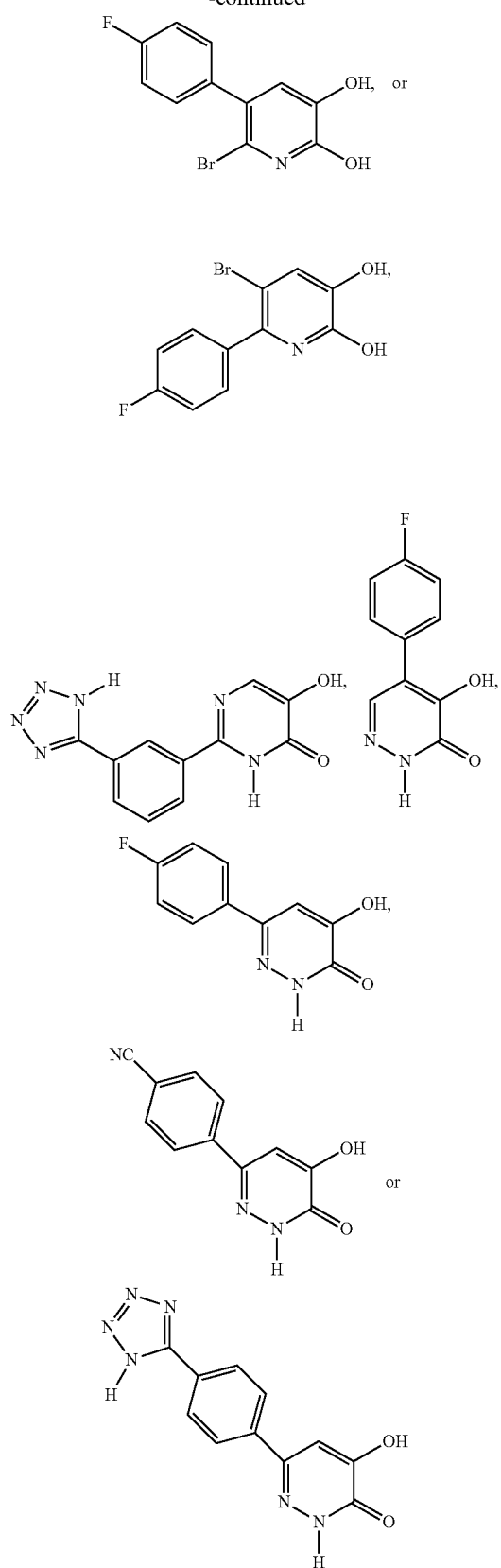
or a pharmaceutically acceptable salt thereof.
11. A compound which is:
or a pharmaceutically acceptable salt thereof.

135
-continued
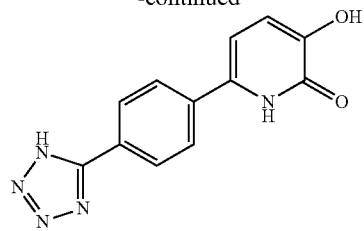
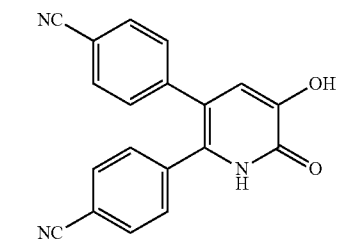
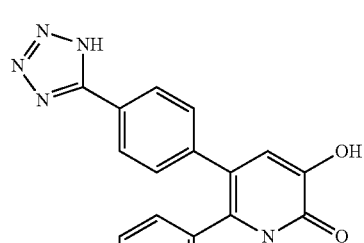
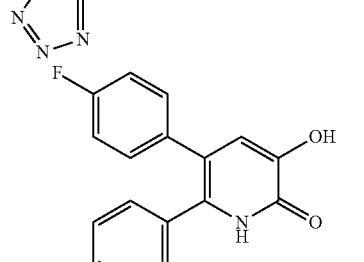
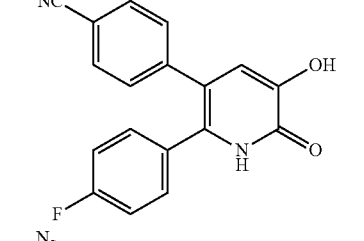
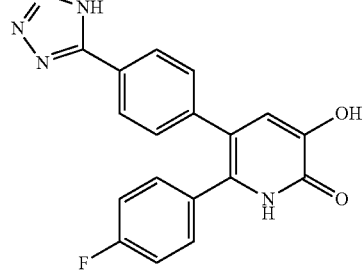
136
-continued
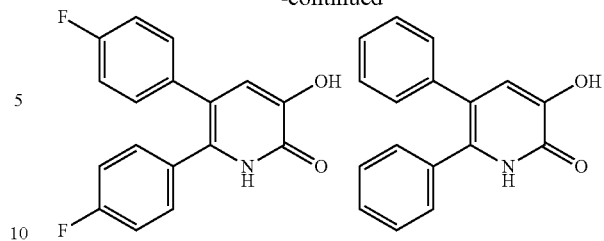
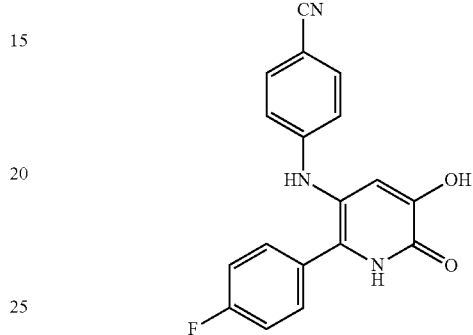
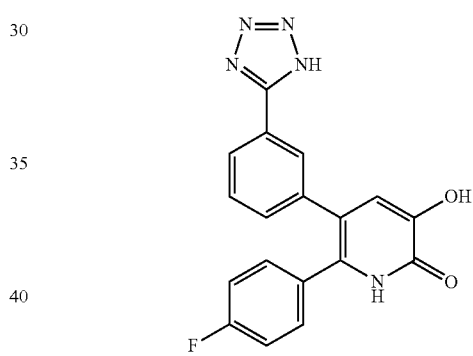
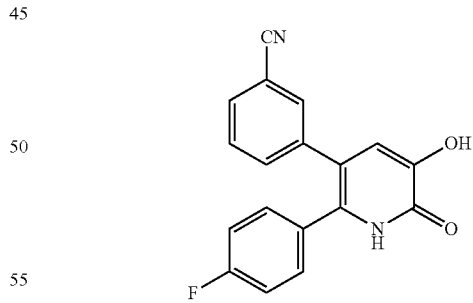
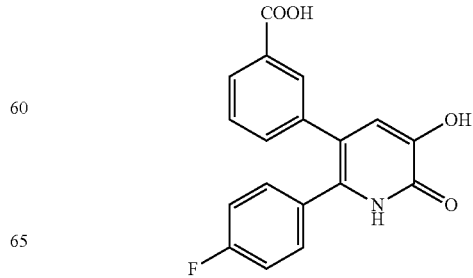

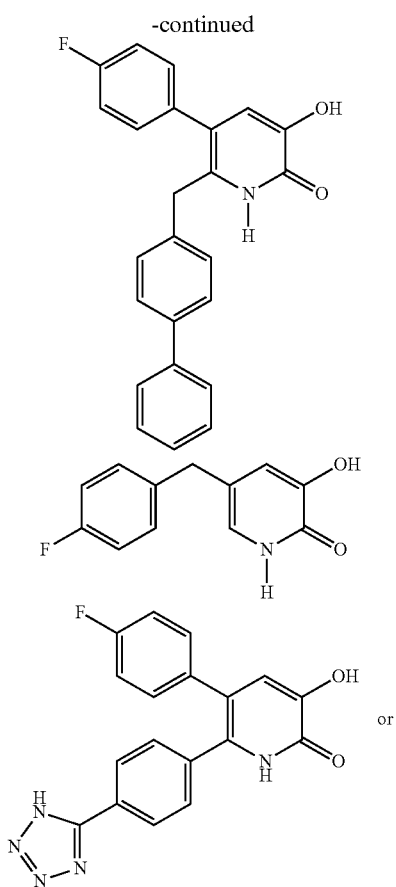

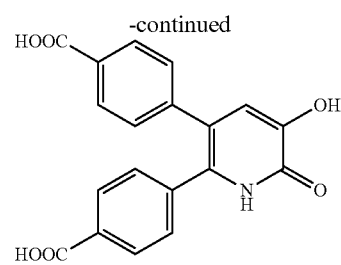

or a pharmaceutically acceptable salt thereof.

12. The compound of claim 1 wherein $R_5$ is phenyl that is optionally substituted with one or more groups independently selected from $R_n$.

13. The compound of claim 1 wherein $R_6$ is phenyl that is optionally substituted with one or more groups independently selected from $R_n$.

14. A pharmaceutical composition comprising a compound of formula I as described in claim 1 or a pharmaceutically salt thereof, and a pharmaceutically acceptable diluent or carrier.

15. A method to promote an antiviral effect in an animal comprising administering a compound of formula I as described in claim 1, or a pharmaceutically salt to the animal.

16. A method to treat influenza in an animal comprising administering a compound of formula I as described in claim 1, or a pharmaceutically salt to the animal.

17. A method to treat HIV in an animal comprising administering a compound of formula I as described in claim 1, or a pharmaceutically salt thereof, to the animal.

* * * * *

UNITED STATES PATENT AND TRADEMARK OFFICE
CERTIFICATE OF CORRECTION

| | |
|---|---|
| PATENT NO. | : 9,573,938 B2 |
| APPLICATION NO. | : 14/426948 |
| DATED | : February 21, 2017 |
| INVENTOR(S) | : Edmond J. LaVoie et al. |

Page 1 of 1

It is certified that error appears in the above-identified patent and that said Letters Patent is hereby corrected as shown below:

On the Title Page

Item (56), Other Publications, please delete "M et al.," and insert -- IM et al., --;

In the Claims

Column 129, Line 27, Claim 1, please delete "-S(O)-$NR^eR^f$" and insert -- -S(O)$_n$$NR^eR^f$ --;

Column 130, Line 19, Claim 6, please delete "phenyl," and insert -- phenyl --;

Column 133, Lines 20-65, Claim 10, please delete the following compounds:

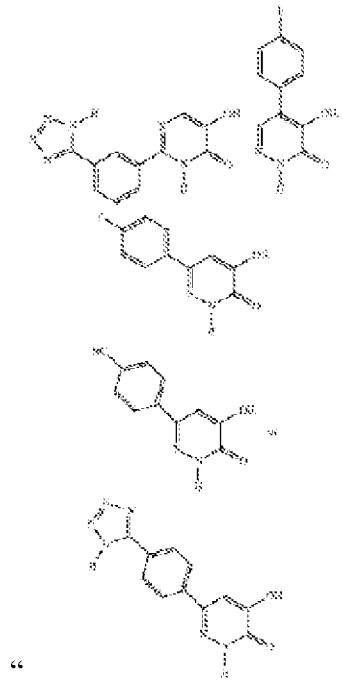

" therefor.

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*